US009068987B2

(12) United States Patent
Jay et al.

(10) Patent No.: US 9,068,987 B2
(45) Date of Patent: *Jun. 30, 2015

(54) INHIBITORS OF EXTRACELLULAR HSP90

(71) Applicant: TRUSTEES OF TUFTS COLLEGE, Medford, MA (US)

(72) Inventors: Daniel G. Jay, Jamaica Plain, MA (US); Brenda K. Eustace, Brookline, MA (US); Takashi Sakurai, Tokyo (JP)

(73) Assignee: TRUSTEES OF TUFTS COLLEGE, Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/083,479

(22) Filed: Nov. 19, 2013

(65) Prior Publication Data

US 2014/0079720 A1    Mar. 20, 2014

Related U.S. Application Data

(63) Continuation of application No. 13/870,955, filed on Apr. 25, 2013, now abandoned, which is a continuation of application No. 12/951,737, filed on Nov. 22, 2010, now Pat. No. 8,529,891, which is a continuation of application No. 11/224,726, filed on Sep. 12, 2005, now Pat. No. 7,959,915, which is a continuation of application No. PCT/EP2004/002422, filed on Mar. 9, 2004.

(60) Provisional application No. 60/454,813, filed on Mar. 12, 2003.

(30) Foreign Application Priority Data

Jul. 3, 2003   (EP) .................................... 03015115

(51) Int. Cl.
| | |
|---|---|
| *G01N 33/574* | (2006.01) |
| *A61K 31/366* | (2006.01) |
| *C07K 16/30* | (2006.01) |
| *A61K 39/395* | (2006.01) |
| *A61K 31/395* | (2006.01) |
| *A61K 47/48* | (2006.01) |
| *A61K 39/00* | (2006.01) |

(52) U.S. Cl.
CPC ........ *G01N 33/574* (2013.01); *G01N 33/57484* (2013.01); *A61K 31/366* (2013.01); *A61K 2039/505* (2013.01); *C07K 16/30* (2013.01); *C07K 2317/622* (2013.01); *A61K 39/39558* (2013.01); *C07K 2317/34* (2013.01); *A61K 31/395* (2013.01); *A61K 47/4823* (2013.01); *A61K 47/48923* (2013.01)

(58) Field of Classification Search
CPC ................ G01N 33/57484; A61K 2039/6043
See application file for complete search history.

(56) References Cited

U.S. PATENT DOCUMENTS

| | | | |
|---|---|---|---|
| 4,208,479 A | 6/1980 | Zuk et al. | |
| 5,188,964 A | 2/1993 | McGuire et al. | |
| 5,541,077 A | 7/1996 | Burnie et al. | |
| 5,777,083 A | 7/1998 | Burnie et al. | |
| 6,335,157 B1 * | 1/2002 | Gonzalez et al. | ............... 435/4 |
| 6,852,318 B1 | 2/2005 | Varner | |
| 7,442,776 B2 | 10/2008 | Young et al. | |
| 7,959,915 B2 | 6/2011 | Jay et al. | |
| 8,529,891 B2 | 9/2013 | Jay et al. | |
| 2004/0197328 A1 | 10/2004 | Young et al. | |
| 2007/0154478 A1 | 7/2007 | Burnie et al. | |
| 2008/0038267 A1 | 2/2008 | Burnie et al. | |

FOREIGN PATENT DOCUMENTS

| | | |
|---|---|---|
| EP | 0406029 B1 | 3/1995 |
| WO | 91/00351 A1 | 1/1991 |
| WO | 94/04676 A1 | 3/1994 |
| WO | 00/53169 A2 | 9/2000 |
| WO | 01/76627 A1 | 10/2001 |
| WO | 02/15925 A1 | 2/2002 |
| WO | 2004/081037 | 9/2004 |
| WO | 2006/03384 A1 | 12/2006 |
| WO | 2007/77454 A2 | 12/2007 |

OTHER PUBLICATIONS

Chee et al. (Cancer Res. 1976 36:1503-1509).*
Conroy and Latchman (British J. Cancer 1996, 74: 717-721).*
Jameel et al. (Int. J. Cancer 1992 50:409-415).*
Neckers L et al., "Geldanamycin as a potential anti-cancer agent: its molecular target and biochemical activity." Invest New Drugs. 1999;17(4):361-73.
Chiosis G et al., "Development of a purine-scaffold novel class of Hsp90 binders that inhibit the proliferation of cancer cells and induce the degradation of Her2 tyrosine kinase." Bioorg Med Chem. Nov. 2002; 10(11):3555-64.
Ferrarini M et al., "Unusual expression and localization of heat-shock proteins in human tumor cells." Int J Cancer. Jun. 19, 1992;51(4):613-9.
Marcu MG et al., "Novobiocin and related coumarins and depletion of heat shock protein 90-dependent signaling proteins." J Natl Cancer Inst. Feb. 2, 2000;92(3):242-8.
Drolet DW et al., "A high throughput platform for systematic evolution of ligands by exponential enrichment (SELEX)." Comb Chem High Throughput Screen. Oct. 1999;2(5):271-8.

(Continued)

*Primary Examiner* — Peter J Reddig
(74) *Attorney, Agent, or Firm* — Nixon Peabody LLP

(57) ABSTRACT

The present invention describes inhibitors of extracellular Hsp90. The inhibition of extracellular Hsp90 leads to a reduction of the invasiveness of the tumor cells. Furthermore, the invention relates to the use of molecules inhibiting extracellular Hsp90 function for the manufacture of a medicament for the treatment or prevention of invasion and/or metastatic potential of cancer cells.

12 Claims, 29 Drawing Sheets

(56) References Cited

OTHER PUBLICATIONS

Janeway et al. (Immunobiology 5, 2001, p. 100-101).
Rudikoff et al (Proc. Natl. Acad. Sci. USA 1982 vol. 79: 1979-1983).
Bowie et al. (Science, 247:1306-1310, 1990).
Gussow et al. (1991, Methods in Enzymology 203:99-121).
MacCallum et al. (J. Mol. Biol. (1996) 262, 732-745).
Casset et al. (BBRC 2003 307:198-205).
Wu et al. (J. Mol. Biol. (1999) 294, 151-162).
Stellas et al. (FEBS J. 2008 275 (Suppl. 1): 345).
Eustace et al. (Nature Cell Biology, Jun. 2004, 6:507-514).
Taber's Cyclopedic Medical Dictionary (1985, F. A. Davis Company, Philadelphia, p. 274).
Busken, C et al, (Digestive Disease Week Abstracts and Itinerary Planner, 2003, abstract No. 850).
Kaiser (Science, 2006, 313:1370).
Krontiris and Capizzi (Internal Medicine, 4th Edition, Editor-in-chief Jay Stein, Elsevier Science, 1994 Chapters 71-72, pp. 699-729).
Carter, S. K. et al. Chemotherapy of Cancer; Second edition; John Wiley & Sons: New York, 1981; appendix C.
Freshney (Culture of Animal Cells, A Manual of Basic Technique, Alan R. Liss, Inc., 1983, New York, p. 4).
Dermer (Bio/Technology, 1994, 12:320).
Drexler et al (Leukemia and Lymphoma, 1993, 9:1-25).
Zellner et al (Clin. Can. Res., 1998, 4:1797-1780).
Zips et al (In vivo, 2005, 19:1-7).
Gura (Science, 1997, 278:1041-1042).
Jain (Sci. Am., 1994, 271:58-65).
Curti (Crit. Rev. in Oncology/Hematology, 1993, 14:29-39).
Conroy et al. (European J. Cancer, 1998, 34:942-943).
Byers, T (CA Journal, vol. 49, No. 6, Nov./Dec. 1999).
Cotterchio et al, 2000, Chronic Diseases in Canada, (Electronic Version downloaded from www.phac-aspc.gc.ca/publicat/cdicmcc/21-2/f_e.html).
Martin et al (Journal of the National Cancer Institute, 92:1126-1135).
Becker et al., Experimental Dermatology, 13(1):27-32 (2004). "Induction of Hsp90 protein expression in malignant melanomas and melanoma metastases."
Nemoto et al., JBC, 272(42):26179-87 (1997). "Domain structures and immunogenic regions of the 90kDa heat-shock protein (Hsp90). Probing with a library of anti-Hsp90 monoclonal antibodies and limited proteolysis."
Miyata, Yoshihiko, Folio Pharmacol, Japan (Nihon Yakurigaku Zasshi), Jan. 2003, vol. 121, No. 1, pp. 33-42. "Molecular chaperone HSP90 as a novel cancer target for cancer chemotherapy."
Stellas et al., Clin Cancer Res, 13(6):1831-1838 (2007). "Monoclonal antibody 4C5 immunostains human melanomas and inhibits melanoma cell invasion and metastasis."
Stellas et al., BMC Cell Biology, 11:51 (2010). "Monoclonal antibody 4C5 prevents activation of MMP2 and MMP9 by disrupting their interaction with extracellular HSP90 and inhibits formation of metastatic breast cancer cell deposits."
Tsutsumi et al., Oncogene, 27:2478-2487 (2008). "A small molecule cell-impermeant Hsp90 antagonist inhibits tumor cell motility and invasion."
Orr et al., Amer J Pathol, 110:41-47 (1983).
Tannock, I.F., Experimental Chemotherapy, Ch. 19, p. 338 and 352-359 in The Basic Science of Oncology, Tannock and Hill, eds., New York 1992.
Dillman, Annals of Internal Medicine, 111:592-603 (1989).
Price et al., Clinical and Experimental Metastasis, 19(Suppl):58, Abstract S-03 (2002).
efungumab (http://www.ncbi.nlm.nih.gov/mesh/?term=mycograb&report=Full&format=text, 2006).

* cited by examiner

```
>gi|13129150|ref|NP_005339.1|heatshock90kDprotein1,alpha [Homosapiens]
Mass (average): 84659.7 Identifier: gi|13129150 Database:
D:/Proteindatabases/human.fasta
Protein Coverage: 172/732=23.5% by amino acid count, 19906.0/84659.7=23.5% by mass
```
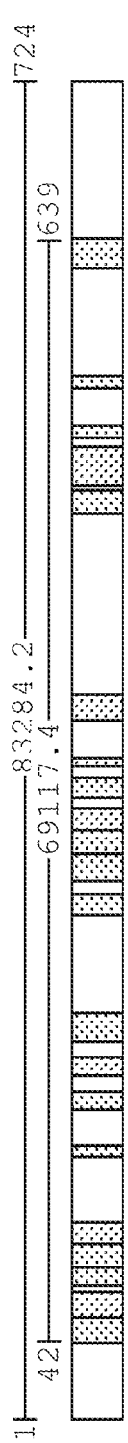
```
>gi|13654497|ref|XP_018115.1|heat shock90kD protein1,beta [Homo sapiens]
Mass (average): 83264.2 Identifier: gi|13654497 Database:
D:/Proteindatabases/human.fasta
Protein Coverage: 241/724=33.3% by amino acid count, 27710.1/83264.2=33.3% by mass
```
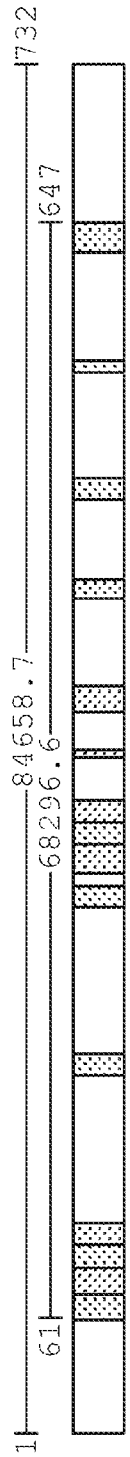
FIG. 9

Nucleotide Sequences pXP10

```
   1  GACGAAAGGG CCTCGTGATA CGCCTATTTT TATAGGTTAA TGTCATGATA
      CTGCTTTCCC GGAGCACTAT GCGGATAAAA ATATCCAATT ACAGTACTAT
  51  ATAATGGTTT CTTAGACGTC AGGTGGCACT TTTCGGGGAA ATGTGCGCGG
      TATTACCAAA GAATCTGCAG TCCACCGTGA AAAGCCCCTT TACACGCGCC
 101  AACCCCTATT TGTTTATTTT TCTAAATACA TTCAAATATG TATCCGCTCA
      TTGGGGATAA ACAAATAAAA AGATTTATGT AAGTTTATAC ATAGGCGAGT
 151  TGAGACAATA ACCCTGATAA ATGCTTCAAT AATATTGAAA AAGGAAGAGT
      ACTCTGTTAT TGGGACTATT TACGAAGTTA TTATAACTTT TTCCTTCTCA
 201  ATGAGTATTC AACATTTCCG TGTCGCCCTT ATTCCCTTTT TTGCGGCATT
      TACTCATAAG TTGTAAAGGC ACAGCGGGAA TAAGGGAAAA AACGCCGTAA
 251  TTGCCTTCCT GTTTTTGCTC ACCCAGAAAC GCTGGTGAAA GTAAAGATG
      AACGGAAGGA CAAAACGAG TGGGTCTTTG CGACCACTTT CATTTCTAC
 301  CTGAAGATCA GTTGGGTGCT CGAGTGGGTT ACATCGAACT GGATCTCAAC
      GACTTCTAGT CAACCCACGA GCTCACCCAA TGTAGCTTGA CCTAGAGTTG
 351  AGCGGTAAGA TCCTTGAGAG TTTTCGCCCC GAAGAACGTT TTCCAATGAT
      TCGCCATTCT AGGAACTCTC AAAAGCGGGG CTTCTTGCAA AAGGTTACTA
 401  GAGCACTTTT AAAGTTCTGC TATGTGGCGC GGTATTATCC CGTATTGACG
      CTCGTGAAAA TTTCAAGACG ATACACCGCG CCATAATAGG GCATAACTGC
 451  CCGGGCAAGA GCAACTCGGT CGCCGCATAC ACTATTCTCA GAATGACTTG
      GGCCCGTTCT CGTTGAGCCA GCGGCGTATG TGATAAGAGT CTTACTGAAC
 501  GTTGAGTACT CACCAGTCAC AGAAAAGCAT CTTACGGATG GCATGACAGT
      CAACTCATGA GTGGTCAGTG TCTTTTCGTA GAATGCCTAC CGTACTGTCA
 551  AAGAGAATTA TGCAGTGCTG CCATAACCAT GAGTGATAAC ACTGCGGCCA
      TTCTCTTAAT ACGTCACGAC GGTATTGGTA CTCACTATTG TGACGCCGGT
 601  ACTTACTTCT GACAACGATC GGAGGACCGA AGGAGCTAAC CGCTTTTTTG
      TGAATGAAGA CTGTTGCTAG CCTCCTGGCT TCCTCGATTG GCGAAAAAAC
 651  CACAACATGG GGGATCATGT AACTCGCCTT GATCGTTGGG AACCGGAGCT
      GTGTTGTACC CCCTAGTACA TTGAGCGGAA CTAGCAACCC TTGGCCTCGA
 701  GAATGAAGCC ATACCAAACG ACGAGCGTGA CACCACGATG CCTGTAGCAA
      CTTACTTCGG TATGGTTTGC TGCTCGCACT GTGGTGCTAC GGACATCGTT
 751  TGGCAACAAC GTTGCGCAAA CTATTAACTG GCGAACTACT TACTCTAGCT
      ACCGTTGTTG CAACGCGTTT GATAATTGAC CGCTTGATGA ATGAGATCGA
 801  TCCCGGCAAC AATTAATAGA CTGGATGGAG GCGGATAAAG TTGCAGGACC
      AGGGCCGTTG TTAATTATCT GACCTACCTC CGCCTATTTC AACGTCCTGG
 851  ACTTCTGCGC TCGGCCCTTC CGGCTGGCTG GTTTATTGCT GATAAATCTG
      TGAAGACGCG AGCCGGGAAG GCCGACCGAC CAAATAACGA CTATTTAGAC
 901  GAGCCGGTGA GCGTGGGTCT CGCGGTATCA TTGCAGCACT GGGGCCAGAT
      CTCGGCCACT CGCACCCAGA GCGCCATAGT AACGTCGTGA CCCCGGTCTA
 951  GGTAAGCCCT CCCGTATCGT AGTTATCTAC ACGACGGGGA GTCAGGCAAC
      CCATTCGGGA GGGCATAGCA TCAATAGATG TGCTGCCCCT CAGTCCGTTG
1001  TATGGATGAA CGAAATAGAC AGATCGCTGA GATAGGTGCC TCACTGATTA
      ATACCTACTT GCTTTATCTG TCTAGCGACT CTATCCACGG AGTGACTAAT
1051  AGCATTGGTA ACTGTCAGAC CAAGTTTACT CATATATACT TTAGATTGAT
      TCGTAACCAT TGACAGTCTG GTTCAAATGA GTATATATGA AATCTAACTA
1101  TTAAAACTTC ATTTTTAATT TAAAAGGATC TAGGTGAAGA TCCTTTTTGA
      AATTTTGAAG TAAAAATTAA ATTTTCCTAG ATCCACTTCT AGGAAAAACT
1151  TAATCTCATG ACCAAAATCC CTTAACGTGA GTTTTCGTTC CACTGAGCGT
      ATTAGAGTAC TGGTTTTAGG GAATTGCACT CAAAAGCAAG GTGACTCGCA
1201  CAGACCCCGT AGAAAAGATC AAAGGATCTT CTTGAGATCC TTTTTTTCTG
      GTCTGGGGCA TCTTTTCTAG TTTCCTAGAA GAACTCTAGG AAAAAAAGAC
1251  CGCGTAATCT GCTGCTTGCA AACAAAAAAA CCACCGCTAC CAGCGGTGGT
      GCGCATTAGA CGACGAACGT TTGTTTTTTT GGTGGCGATG GTCGCCACCA
1301  TTGTTTGCCG GATCAAGAGC TACCAACTCT TTTTCCGAAG GTAACTGGCT
      AACAAACGGC CTAGTTCTCG ATGGTTGAGA AAAAGGCTTC CATTGACCGA
1351  TCAGCAGAGC GCAGATACCA AATACTGTCC TTCTAGTGTA GCCGTAGTTA
```

FIG. 13B

SEQ ID NO: 3
(nucleotides 1-1400)

```
       AGTCGTCTCG CGTCTATGGT TTATGACAGG AAGATCACAT CGGCATCAAT
1401   GGCCACCACT TCAAGAACTC TGTAGCACCG CCTACATACC TCGCTCTGCT
       CCGGTGGTGA AGTTCTTGAG ACATCGTGGC GGATGTATGG AGCGAGACGA
1451   AATCCTGTTA CCAGTGGCTG CTGCCAGTGG CGATAAGTCG TGTCTTACCG
       TTAGGACAAT GGTCACCGAC GACGGTCACC GCTATTCAGC ACAGAATGGC
1501   GGTTGGACTC AAGACGATAG TTACCGGATA AGGCGCAGCG GTCGGGCTGA
       CCAACCTGAG TTCTGCTATC AATGGCCTAT TCCGCGTCGC CAGCCCGACT
1551   ACGGGGGGTT CGTGCATACA GCCCAGCTTG GAGCGAACGA CCTACACCGA
       TGCCCCCCAA GCACGTATGT CGGGTCGAAC CTCGCTTGCT GGATGTGGCT
1601   ACTGAGATAC CTACAGCGTG AGCTATGAGA AAGCGCCACG CTTCCCGAAG
       TGACTCTATG GATGTCGCAC TCGATACTCT TTCGCGGTGC GAAGGGCTTC
1651   GGAGAAAGGC GGACAGGTAT CCGGTAAGCG GCAGGGTCGG AACAGGAGAG
       CCTCTTTCCG CCTGTCCATA GGCCATTCGC CGTCCCAGCC TTGTCCTCTC
1701   CGCACGAGGG AGCTTCCAGG GGGAAACGCC TGGTATCTTT ATAGTCCTGT
       GCGTGCTCCC TCGAAGGTCC CCCTTTGCGG ACCATAGAAA TATCAGGACA
1751   CGGGTTTCGC CACCTCTGAC TTGAGCGTCG ATTTTGTGA TGCTCGTCAG
       GCCCAAAGCG GTGGAGACTG AACTCGCAGC TAAAAACACT ACGAGCAGTC
1801   GGGGGCGGAG CCTATGGAAA AACGCAGCA ACGCGGCCTT TTTACGGTTC
       CCCCCGCCTC GGATACCTTT TTGCGGTCGT TGCGCCGGAA AAATGCCAAG
1851   CTGGCCTTTT GCTGGCCTTT TGCTCACATG TTCTTTCCTG CGTTATCCCC
       GACCGGAAAA CGACCGGAAA ACGAGTGTAC AAGAAAGGAC GCAATAGGGG
1901   TGATTCTGTG GATAACCGTA TTACCGCCTT TGAGTGAGCT GATACCGCTC
       ACTAAGACAC CTATTGGCAT AATGGCGGAA ACTCACTCGA CTATGGCGAG
1951   GCCGCAGCCG AACGACCGAG CGCAGCGAGT CAGTGAGCGA GGAAGCGGAA
       CGGCGTCGGC TTGCTGGCTC GCGTCGCTCA GTCACTCGCT CCTTCGCCTT
2001   GAGCGCCCAA TACGCAAACC GCCTCTCCCC GCGCGTTGGC CGATTCATTA
       CTCGCGGGTT ATGCGTTTGG CGGAGAGGGG CGCGCAACCG GCTAAGTAAT
2051   ATGCAGCTGG CACGACAGGT TTCCCGACTG GAAAGCGGGC AGTGAGCGCA
       TACGTCGACC GTGCTGTCCA AAGGGCTGAC CTTTCGCCCG TCACTCGCGT
2101   ACGCAATTAA TGTGAGTTAG CTCACTCATT AGGCACCCCA GGCTTTACAC
       TGCGTTAATT ACACTCAATC GAGTGAGTAA TCCGTGGGGT CCGAAATGTG
2151   TTTATGCTTC CGGCTCGTAT GTTGTGTGGA ATTGTGAGCG ATAACAATT
       AAATACGAAG GCCGAGCATA CAACACACCT TAACACTCGC CTATTGTTAA
2201   TCACACAGGA AACAGCTATG ACCATGATTA CGCCAAGCTT GGAGCCTTT
       AGTGTGTCCT TTGTCGATAC TGGTACTAAT GCGGTTCGAA CCTCGGAAA
2251   TTTTTGGAGA TTTTCAACGT GAAAAAATTA TTATTCGCAA TTCCTTTAGT
       AAAAACCTCT AAAAGTTGCA CTTTTTTAAT AATAAGCGTT AAGGAAATCA
2301   TGTTCCTTTC TATGCGGCCC AGCCGGCCAT GGCCCAGGTC CAGTCGACAG
       ACAAGGAAAG ATACGCCGGG TCGGCCGGTA CCGGGTCCAG GTCAGCTGTC
2351   GTGGAGGCGG TTCAGGCGGA GGTGGCTCTG GCGGTGGCGG AAGTGCACTC
       CACCTCCGCC AAGTCCGCCT CCACCGAGAC CGCCACCGCC TTCACGTGAG
2401   ATCAAACGGC GGCCGCAGGT GCGCCGGTGC CGTATCCGGA TCCGCTGGAA
       TAGTTTGCCG CCGGCGTCCA CGCGGCCACG GCATAGGCCT AGGCGACCTT
2451   CCGCGTGCCG CATAGGCTGG CGGCGGCTCT GGTGGTGGTT CTGGTGGCGG
       GGCGCACGGC GTATCCGACC GCCGCCGAGA CCACCACCAA GACCACCGCC
2501   CTCTGAGGGT GGCGGCTCTG AGGGTGGCGG TTCTGAGGGT GGCGGCTCTG
       GAGACTCCCA CCGCCGAGAC TCCCACCGCC AAGACTCCCA CCGCCGAGAC
2551   AGGGTGGCGG TTCCGGTGGC GGCTCCGGTT CCGGTGATTT TGATTATGAA
       TCCCACCGCC AAGGCCACCG CCGAGGCCAA GGCCACTAAA ACTAATACTT
2601   AAAATGGCAA ACGCTAATAA GGGGGCTATG ACCGAAAATG CCGATGAAAA
       TTTTACCGTT TGCGATTATT CCCCCGATAC TGGCTTTTAC GGCTACTTTT
2651   CGCGCTACAC TCTGACGCTA AAGGCAAACT TGATTCTGTC GCTACTGATT
       GCGCGATGTC AGACTGCGAT TTCCGTTTGA ACTAAGACAC CGATGACTAA
2701   ACGGTGCTGC TATCGATGGT TTCATTGGTG ACGTTTCCGG CCTTGCTAAT
       TGCCACGACG ATAGCTACCA AAGTAACCAC TGCAAAGGCC GGAACGATTA
2751   GGTAATGGTG CTACTGGTGA TTTTGCTGGC TCTAATTCCC AAATGGCTCA
```

FIG. 13C  SEQ ID NO: 3 (cont.)
(nucleotides 1401-2800)

```
     CCATTACCAC GATGACCACT AAAACGACCG AGATTAAGGG TTTACCGAGT
2801 AGTCGGTGAC GGTGATAATT CACCTTTAAT GAATAATTTC CGTCAATATT
     TCAGCCACTG CCACTATTAA GTGGAAATTA CTTATTAAAG GCAGTTATAA
2851 TACCTTCTTT GCCTCAGTCG GTTAATGTC GCCCTTATGT CTTTGGCGCT
     ATGGAAGAAA CGGAGTCAGC CAACTTACAG CGGGAATACA GAAACCGCGA
2901 GGTAAACCAT ATGAATTTTC TATTGATTGT GACAAAATAA ACTTATTCCG
     CCATTTGGTA TACTTAAAAG ATAACTAACA CTGTTTTATT TGAATAAGGC
2951 TGGTGTCTTT GCGTTTCTTT TATATGTTGC CACCTTTATG TATGTATTTT
     ACCACAGAAA CGCAAAGAAA ATATACAACG GTGGAAATAC ATACATAAAA
3001 CGACGTTTGC TAACATACTG CGTAATAAGG AGTCTTAATA AGAATTCACT
     GCTGCAAACG ATTGTATGAC GCATTATTCC TCAGAATTAT TCTTAAGTGA
3051 GGCCGTCGTT TTACAACGTC GTGACTGGGA AAACCCTGGC GTTACCCAAC
     CCGGCAGCAA AATGTTGCAG CACTGACCCT TTTGGGACCG CAATGGGTTG
3101 TTAATCGCCT TGCAGCACAT CCCCCTTTCG CCAGCTGGCG TAATAGCGAA
     AATTAGCGGA ACGTCGTGTA GGGGGAAAGC GGTCGACCGC ATTATCGCTT
3151 GAGGCCCGCA CCGATCGCCC TTCCCAACAG TTGCGCAGCC TGAATGGCGA
     CTCCGGGCGT GGCTAGCGGG AAGGGTTGTC AACGCGTCGG ACTTACCGCT
3201 ATGGCGCCTG ATGCGGTATT TTCTCCTTAC GCATCTGTGC GGTATTTCAC
     TACCGCGGAC TACGCCATAA AAGAGGAATG CGTAGACACG CCATAAAGTG
3251 ACCGCATACG TCAAAGCAAC CATAGTACGC GCCCTGTAGC GGCGCATTAA
     TGGCGTATGC AGTTTCGTTG GTATCATGCG CGGGACATCG CCGCGTAATT
3301 GCCCGGCGGG TGTGGTGGTT ACGCGCAGCG TGACCGCTAC ACTTGCCAGC
     CGGGCCGCCC ACACCACCAA TGCGCGTCGC ACTGGCGATG TGAACGGTCG
3351 GCCCTAGCCC CCGCTCCTTT CGCTTTCTTC CCTTCCTTTC TCGCCACGTT
     CGGGATCGGG GGCGAGGAAA GCGAAAGAAG GGAAGGAAAG AGCGGTGCAA
3401 CGCCGGCTTT CCCCGTCAAG CTCTAAATCG GGGGCTCCCT TTAGGGTTCC
     GCGGCCGAAA GGGGCAGTTC GAGATTTAGC CCCCGAGGGA AATCCCAAGG
3451 GATTTAGTGC TTTACGGCAC CTCGACCCCA AAAAACTTGA TTTGGGTGAT
     CTAAATCACG AAATGCCGTG GAGCTGGGGT TTTTTGAACT AAACCCACTA
3501 GGTTCACGTA GTGGGCCATC GCCCTGATAG ACGGTTTTTC GTCCTTTGAC
     CCAAGTGCAT CACCCGGTAG CGGGACTATC TGCCAAAAAG CAGGAAACTG
3551 GTTCGAGTCC ACGTTCTTTA ATAGTGGACT CTTGTTCCAA ACTGGAACAA
     CAAGCTCAGG TGCAAGAAAT TATCACCTGA GAACAAGGTT TGACCTTGTT
3601 TACTCAACCC TATCTCGGGC TATTCTTTTG ATTTATAAGG GATTTTGCCG
     ATGAGTTGGG ATAGAGCCCG ATAAGAAAAC TAAATATTCC CTAAAACGGC
3651 ATTTCGGCCT ATTGGTTAAA AAATGAGCTG ATTTAACAAA AATTTAACGC
     TAAAGCCGGA TAACCAATTT TTTACTCGAC TAAATTGTTT TTAAATTGCG
3701 GAATTTTAAC AAAATATTAA CGTTTACAAT TTTATGGTGC AGTCTCAGTA
     CTTAAAATTG TTTTATAATT GCAAATGTTA AAATACCACG TCAGAGTCAT
3751 CAATCTGCTC TGATGCCGCA TAGTTAAGCC AGCCCCGACA CCCGCCAACA
     GTTAGACGAG ACTACGGCGT ATCAATTCGG TCGGGGCTGT GGGCGGTTGT
3801 CCCGCTGACG CGCCCTGACG GGCTTGTCTG CTCCCGGCAT CCGCTTACAG
     GGGCGACTGC GCGGGACTGC CCGAACAGAC GAGGGCCGTA GGCGAATGTC
3851 ACAAGCTGTG ACCGTCTCCG GGAGCTGCAT GTGTCAGAGG TTTTCACCGT
     TGTTCGACAC TGGCAGAGGC CCTCGACGTA CACAGTCTCC AAAAGTGGCA
3901 CATCACCGAA ACGCGCGA
     GTAGTGGCTT TGCGCGCT
```

FIG. 13D

SEQ ID NO: 3 (cont.)
(nucleotides 2801-3918)

Nucleotide Sequences pXP14

```
   1  GACGAAAGGG CCTCGTGATA CGCCTATTTT TATAGGTTAA TGTCATGATA
      CTGCTTTCCC GGAGCACTAT GCGGATAAAA ATATCCAATT ACAGTACTAT
  51  ATAATGGTTT CTTAGACGTC AGGTGGCACT TTTCGGGGAA ATGTGCGCGG
      TATTACCAAA GAATCTGCAG TCCACCGTGA AAAGCCCCTT TACACGCGCC
 101  AACCCCTATT TGTTTATTTT TCTAAATACA TTCAAATATG TATCCGCTCA
      TTGGGGATAA ACAAATAAAA AGATTTATGT AAGTTTATAC ATAGGCGAGT
 151  TGAGACAATA ACCCTGATAA ATGCTTCAAT AATATTGAAA AAGGAAGAGT
      ACTCTGTTAT TGGGACTATT TACGAAGTTA TTATAACTTT TTCCTTCTCA
 201  ATGAGTATTC AACATTTCCG TGTCGCCCTT ATTCCCTTTT TTGCGGCATT
      TACTCATAAG TTGTAAAGGC ACAGCGGGAA TAAGGGAAAA AACGCCGTAA
 251  TTGCCTTCCT GTTTTGCTC ACCCAGAAAC GCTGGTGAAA GTAAAAGATG
      AACGGAAGGA CAAAAACGAG TGGGTCTTTG CGACCACTTT CATTTTCTAC
 301  CTGAAGATCA GTTGGGTGCT CGAGTGGGTT ACATCGAACT GGATCTCAAC
      GACTTCTAGT CAACCCACGA GCTCACCCAA TGTAGCTTGA CCTAGAGTTG
 351  AGCGGTAAGA TCCTTGAGAG TTTTCGCCCC GAAGAACGTT TTCCAATGAT
      TCGCCATTCT AGGAACTCTC AAAAGCGGGG CTTCTTGCAA AAGGTTACTA
 401  GAGCACTTTT AAAGTTCTGC TATGTGGCGC GGTATTATCC CGTATTGACG
      CTCGTGAAAA TTTCAAGACG ATACACCGCG CCATAATAGG GCATAACTGC
 451  CCGGGCAAGA GCAACTCGGT CGCCGCATAC ACTATTCTCA GAATGACTTG
      GGCCCGTTCT CGTTGAGCCA GCGGCGTATG TGATAAGAGT CTTACTGAAC
 501  GTTGAGTACT CACCAGTCAC AGAAAAGCAT CTTACGGATG GCATGACAGT
      CAACTCATGA GTGGTCAGTG TCTTTTCGTA GAATGCCTAC CGTACTGTCA
 551  AAGAGAATTA TGCAGTGCTG CCATAACCAT GAGTGATAAC ACTGCGGCCA
      TTCTCTTAAT ACGTCACGAC GGTATTGGTA CTCACTATTG TGACGCCGGT
 601  ACTTACTTCT GACAACGATC GGAGGACCGA AGGAGCTAAC CGCTTTTTTG
      TGAATGAAGA CTGTTGCTAG CCTCCTGGCT TCCTCGATTG GCGAAAAAAC
 651  CACAACATGG GGGATCATGT AACTCGCCTT GATCGTTGGG AACCGGAGCT
      GTGTTGTACC CCCTAGTACA TTGAGCGGAA CTAGCAACCC TTGGCCTCGA
 701  GAATGAAGCC ATACCAAACG ACGAGCGTGA CACCACGATG CCTGTAGCAA
      CTTACTTCGG TATGGTTTGC TGCTCGCACT GTGGTGCTAC GGACATCGTT
 751  TGGCAACAAC GTTGCGCAAA CTATTAACTG GCGAACTACT TACTCTAGCT
      ACCGTTGTTG CAACGCGTTT GATAATTGAC CGCTTGATGA ATGAGATCGA
 801  TCCCGGCAAC AATTAATAGA CTGGATGGAG GCGGATAAAG TTGCAGGACC
      AGGGCCGTTG TTAATTATCT GACCTACCTC CGCCTATTTC AACGTCCTGG
 851  ACTTCTGCGC TCGGCCCTTC CGGCTGGCTG GTTTATTGCT GATAAATCTG
      TGAAGACGCG AGCCGGGAAG GCCGACCGAC CAAATAACGA CTATTTAGAC
 901  GAGCCGGTGA GCGTGGGTCT CGCGGTATCA TTGCAGCACT GGGGCCAGAT
      CTCGGCCACT CGCACCCAGA GCGCCATAGT AACGTCGTGA CCCCGGTCTA
 951  GGTAAGCCCT CCCGTATCGT AGTTATCTAC ACGACGGGGA GTCAGGCAAC
      CCATTCGGGA GGGCATAGCA TCAATAGATG TGCTGCCCCT CAGTCCGTTG
1001  TATGGATGAA CGAAATAGAC AGATCGCTGA GATAGGTGCC TCACTGATTA
      ATACCTACTT GCTTTATCTG TCTAGCGACT CTATCCACGG AGTGACTAAT
1051  AGCATTGGTA ACTGTCAGAC CAAGTTACT CATATATACT TTAGATTGAT
      TCGTAACCAT TGACAGTCTG GTTCAAATGA GTATATATGA AATCTAACTA
1101  TTAAAACTTC ATTTTAATT TAAAGGATC TAGGTGAAGA TCCTTTTTGA
      AATTTTGAAG TAAAAATTAA ATTTTCCTAG ATCCACTTCT AGGAAAAACT
1151  TAATCTCATG ACCAAAATCC CTTAACGTGA GTTTTCGTTC CACTGAGCGT
      ATTAGAGTAC TGGTTTTAGG GAATTGCACT CAAAAGCAAG GTGACTCGCA
1201  CAGACCCCGT AGAAAAGATC AAAGGATCTT CTTGAGATCC TTTTTTTCTG
      GTCTGGGGCA TCTTTTCTAG TTTCCTAGAA GAACTCTAGG AAAAAAAGAC
```

FIG. 14B

SEQ ID NO: 4
(nucleotides 1-1250)

```
1251  CGCGTAATCT GCTGCTTGCA AACAAAAAAA CCACCGCTAC CAGCGGTGGT
      GCGCATTAGA CGACGAACGT TTGTTTTTTT GGTGGCGATG GTCGCCACCA
1301  TTGTTTGCCG GATCAAGAGC TACCAACTCT TTTTCCGAAG GTAACTGGCT
      AACAAACGGC CTAGTTCTCG ATGGTTGAGA AAAAGGCTTC CATTGACCGA
1351  TCAGCAGAGC GCAGATACCA AATACTGTCC TTCTAGTGTA GCCGTAGTTA
      AGTCGTCTCG CGTCTATGGT TTATGACAGG AAGATCACAT CGGCATCAAT
1401  GGCCACCACT TCAAGAACTC TGTAGCACCG CCTACATACC TCGCTCTGCT
      CCGGTGGTGA AGTTCTTGAG ACATCGTGGC GGATGTATGG AGCGAGACGA
1451  AATCCTGTTA CCAGTGGCTG CTGCCAGTGG CGATAAGTCG TGTCTTACCG
      TTAGGACAAT GGTCACCGAC GACGGTCACC GCTATTCAGC ACAGAATGGC
1501  GGTTGGACTC AAGACGATAG TTACCGGATA AGGCGCAGCG GTCGGGCTGA
      CCAACCTGAG TTCTGCTATC AATGGCCTAT TCCGCGTCGC CAGCCCGACT
1551  ACGGGGGGTT CGTGCATACA GCCCAGCTTG GAGCGAACGA CCTACACCGA
      TGCCCCCCAA GCACGTATGT CGGGTCGAAC CTCGCTTGCT GGATGTGGCT
1601  ACTGAGATAC CTACAGCGTG AGCTATGAGA AAGCGCCACG CTTCCCGAAG
      TGACTCTATG GATGTCGCAC TCGATACTCT TTCGCGGTGC GAAGGGCTTC
1651  GGAGAAAGGC GGACAGGTAT CCGGTAAGCG GCAGGGTCGG AACAGGAGAG
      CCTCTTTCCG CCTGTCCATA GGCCATTCGC CGTCCCAGCC TTGTCCTCTC
1701  CGCACGAGGG AGCTTCCAGG GGGAAACGCC TGGTATCTTT ATAGTCCTGT
      GCGTGCTCCC TCGAAGGTCC CCCTTTGCGG ACCATAGAAA TATCAGGACA
1751  CGGGTTTCGC CACCTCTGAC TTGAGCGTCG ATTTTTGTGA TGCTCGTCAG
      GCCCAAAGCG GTGGAGACTG AACTCGCAGC TAAAAACACT ACGAGCAGTC
1801  GGGGGCGGAG CCTATGGAAA AACGCCAGCA ACGCGGCCTT TTTACGGTTC
      CCCCCGCCTC GGATACCTTT TTGCGGTCGT TGCGCCGGAA AAATGCCAAG
1851  CTGGCCTTTT GCTGGCCTTT TGCTCACATG TTCTTTCCTG CGTTATCCCC
      GACCGGAAAA CGACCGGAAA ACGAGTGTAC AAGAAAGGAC GCAATAGGGG
1901  TGATTCTGTG GATAACCGTA TTACCGCCTT TGAGTGAGCT GATACCGCTC
      ACTAAGACAC CTATTGGCAT AATGGCGGAA ACTCACTCGA CTATGGCGAG
1951  GCCGCAGCCG AACGACCGAG CGCAGCGAGT CAGTGAGCGA GGAAGCGGAA
      CGGCGTCGGC TTGCTGGCTC GCGTCGCTCA GTCACTCGCT CCTTCGCCTT
2001  GAGCGCCCAA TACGCAAACC GCCTCTCCCC GCGCGTTGGC CGATTCATTA
      CTCGCGGGTT ATGCGTTTGG CGGAGAGGGG CGCGCAACCG GCTAAGTAAT
2051  ATGCAGCTGG CACGACAGGT TTCCCGACTG GAAAGCGGGC AGTGAGCGCA
      TACGTCGACC GTGCTGTCCA AAGGGCTGAC CTTTCGCCCG TCACTCGCGT
2101  ACGCAATTAA TGTGAGTTAG CTCACTCATT AGGCACCCCA GGCTTTACAC
      TGCGTTAATT ACACTCAATC GAGTGAGTAA TCCGTGGGGT CCGAAATGTG
2151  TTTATGCTTC CGGCTCGTAT GTTGTGTGGA ATTGTGAGCG GATAACAATT
      AAATACGAAG GCCGAGCATA CAACACACCT TAACACTCGC CTATTGTTAA
2201  TCACACAGGA AACAGCTATG ACCATGATTA CGCCAAGCTT GCATGCAAAT
      AGTGTGTCCT TTGTCGATAC TGGTACTAAT GCGGTTCGAA CGTACGTTTA
2251  TCTATTTCAA GGAGACAGTC ATAATGAAAT ACCTATTGCC TACGGCAGCC
      AGATAAAGTT CCTCTGTCAG TATTACTTTA TGGATAACGG ATGCCGTCGG
2301  GCTGGATTGT TATTACTCGC GGCCCAGCCG GCCATGGCCC AGGTGCAGCT
      CGACCTAACA ATAATGAGCG CCGGGTCGGC CGGTACCGGG TCCACGTCGA
2351  GCAGGTCGGC CTCGAGATCA AACGGGCGGC CGCAGGTGCG CCGGTGCCGT
      CGTCCAGCCG GAGCTCTAGT TTGCCCGCCG GCGTCCACGC GGCCACGGCA
2401  ATCCAGATCC GCTGGAACCG CGTGGGGCCG CAAGCGCTTG GAGCCACCCG
      TAGGTCTAGG CGACCTTGGC GCACCCCGGC GTTCGCGAAC CTCGGTGGGC
2451  CAGTTCGAAA AATAATAAGG ATCCGAATTC ACTGGCCGTC GTTTTACAAC
      GTCAAGCTTT TTATTATTCC TAGGCTTAAG TGACCGGCAG CAAAATGTTG
```

FIG. 14C

SEQ ID NO: 4 (cont.)
(nucleotides 1251-2500)

```
2501  GTCGTGACTG GGAAAACCCT GGCGTTACCC AACTTAATCG CCTTGCAGCA
      CAGCACTGAC CCTTTTGGGA CCGCAATGGG TTGAATTAGC GGAACGTCGT
2551  CATCCCCCTT TCGCCAGCTG GCGTAATAGC GAAGAGGCCC GCACCGATCG
      GTAGGGGGAA AGCGGTCGAC CGCATTATCG CTTCTCCGGG CGTGGCTAGC
2601  CCCTTCCCAA CAGTTGCGCA GCCTGAATGG CGAATGGCGC CTGATGCGGT
      GGGAAGGGTT GTCAACGCGT CGGACTTACC GCTTACCGCG GACTACGCCA
2651  ATTTTCTCCT TACGCATCTG TGCGGTATTT CACACCGCAT ACGTCAAAGC
      TAAAAGAGGA ATGCGTAGAC ACGCCATAAA GTGTGGCGTA TGCAGTTTCG
2701  AACCATAGTA CGCGCCCTGT AGCGGCGCAT TAAGCCCGGC GGGTGTGGTG
      TTGGTATCAT GCGCGGGACA TCGCCGCGTA ATTCGGGCCG CCCACACCAC
2751  GTTACGCGCA GCGTGACCGC TACACTTGCC AGCGCCCTAG CCCCCGCTCC
      CAATGCGCGT CGCACTGGCG ATGTGAACGG TCGCGGGATC GGGGGCGAGG
2801  TTTCGCTTTC TTCCCTTCCT TTCTCGCCAC GTTCGCCGGC TTTCCCCGTC
      AAAGCGAAAG AAGGGAAGGA AAGAGCGGTG CAAGCGGCCG AAAGGGGCAG
2851  AAGCTCTAAA TCGGGGGCTC CCTTTAGGGT TCCGATTTAG TGCTTTACGG
      TTCGAGATTT AGCCCCCGAG GGAAATCCCA AGGCTAAATC ACGAAATGCC
2901  CACCTCGACC CCAAAAAACT TGATTTGGGT GATGGTTCAC GTAGTGGGCC
      GTGGAGCTGG GGTTTTTTGA ACTAAACCCA CTACCAAGTG CATCACCCGG
2951  ATCGCCCTGA TAGACGGTTT TTCGTCCTTT GACGTTCGAG TCCACGTTCT
      TAGCGGGACT ATCTGCCAAA AAGCAGGAAA CTGCAAGCTC AGGTGCAAGA
3001  TTAATAGTGG ACTCTTGTTC CAAACTGGAA CAATACTCAA CCCTATCTCG
      AATTATCACC TGAGAACAAG GTTTGACCTT GTTATGAGTT GGGATAGAGC
3051  GGCTATTCTT TTGATTTATA AGGGATTTTG CCGATTTCGG CCTATTGGTT
      CCGATAAGAA AACTAAATAT TCCCTAAAAC GGCTAAAGCC GGATAACCAA
3101  AAAAAATGAG CTGATTTAAC AAAAATTTAA CGCGAATTTT AACAAAATAT
      TTTTTTACTC GACTAAATTG TTTTTAAATT GCGCTTAAAA TTGTTTTATA
3151  TAACGTTTAC AATTTTATGG TGCAGTCTCA GTACAATCTG CTCTGATGCC
      ATTGCAAATG TTAAAATACC ACGTCAGAGT CATGTTAGAC GAGACTACGG
3201  GCATAGTTAA GCCAGCCCCG ACACCCGCCA ACACCCGCTG ACGCGCCCTG
      CGTATCAATT CGGTCGGGGC TGTGGGCGGT TGTGGGCGAC TGCGCGGGAC
3251  ACGGGCTTGT CTGCTCCCGG CATCCGCTTA CAGACAAGCT GTGACCGTCT
      TGCCCGAACA GACGAGGGCC GTAGGCGAAT GTCTGTTCGA CACTGGCAGA
3301  CCGGGAGCTG CATGTGTCAG AGGTTTTCAC CGTCATCACC GAAACGCGCG
      GGCCCTCGAC GTACACAGTC TCCAAAAGTG GCAGTAGTGG CTTTGCGCGC
3351  A
      T
```

SEQ ID NO: 4 (cont.)
(nucleotides 2501-3351)

*FIG. 14D* cDNA primers

| VLK-c | CTGGATGGTGGGAAGATGGA | SEQ ID NO: 5 |
|---|---|---|
| VLL-c | TCAGAGGAAGGAAACAGGGT | SEQ ID NO: 6 |
| IgG1-c | CTTACAACCACAATCCCTGGGCACAATTTT | SEQ ID NO: 7 |
| IgG2a-c | CTTTGTGGGCCCTCTGGGCTCAAT | SEQ ID NO: 8 |
| IgG2-b | TGAAATGGGCCCGCTGGGCTCAAG | SEQ ID NO: 9 |
| IgG3-c | GGGCTTGGGTATTCTAGGCTCGAT | SEQ ID NO: 10 |

VH forward primers without restriction sites

| M-VH1 | GAGGTGCAGCTTCAGGAGTCAGG | SEQ ID NO: 11 |
|---|---|---|
| M-VH2 | CAGGTGCAGCTGAAGGAGTCAGG | SEQ ID NO: 12 |
| M-VH3 | GAGGTCCAGCTGCAACAGTCTGG | SEQ ID NO: 13 |
| M-VH4 | GAGGTTCAGCTGCAGCAGTCTGG | SEQ ID NO: 14 |
| M-VH5 | CAGGTCCAACTGCAGCAGCCTGG | SEQ ID NO: 15 |
| M-VH6 | CAGGTTCAGCTGCAGCAGTCTGG | SEQ ID NO: 16 |
| M-VH7 | GAGGTGAAGCTGGTGGAGTCTGG | SEQ ID NO: 17 |
| M-VH8 | GAGGTGAAGCTGGTGGAATCTGG | SEQ ID NO: 18 |
| M-VH9 | GAGGTTCAGCTTCAGCAGTCTGG | SEQ ID NO: 19 |

VH backward primers without restriction sites

| M-JH1 | TGAGGAGACGGTGACCGTGGTCCC | SEQ ID NO: 20 |
|---|---|---|
| M-JH2 | TGAGGAGACTGTGAGAGTGGTGCC | SEQ ID NO: 21 |
| M-JH3 | TGCAGAGACAGTGACCAGAGTCCC | SEQ ID NO: 22 |
| M-JH4 | TGAGGAGACGGTGACTGAGGTTCC | SEQ ID NO: 23 |

VL forward primer without restriction sites

| M-VK1 | GACATTGTGATGACACAGTCTCC | SEQ ID NO: 24 |
|---|---|---|
| M-VK2 | GATGTTGTGATGACCCAAACTCC | SEQ ID NO: 25 |
| M-VK3 | GATATCCAGATGACACAGACTCC | SEQ ID NO: 26 |
| M-VK4 | CAAATTGTTCTCACCCAGTCTCC | SEQ ID NO: 27 |
| M-VL1 | CAGGCTGTTGTGACTCAGGAATC | SEQ ID NO: 28 |

VL backward primers without restriction sites

| M-JK1 | TTTGATTTCCAGCTTGGTGCCTCC | SEQ ID NO: 29 |
|---|---|---|
| M-JK2 | TTTTATTTCCAGCTTGGTCCCCCC | SEQ ID NO: 30 |
| M-JK3 | TTTCAGCTCCAGCTTGGTCCCAGC | SEQ ID NO: 31 |
| M-JL1 | ACCTAGGACAGTGACCTTGGTTCC | SEQ ID NO: 32 |

*FIG. 15A*

VH forward primers with restriction sites

| MVH1 SfiI | GTCCTCGCAACTGCGGCCCAGCCGGCCATGGCCGAGGTGCAGCTTCAGGAGTCAGG | SEQ ID NO: 33 |
|---|---|---|
| MVH2 SfiI | GTCCTCGCAACTGCGGCCCAGCCGGCCATGGCCCAGGTGCAGCTGAAGGAGTCAGG | SEQ ID NO: 34 |
| MVH3 SfiI | GTCCTCGCAACTGCGGCCCAGCCGGCCATGGCCGAGGTCCAGCTGCAACAGTCTGG | SEQ ID NO: 35 |
| MVH4 SfiI | GTCCTCGCAACTGCGGCCCAGCCGGCCATGGCCGAGGTTCAGCTGCAGCAGTCTGG | SEQ ID NO: 36 |
| MVH5 SfiI | GTCCTCGCAACTGCGGCCCAGCCGGCCATGGCCCAGGTCCAACTGCAGCAGCCTGG | SEQ ID NO: 37 |
| MVH6 SfiI | GTCCTCGCAACTGCGGCCCAGCCGGCCATGGCCCAGGTTCAGCTGCAGCAGTCTGG | SEQ ID NO: 38 |
| MVH7 SfiI | GTCCTCGCAACTGCGGCCCAGCCGGCCATGGCCGAGGTGAAGCTGGTGGAGTCTGG | SEQ ID NO: 39 |
| MVH8 SfiI | GTCCTCGCAACTGCGGCCCAGCCGGCCATGGCCGAGGTGAAGCTGGTGGAATCTGG | SEQ ID NO: 40 |
| MVH9 SfiI | GTCCTCGCAACTGCGGCCCAGCCGGCCATGGCCGAGGTTCAGCTTCAGCAGTCTGG | SEQ ID NO: 41 |

VH backward primers with restriction sites

| MJH1 SalI | GAGTCATTCTCGTGTCGACACGGTGACCGTGGTCCC | SEQ ID NO: 42 |
|---|---|---|
| MJH2 SalI | GAGTCATTCTCGTGTCGACACTGTGAGAGTGGTGCC | SEQ ID NO: 43 |
| MJH3 SalI | GAGTCATTCTCGTGTCGACACAGTGACCAGAGTCCC | SEQ ID NO: 44 |
| MJH4 SalI | GAGTCATTCTCGTGTCGACACGGTGACTGAGGTTCC | SEQ ID NO: 45 |

VL forward primers with restriction sites

| MVK1 ApaL1 | TGAGCACACAGTGCACTCGACATTGTGATGACACAGTCTCC | SEQ ID NO: 46 |
|---|---|---|
| MVK2 ApaL1 | TGAGCACACAGTGCACTCGATGTTGTGATGACCCAAACTCC | SEQ ID NO: 47 |
| MVK3 ApaL1 | TGAGCACACAGTGCACTCGATATCCAGATGACACAGACTCC | SEQ ID NO: 48 |
| MVK4 ApaL1 | TGAGCACACAGTGCACTCCAAATTGTTCTCACCCAGTCTCC | SEQ ID NO: 49 |
| MVL1 ApaL1 | TGAGCACACAGTGCACTCCAGGCTGTTGTGACTCAGGAATC | SEQ ID NO: 50 |

VL backward primers with restriction sites

| M-JK1 Not1 | GAGTCATTCTCGACTTGCGGCCGCTTTGATTTCCAGCTTGGTGCCTCC | SEQ ID NO: 51 |
|---|---|---|
| M-JK2 Not1 | GAGTCATTCTCGACTTGCGGCCGCTTTTATTTCCAGCTTGGTCCCCC | SEQ ID NO: 52 |
| M-JK3 Not1 | GAGTCATTCTCGACTTGCGGCCGCTTTCAGCTCCAGCTTGGTCCCAGC | SEQ ID NO: 53 |
| M-JL1 Not1 | GAGTCATTCTCGACTTGCGGCCGCACCTAGGACAGTGACCTTGGTTCC | SEQ ID NO: 54 |

*FIG. 15B*

| POLYPEPTIDE | SEQ ID NO. | PROTEIN SEQUENCE |
|---|---|---|
| scFv1 | 1 | 1   QVQLKESGAELVKPGASVKLSCTASGFNIKDYYMHWVKQRTEQGLEWIGR<br>51  IDPEDGETKYAPKFQGKATITADTSSNTAYLQLSSLTSEDTAVYYCARSY<br>101 DYAMDYWGQGTTVTVSTGGGSGGGGSGGGGSALQIVLTQSPALMSASPG<br>151 EKVTMTCSASSSVSYMHWYQQKSGTSPKRWIYDTSKLASGVPARFSGSGS<br>201 GTSYSLTISSMEAEDAATYYCQQWSSNPLTFGAGTKLELKAAAGAPVPYP<br>251 DPLEPRGAASAWSHPQFEK* |

| scFv DNA | SEQ ID NO. | NUCLEOTIDE SEQUENCE |
|---|---|---|
| scFv1 | 2 | 1   CAGGTGCAGCTGAAGGAGTCAGGACCTGAAGCCAGGGCCCTCAGTGTCCTGCACAG<br>71  CTTCTGGCTTCAACATTAAAGACTACTATATGCACTGGGTGAAGCAGAGGACTGAACAGGGCCTGGAGTG<br>141 GATTGGAAGGATTGATCCTGAGGATGGTGAAACTAAATATGCCCCGAAATTCCAGGGCAAGGCCACTATA<br>211 ACAGCAGACACATCCTCCAACACAGCCTACCTGCAGCTCAGCAGCCTGACATCTGAGGACACGGTCGTCT<br>281 ATTACTGTGCTAGATCCTACGACTATGCTATGGACTACTGGGGTCAAGGGACCACGGTCACCGTGTCGAC<br>351 AGGTGGAGGCGGTTCAGGCGGAGGTGGCTCTGGCGGTGGCGGAAGTGCACTCCAAATTGTTCTCACCCAG<br>421 TCTCCAGCACTCATGTCTGCATCTCCAGGGGAGAAGGTCACCATGACCTGCAGTGCCAGCTCAAGTGTAA<br>491 GTTACATGCACTGGTACCAGCAGAAGTCAGGCACCTCCCCCAAAAGATGGATTTATGACACATCCAAACT<br>561 GGCTTCTGGAGTCCCTGCTCGCTTCAGTGGCAGTGGGTCTGGGACCTCTTACTCTCTCACAATCAGCAGC<br>631 ATGGAGGCTGAAGATGCTGCCACTTATTACTGCCAGCAGTGGCGCGGTGCCGGGTATCCGGTTCGGTGCTG<br>701 GGACCAAGCTGGAGCTGAAAGCGGCCGCACCCGCCGAGTTCGAAAAATAA<br>771 GGCCCGCAAGCGCTTGGAGCCAAGCGCTTGGAGCCACCCGCCGAGTTCGAAAAATAA |

*FIG. 16*

SEQUENCE LISTING

<160> NUMBER OF SEQ ID NOS: 55

<210> SEQ ID NO 1
<211> LENGTH: 269
<212> TYPE: PRT
<213> ORGANISM: Mus sp.

```
<400> SEQUENCE: 1

Gln Val Gln Leu Lys Glu Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Ser Tyr Asp Tyr Ala Met Asp Tyr Trp Gly Gln Gly Thr Thr
            100                 105                 110

Val Thr Val Ser Thr Gly Gly Gly Gly Ser Gly Gly Gly Ser Gly
        115                 120                 125

Gly Gly Gly Ser Ala Leu Gln Ile Val Leu Thr Gln Ser Pro Ala Leu
    130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala Arg Phe Ser Gly Ser Gly Ser Gly Thr Ser Tyr Ser Leu Thr Ile
        195                 200                 205

Ser Ser Met Glu Ala Glu Asp Ala Ala Thr Tyr Tyr Cys Gln Gln Trp
    210                 215                 220

Ser Ser Asn Pro Leu Thr Phe Gly Ala Gly Thr Lys Leu Glu Leu Lys
225                 230                 235                 240

Ala Ala Ala Gly Ala Pro Val Pro Tyr Pro Asp Pro Leu Glu Pro Arg
                245                 250                 255

Gly Ala Ala Ser Ala Trp Ser His Pro Gln Phe Glu Lys
            260                 265

<210> SEQ ID NO 2
<211> LENGTH: 810
<212> TYPE: DNA
<213> ORGANISM: Mus sp.

<400> SEQUENCE: 2
caggtgcagc tgaaggagtc aggggcagag cttgtgaagc caggggcctc agtcaagttg      60
tcctgcacag cttctggctt caacattaaa gactactata tgcactgggt gaagcagagg     120
actgaacagg gcctggagtg gattggaagg attgatcctg aggatggtga aactaaatat     180
gccccgaaat tccagggcaa ggccactata acagcagaca catcctccaa cacagcctac     240
ctgcagctca gcagcctgac atctgaggac actgccgtct attactgtgc tagatcctac     300
gactatgcta tggactactg gggtcaaggg accacggtca ccgtgtcgac aggtggaggc     360
ggttcaggcg gaggtggctc tggcggtggc ggaagtgcac tccaaattgt tctcacccag     420
tctccagcac tcatgtctgc atctccaggg gagaaggtca ccatgacctg cagtgccagc     480
tcaagtgtaa gttacatgca ctggtaccag cagaagtcag gcacctcccc caaaagatgg     540
```

-continued

| | |
|---|---|
| atttatgaca catccaaact ggcttctgga gtccctgctc gcttcagtgg cagtgggtct | 600 |
| gggacctctt actctctcac aatcagcagc atggaggctg aagatgctgc cacttattac | 660 |
| tgccagcagt ggagtagtaa cccactcacg ttcggtgctg ggaccaagct ggagctgaaa | 720 |
| gcggccgcag gtgcgccggt gccgtatcca gatccgctgg aaccgcgtgg ggccgcaagc | 780 |
| gcttggagcc acccgcagtt cgaaaaataa | 810 |

<210> SEQ ID NO 3
<211> LENGTH: 3918
<212> TYPE: DNA
<213> ORGANISM: Mus sp.

<400> SEQUENCE: 3

| | |
|---|---|
| gacgaaaggg cctcgtgata cgcctatttt tataggttaa tgtcatgata ataatggttt | 60 |
| cttagacgtc aggtggcact tttcggggaa atgtgcgcgg aaccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attcccttt | 240 |
| ttgcggcatt ttgccttcct gtttttgctc acccagaaac gctggtgaaa gtaaaagatg | 300 |
| ctgaagatca gttgggtgct cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga caccacgatg cctgtagcaa tggcaacaac gttgcgcaaa ctattaactg | 780 |
| gcgaactact tactctagct tcccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc attttaatt taaaaggatc taggtgaaga | 1140 |
| tccttttga taatctcatg accaaaatcc cttaacgtga gttttcgttc cactgagcgt | 1200 |
| cagaccccgt agaaaagatc aaaggatctt cttgagatcc ttttttctg cgcgtaatct | 1260 |
| gctgcttgca acaaaaaaa ccaccgctac cagcggtggt ttgtttgccg gatcaagagc | 1320 |
| taccaactct tttccgaag gtaactggct tcagcagagc gcagatacca aatactgtcc | 1380 |
| ttctagtgta gccgtagtta ggccaccact tcaagaactc tgtagcaccg cctacatacc | 1440 |
| tcgctctgct aatcctgtta ccagtggctg ctgccagtgg cgataagtcg tgtcttaccg | 1500 |
| ggttggactc aagacgatag ttaccggata aggcgcagcg gtcgggctga acggggggtt | 1560 |
| cgtgcataca gcccagcttg gagcgaacga cctacaccga actgagatac ctacagcgtg | 1620 |
| agctatgaga aagcgccacg cttcccgaag ggagaaaggc ggacaggtat ccggtaagcg | 1680 |
| gcagggtcgg aacaggagag cgcacgaggg agcttccagg gggaaacgcc tggtatcttt | 1740 |
| atagtcctgt cgggtttcgc cacctctgac ttgagcgtcg atttttgtga tgctcgtcag | 1800 |
| gggggcggag cctatggaaa aacgccagca acgcggcctt tttacggttc ctggccttt | 1860 |

```
gctggccttt tgctcacatg ttctttcctg cgttatcccc tgattctgtg gataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcacccca ggctttacac tttatgcttc    2160
cggctcgtat gttgtgtgga attgtgagcg gataacaatt tcacacagga acagctatg     2220 accatgatta cgccaagctt tggagccttt ttttggaga ttttcaacgt gaaaaaatta     2280
ttattcgcaa ttcctttagt tgttcctttc tatgcggccc agccggccat ggcccaggtc    2340
cagtcgacag gtggaggcgg ttcaggcgga ggtggctctg gcggtggcgg aagtgcactc    2400
atcaaacggc ggccgcaggt gcgccggtgc cgtatccgga tccgctggaa ccgcgtgccg    2460
cataggctgg cggcggctct ggtggtggtt ctggtggcgg ctctgagggt ggcggctctg    2520
agggtggcgg ttctgagggt ggcggctctg agggtggcgg ttccggtggc ggctccggtt    2580
ccggtgattt tgattatgaa aaatggcaa acgctaataa gggggctatg accgaaaatg     2640
ccgatgaaaa cgcgctacag tctgacgcta aaggcaaact tgattctgtc gctactgatt    2700
acggtgctgc tatcgatggt ttcattggtg acgtttccgg ccttgctaat ggtaatggtg    2760
ctactggtga ttttgctggc tctaattccc aaatggctca agtcggtgac ggtgataatt    2820
cacctttaat gaataatttc cgtcaatatt taccttcttt gcctcagtcg gttgaatgtc    2880
gcccttatgt ctttggcgct ggtaaaccat atgaattttc tattgattgt gacaaaataa    2940
acttattccg tggtgtcttt gcgtttcttt tatatgttgc cacctttatg tatgtatttt    3000
cgacgtttgc taacatactg cgtaataagg agtcttaata agaattcact ggccgtcgtt    3060
ttacaacgtc gtgactggga aaaccctggc gttacccaac ttaatcgcct tgcagcacat    3120
ccccctttcg ccagctggcg taatagcgaa gaggcccgca ccgatcgccc ttcccaacag    3180
ttgcgcagcc tgaatggcga atggcgcctg atgcggtatt ttctccttac gcatctgtgc    3240
ggtatttcac accgcatacg tcaaagcaac catagtacgc gccctgtagc ggcgcattaa    3300
gcccggcggg tgtggtggtt acgcgcagcg tgaccgctac acttgccagc gccctagccc    3360
ccgctccttt cgctttcttc ccttcctttc tcgccacgtt cgccggcttt ccccgtcaag    3420
ctctaaatcg ggggctccct ttagggttcc gatttagtgc tttacggcac ctcgacccca    3480
aaaaacttga tttgggtgat ggttcacgta gtgggccatc gccctgatag acggtttttc    3540
gtcctttgac gttcgagtcc acgttcttta atagtggact cttgttccaa actggaacaa    3600
tactcaaccc tatctcgggc tattcttttg atttataagg gattttgccg atttcggcct    3660
attggttaaa aaatgagctg atttaacaaa aatttaacgc gaattttaac aaaatattaa    3720
cgtttacaat tttatggtgc agtctcagta caatctgctc tgatgccgca tagttaagcc    3780
agccccgaca cccgccaaca cccgctgacg cgccctgacg gcttgtctg ctcccggcat     3840 ccgcttacag acaagctgtg accgtctccg ggagctgcat gtgtcagagg ttttcaccgt    3900
catcaccgaa acgcgcga                                                  3918
```

<210> SEQ ID NO 4
<211> LENGTH: 3351
<212> TYPE: DNA
<213> ORGANISM: Mus sp.

<400> SEQUENCE: 4

-continued

| | | | | | |
|---|---|---|---|---|---|
| gacgaaaggg | cctcgtgata | cgcctatttt | tataggttaa | tgtcatgata | ataatggttt | 60 |
| cttagacgtc | aggtggcact | tttcggggaa | atgtgcgcgg | aacccctatt | tgtttatttt | 120 |
| tctaaataca | ttcaaatatg | tatccgctca | tgagacaata | accctgataa | atgcttcaat | 180 |
| aatattgaaa | aaggaagagt | atgagtattc | aacatttccg | tgtcgccctt | attccctttt | 240 |
| ttgcggcatt | ttgccttcct | gtttttgctc | acccagaaac | gctggtgaaa | gtaaaagatg | 300 |
| ctgaagatca | gttgggtgct | cgagtgggtt | acatcgaact | ggatctcaac | agcggtaaga | 360 |
| tccttgagag | ttttcgcccc | gaagaacgtt | ttccaatgat | gagcactttt | aaagttctgc | 420 |
| tatgtggcgc | ggtattatcc | cgtattgacg | ccgggcaaga | gcaactcggt | cgccgcatac | 480 |
| actattctca | gaatgacttg | gttgagtact | caccagtcac | agaaaagcat | cttacggatg | 540 |
| gcatgacagt | aagagaatta | tgcagtgctg | ccataaccat | gagtgataac | actgcggcca | 600 |
| acttacttct | gacaacgatc | ggaggaccga | aggagctaac | cgcttttttg | cacaacatgg | 660 |
| gggatcatgt | aactcgcctt | gatcgttggg | aaccggagct | gaatgaagcc | ataccaaacg | 720 |
| acgagcgtga | caccacgatg | cctgtagcaa | tggcaacaac | gttgcgcaaa | ctattaactg | 780 |
| gcgaactact | tactctagct | tcccggcaac | aattaataga | ctggatggag | gcggataaag | 840 |
| ttgcaggacc | acttctgcgc | tcggcccttc | cggctggctg | gtttattgct | gataaatctg | 900 |
| gagccggtga | gcgtgggtct | cgcggtatca | ttgcagcact | ggggccagat | ggtaagccct | 960 |
| cccgtatcgt | agttatctac | acgacgggga | gtcaggcaac | tatggatgaa | cgaaatagac | 1020 |
| agatcgctga | gataggtgcc | tcactgatta | agcattggta | actgtcagac | caagtttact | 1080 |
| catatatact | ttagattgat | ttaaaacttc | attttaatt | taaaaggatc | taggtgaaga | 1140 |
| tcctttttga | taatctcatg | accaaaatcc | cttaacgtga | gttttcgttc | cactgagcgt | 1200 |
| cagacccccg | agaaaagatc | aaaggatctt | cttgagatcc | tttttttctg | cgcgtaatct | 1260 |
| gctgcttgca | aacaaaaaaa | ccaccgctac | cagcggtggt | ttgtttgccg | gatcaagagc | 1320 |
| taccaactct | ttttccgaag | gtaactggct | tcagcagagc | gcagatacca | aatactgtcc | 1380 |
| ttctagtgta | gccgtagtta | ggccaccact | tcaagaactc | tgtagcaccg | cctacatacc | 1440 |
| tcgctctgct | aatcctgtta | ccagtggctg | ctgccagtgg | cgataagtcg | tgtcttaccg | 1500 |
| ggttggactc | aagacgatag | ttaccggata | aggcgcagcg | gtcgggctga | acggggggtt | 1560 |
| cgtgcataca | gcccagcttg | gagcgaacga | cctacaccga | actgagatac | ctacagcgtg | 1620 |
| agctatgaga | aagcgccacg | cttcccgaag | ggagaaaggc | ggacaggtat | ccggtaagcg | 1680 |
| gcagggtcgg | aacaggagag | cgcacgaggg | agcttccagg | gggaaacgcc | tggtatcttt | 1740 |
| atagtcctgt | cgggtttcgc | cacctctgac | ttgagcgtcg | atttttgtga | tgctcgtcag | 1800 |
| gggggcggag | cctatggaaa | aacgccagca | acgcggcctt | tttacggttc | ctggccttt | 1860 |
| gctggccttt | tgctcacatg | ttctttcctg | cgttatcccc | tgattctgtg | gataaccgta | 1920 |
| ttaccgcctt | tgagtgagct | gataccgctc | gccgcagccg | aacgaccgag | cgcagcgagt | 1980 |
| cagtgagcga | ggaagcggaa | gagcgcccaa | tacgcaaacc | gcctctcccc | gcgcgttggc | 2040 |
| cgattcatta | atgcagctgg | cacgacaggt | ttcccgactg | gaaagcgggc | agtgagcgca | 2100 |
| acgcaattaa | tgtgagttag | ctcactcatt | aggcacccca | ggctttacac | tttatgcttc | 2160 |
| cggctcgtat | gttgtgtgga | attgtgagcg | gataacaatt | tcacacagga | aacagctatg | 2220 |
| accatgatta | cgccaagctt | gcatgcaaat | tctatttcaa | ggagacagtc | ataatgaaat | 2280 |
| acctattgcc | tacggcagcc | gctggattgt | tattactcgc | ggcccagccg | gccatggccc | 2340 |
| aggtgcagct | gcaggtcggc | ctcgagatca | acgggcggc | cgcaggtgcg | ccggtgccgt | 2400 |

```
atccagatcc gctggaaccg cgtggggccg caagcgcttg gagccacccg cagttcgaaa    2460
aataataagg atccgaattc actggccgtc gttttacaac gtcgtgactg ggaaaaccct    2520
ggcgttaccc aacttaatcg ccttgcagca catccccctt tcgccagctg gcgtaatagc    2580
gaagaggccc gcaccgatcg cccttcccaa cagttgcgca gcctgaatgg cgaatggcgc    2640
ctgatgcggt attttctcct tacgcatctg tgcggtattt cacaccgcat acgtcaaagc    2700
aaccatagta cgcgccctgt agcggcgcat taagcccggc gggtgtggtg gttacgcgca    2760
gcgtgaccgc tacacttgcc agcgccctag cccccgctcc tttcgctttc ttcccttcct    2820
ttctcgccac gttcgccggc tttccccgtc aagctctaaa tcggggctc ctttagggt     2880 tccgatttag tgctttacgg cacctcgacc ccaaaaaact tgatttgggt gatggttcac    2940
gtagtgggcc atcgccctga tagacggttt ttcgtccttt gacgttcgag tccacgttct    3000
ttaatagtgg actcttgttc caaactggaa caatactcaa ccctatctcg gctattctt     3060 ttgatttata agggattttg ccgatttcgg cctattggtt aaaaaatgag ctgatttaac    3120
aaaaatttaa cgcgaatttt aacaaaatat taacgtttac aattttatgg tgcagtctca    3180
gtacaatctg ctctgatgcc gcatagttaa gccagccccg acaccgcca acacccgctg      3240 acgcgccctg acgggcttgt ctgctcccgg catccgctta cagacaagct gtgaccgtct    3300
ccgggagctg catgtgtcag aggttttcac cgtcatcacc gaaacgcgcg a             3351

<210> SEQ ID NO 5
<211> LENGTH: 20
<212> TYPE: DNA
<213> ORGANISM: Mus sp.

<400> SEQUENCE: 5
ctggatggtg ggaagatgga                                                  20

<210> SEQ ID NO 6
<211> LENGTH: 20
<212> TYPE: DNA
<213> ORGANISM: Mus sp.

<400> SEQUENCE: 6
tcagaggaag gaaacagggt                                                  20

<210> SEQ ID NO 7
<211> LENGTH: 30
<212> TYPE: DNA
<213> ORGANISM: Mus sp.

<400> SEQUENCE: 7
cttacaacca caatccctgg gcacaatttt                                       30

<210> SEQ ID NO 8
<211> LENGTH: 24
<212> TYPE: DNA
<213> ORGANISM: Mus sp.

<400> SEQUENCE: 8
ctttgtgggc cctctgggct caat                                             24

<210> SEQ ID NO 9
<211> LENGTH: 24
<212> TYPE: DNA
<213> ORGANISM: Mus sp.
```

```
<400> SEQUENCE: 9
tgaaatgggc cgctgggct caag                                        24

<210> SEQ ID NO 10
<211> LENGTH: 24
<212> TYPE: DNA
<213> ORGANISM: Mus sp.

<400> SEQUENCE: 10
gggcttgggt attctaggct cgat                                       24

<210> SEQ ID NO 11
<211> LENGTH: 23
<212> TYPE: DNA
<213> ORGANISM: Mus sp.

<400> SEQUENCE: 11
gaggtgcagc ttcaggagtc agg                                        23

<210> SEQ ID NO 12
<211> LENGTH: 23
<212> TYPE: DNA
<213> ORGANISM: Mus sp.

<400> SEQUENCE: 12
caggtgcagc tgaaggagtc agg                                        23

<210> SEQ ID NO 13
<211> LENGTH: 23
<212> TYPE: DNA
<213> ORGANISM: Mus sp.

<400> SEQUENCE: 13
gaggtccagc tgcaacagtc tgg                                        23

<210> SEQ ID NO 14
<211> LENGTH: 23
<212> TYPE: DNA
<213> ORGANISM: Mus sp.

<400> SEQUENCE: 14
gaggttcagc tgcagcagtc tgg                                        23

<210> SEQ ID NO 15
<211> LENGTH: 23
<212> TYPE: DNA
<213> ORGANISM: Mus sp.

<400> SEQUENCE: 15
caggtccaac tgcagcagcc tgg                                        23

<210> SEQ ID NO 16
<211> LENGTH: 23
<212> TYPE: DNA
<213> ORGANISM: Mus sp.

<400> SEQUENCE: 16
caggttcagc tgcagcagtc tgg                                        23

<210> SEQ ID NO 17
<211> LENGTH: 23
<212> TYPE: DNA
<213> ORGANISM: Mus sp.
```

```
<400> SEQUENCE: 17
gaggtgaagc tggtggagtc tgg                                         23

<210> SEQ ID NO 18
<211> LENGTH: 23
<212> TYPE: DNA
<213> ORGANISM: Mus sp.

<400> SEQUENCE: 18
gaggtgaagc tggtggaatc tgg                                         23

<210> SEQ ID NO 19
<211> LENGTH: 23
<212> TYPE: DNA
<213> ORGANISM: Mus sp.

<400> SEQUENCE: 19
gaggttcagc ttcagcagtc tgg                                         23

<210> SEQ ID NO 20
<211> LENGTH: 24
<212> TYPE: DNA
<213> ORGANISM: Mus sp.

<400> SEQUENCE: 20
tgaggagacg gtgaccgtgg tccc                                        24

<210> SEQ ID NO 21
<211> LENGTH: 24
<212> TYPE: DNA
<213> ORGANISM: Mus sp.

<400> SEQUENCE: 21
tgaggagact gtgagagtgg tgcc                                        24

<210> SEQ ID NO 22
<211> LENGTH: 24
<212> TYPE: DNA
<213> ORGANISM: Mus sp.

<400> SEQUENCE: 22
tgcagagaca gtgaccagag tccc                                        24

<210> SEQ ID NO 23
<211> LENGTH: 24
<212> TYPE: DNA
<213> ORGANISM: Mus sp.

<400> SEQUENCE: 23
tgaggagacg gtgactgagg ttcc                                        24

<210> SEQ ID NO 24
<211> LENGTH: 23
<212> TYPE: DNA
<213> ORGANISM: Mus sp.

<400> SEQUENCE: 24
gacattgtga tgacacagtc tcc                                         23

<210> SEQ ID NO 25
<211> LENGTH: 23
<212> TYPE: DNA
```

```
<213> ORGANISM: Mus sp.

<400> SEQUENCE: 25
gatgttgtga tgacccaaac tcc                                          23

<210> SEQ ID NO 26
<211> LENGTH: 23
<212> TYPE: DNA
<213> ORGANISM: Mus sp.

<400> SEQUENCE: 26
gatatccaga tgacacagac tcc                                          23

<210> SEQ ID NO 27
<211> LENGTH: 23
<212> TYPE: DNA
<213> ORGANISM: Mus sp.

<400> SEQUENCE: 27
caaattgttc tcacccagtc tcc                                          23

<210> SEQ ID NO 28
<211> LENGTH: 23
<212> TYPE: DNA
<213> ORGANISM: Mus sp.

<400> SEQUENCE: 28
caggctgttg tgactcagga atc                                          23

<210> SEQ ID NO 29
<211> LENGTH: 24
<212> TYPE: DNA
<213> ORGANISM: Mus sp.

<400> SEQUENCE: 29
tttgatttcc agcttggtgc ctcc                                         24

<210> SEQ ID NO 30
<211> LENGTH: 24
<212> TYPE: DNA
<213> ORGANISM: Mus sp.

<400> SEQUENCE: 30
ttttatttcc agcttggtcc cccc                                         24

<210> SEQ ID NO 31
<211> LENGTH: 24
<212> TYPE: DNA
<213> ORGANISM: Mus sp.

<400> SEQUENCE: 31
tttcagctcc agcttggtcc cagc                                         24

<210> SEQ ID NO 32
<211> LENGTH: 24
<212> TYPE: DNA
<213> ORGANISM: Mus sp.

<400> SEQUENCE: 32
acctaggaca gtgaccttgg ttcc                                         24

<210> SEQ ID NO 33
<211> LENGTH: 56
```

<212> TYPE: DNA
<213> ORGANISM: Mus sp.

<400> SEQUENCE: 33
gtcctcgcaa ctgcggccca gccggccatg gccgaggtgc agcttcagga gtcagg    56

<210> SEQ ID NO 34
<211> LENGTH: 56
<212> TYPE: DNA
<213> ORGANISM: Mus sp.

<400> SEQUENCE: 34
gtcctcgcaa ctgcggccca gccggccatg gcccaggtgc agctgaagga gtcagg    56

<210> SEQ ID NO 35
<211> LENGTH: 56
<212> TYPE: DNA
<213> ORGANISM: Mus sp.

<400> SEQUENCE: 35
gtcctcgcaa ctgcggccca gccggccatg gccgaggtcc agctgcaaca gtctgg    56

<210> SEQ ID NO 36
<211> LENGTH: 56
<212> TYPE: DNA
<213> ORGANISM: Mus sp.

<400> SEQUENCE: 36
gtcctcgcaa ctgcggccca gccggccatg gccgaggttc agctgcagca gtctgg    56

<210> SEQ ID NO 37
<211> LENGTH: 56
<212> TYPE: DNA
<213> ORGANISM: Mus sp.

<400> SEQUENCE: 37
gtcctcgcaa ctgcggccca gccggccatg gcccaggtcc aactgcagca gcctgg    56

<210> SEQ ID NO 38
<211> LENGTH: 56
<212> TYPE: DNA
<213> ORGANISM: Mus sp.

<400> SEQUENCE: 38
gtcctcgcaa ctgcggccca gccggccatg gcccaggttc agctgcagca gtctgg    56

<210> SEQ ID NO 39
<211> LENGTH: 56
<212> TYPE: DNA
<213> ORGANISM: Mus sp.

<400> SEQUENCE: 39
gtcctcgcaa ctgcggccca gccggccatg gccgaggtga agctggtgga gtctgg    56

<210> SEQ ID NO 40
<211> LENGTH: 56
<212> TYPE: DNA
<213> ORGANISM: Mus sp.

<400> SEQUENCE: 40
gtcctcgcaa ctgcggccca gccggccatg gccgaggtga agctggtgga atctgg    56

<210> SEQ ID NO 41

```
<211> LENGTH: 56
<212> TYPE: DNA
<213> ORGANISM: Mus sp.

<400> SEQUENCE: 41
gtcctcgcaa ctgcggccca gccggccatg gccgaggttc agcttcagca gtctgg      56

<210> SEQ ID NO 42
<211> LENGTH: 36
<212> TYPE: DNA
<213> ORGANISM: Mus sp.

<400> SEQUENCE: 42
gagtcattct cgtgtcgaca cggtgaccgt ggtccc                            36

<210> SEQ ID NO 43
<211> LENGTH: 36
<212> TYPE: DNA
<213> ORGANISM: Mus sp.

<400> SEQUENCE: 43
gagtcattct cgtgtcgaca ctgtgagagt ggtgcc                            36

<210> SEQ ID NO 44
<211> LENGTH: 36
<212> TYPE: DNA
<213> ORGANISM: Mus sp.

<400> SEQUENCE: 44
gagtcattct cgtgtcgaca cagtgaccag agtccc                            36

<210> SEQ ID NO 45
<211> LENGTH: 36
<212> TYPE: DNA
<213> ORGANISM: Mus sp.

<400> SEQUENCE: 45
gagtcattct cgtgtcgaca cggtgactga ggttcc                            36

<210> SEQ ID NO 46
<211> LENGTH: 41
<212> TYPE: DNA
<213> ORGANISM: Mus sp.

<400> SEQUENCE: 46
tgagcacaca gtgcactcga cattgtgatg acacagtctc c                      41

<210> SEQ ID NO 47
<211> LENGTH: 41
<212> TYPE: DNA
<213> ORGANISM: Mus sp.

<400> SEQUENCE: 47
tgagcacaca gtgcactcga tgttgtgatg acccaaactc c                      41

<210> SEQ ID NO 48
<211> LENGTH: 41
<212> TYPE: DNA
<213> ORGANISM: Mus sp.

<400> SEQUENCE: 48
tgagcacaca gtgcactcga tatccagatg acacagactc c                      41
```

```
<210> SEQ ID NO 49
<211> LENGTH: 41
<212> TYPE: DNA
<213> ORGANISM: Mus sp.

<400> SEQUENCE: 49
tgagcacaca gtgcactcca aattgttctc acccagtctc c                41

<210> SEQ ID NO 50
<211> LENGTH: 41
<212> TYPE: DNA
<213> ORGANISM: Mus sp.

<400> SEQUENCE: 50
tgagcacaca gtgcactcca ggctgttgtg actcaggaat c                41

<210> SEQ ID NO 51
<211> LENGTH: 48
<212> TYPE: DNA
<213> ORGANISM: Mus sp.

<400> SEQUENCE: 51
gagtcattct cgacttgcgg ccgctttgat ttccagcttg gtgcctcc         48

<210> SEQ ID NO 52
<211> LENGTH: 48
<212> TYPE: DNA
<213> ORGANISM: Mus sp.

<400> SEQUENCE: 52
gagtcattct cgacttgcgg ccgcttttat ttccagcttg gtccccc          48

<210> SEQ ID NO 53
<211> LENGTH: 48
<212> TYPE: DNA
<213> ORGANISM: Mus sp.

<400> SEQUENCE: 53
gagtcattct cgacttgcgg ccgctttcag ctccagcttg gtcccagc         48

<210> SEQ ID NO 54
<211> LENGTH: 48
<212> TYPE: DNA
<213> ORGANISM: Mus sp.

<400> SEQUENCE: 54
gagtcattct cgacttgcgg ccgcacctag gacagtgacc ttggttcc         48

<210> SEQ ID NO 55
<211> LENGTH: 6
<212> TYPE: PRT
<213> ORGANISM: Mus sp.

<400> SEQUENCE: 55

Leu Lys Val Ile Arg Lys
1               5
```

INHIBITORS OF EXTRACELLULAR HSP90

GOVERNMENT SUPPORT

This invention was made with government support under grant CA081668 awarded by the National Institutes of Health. The government has certain rights in the invention.

CROSS-REFERENCE TO RELATED APPLICATIONS

This application is a continuation application of U.S. patent application Ser. No. 13/870,955 filed Apr. 25, 2013, now abandoned which is a continuation application of U.S. patent application Ser. No. 12/951,737 filed on Nov. 22, 2010 and issued as U.S. Pat. No. 8,529,891 on Sep. 10, 2013, which is a continuation application of U.S. patent application Ser. No. 11/224,726 filed on Sep. 12, 2005 and issued as U.S. Pat. No. 7,959,915 on Jun. 14, 2011, which is a continuation of International Application No. PCT/EP2004/002422 filed Mar. 9, 2004, which designates the U.S. and which claims benefit under 35 U.S.C. §119(e) of U.S. Provisional Application No. 60/454,813 filed on Mar. 12, 2003, and European Patent Application No. 03015115.3, filed Jul. 3, 2003, the contents of each of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Nov. 18, 2013, is named 700355-079950-C3_SL.txt and is 20,628 bytes in size.

BACKGROUND OF THE INVENTION

Malignant tumors shed cells, which migrate to new tissues and create secondary tumors. The process of generating secondary tumors is called metastasis and is a complex process in which tumor cells colonize sites distant from the primary tumor. Liotta ((1986) Cancer Res. 46, 1-7) has proposed a three-step hypothesis for the process of metastasis: The first step is tumor cell attachment via cell surface receptors. The anchored tumor cell next secretes hydrolytic enzymes or induces host cells to secrete enzymes, which can degrade the matrix locally. Matrix lysis most likely takes place in a highly localized region close to the tumor cell surface. The third step is tumor cell locomotion into the region of the matrix modified by proteolysis. Thus, invasion of the matrix is not merely due to passive growth pressure but requires active biochemical mechanisms. Degradation of the surrounding normal tissue is a central feature of invasiveness of malignant tumors. The process of metastasis formation depends on the invasiveness of tumor cells. It would, therefore, be useful to develop drugs, which inhibit invasiveness and therewith prevent metastasis of primary tumors.

Recently, research has been focused on identifying specific proteins involved in metastasis, which can be used as a basis for better diagnostic or improved therapeutic strategies. A protein that has been identified as a molecular chaperone molecule and that is essential for the stability and function of several oncogenic proteins is heat shock protein 90 (Hsp90). This name is a generic term used to describe two isoforms termed Hsp90α and β. The structure and the function of the isoforms of Hsp90 is described in Csermely et al.: Pharmacol. Ther. Vol. 79, 1998, No. 2, The 90-kDa Molecular Chaperone Family: Structure, Function, and Clinical Applications. A Comprehensive Review, p. 131, p. 146. Hsp90 is one of the most abundant chaperones in the cytosol of eukaryotic cells and constitutes approximately 1-2% of all proteins in the cell. The intracellular functions of Hsp90 include stabilization of proteins (steroid receptors) and maturation of proteins such as kinases and other signalling proteins. Hsp90 has been implicated, however, in a wide variety of functions including evolutionary stability of mutated proteins, cytoskeletal rearrangements, nuclear transport, cell proliferation and apoptosis, protein degradation, antigen presentation and lipopolysaccharide recognition. Being very abundant in the cell Hsp90 has also been linked to many diseases, from cancer to autoimmune disease to cardiovascular disease. For example, a monoclonal antibody to the immunodominant LKVIRK (SEQ ID NO: 55) epitope of Hsp90 showed therapeutic activity in a treatment against fungal infection and was used in a clinical trial by the firm Neutec under the trade name Mycogrip™.

It has also been shown that Hsp90 is secreted from the cells in response to stress (Liao et al. (2000) J. Biol. Chem. 275, 189-96), but no known function has been associated with this secretion.

While Hsp90 has well-established functions intracellularly, reports of extracellular occurrence and its function are scarce. Hsp90 has been found to be an effective antigenic peptide presenter to receptors on antigen presenting cells. It has also been found to be one of four proteins associated in lipid rafts on the extracellular surface of cells, which bind to lipopolysaccharide and initiate intracellular responses (Triantafilou et al. (2002) Trends in Immunology 23, 301-4). Hsp90 has also been found overexpressed on the surface of some tumor cells: microcitomas, melanoma, and hepatoma cell lines (Ferrarini et al. (1992) Int. J. Cancer 51, 613-19). It has been hypothesized that expression of Hsp90 on the surface of these cell lines is connected to antigen presentation, but clear evidence is not yet available.

Hsp90 is also currently being assessed as an intracellular target in anti cancer drug development, due to its involvement in regulating several signalling pathways that are of importance in driving the phenotype of a tumor Inhibition of Hsp90 function has been shown to cause selective degradation of signalling protein involved in cell proliferation, cell cycle regulation and apoptosis. Several known antibiotics (e.g. geldanamycin, radicicol, and coumermycin A1) have been shown recently to be inhibitors of Hsp90 and are described in WO 00/53169. In this document a method of inhibiting binding of a chaperone protein with its client is proposed, wherein the method proposes contacting a chaperone protein with coumarin or a coumarin derivative. However, the teaching of WO 00/53169 is directed merely to the inhibition of intercellular Hsp90 protein.

Inhibitors such as the geldanamycin analogue 17-AAG are already being tested in clinical trials but there are concerns about toxicity resulting from non-specific inhibition of the protein across all cellular compartments (Dunn (2002) J. Natl. Cancer Inst 94, 1194-5). Furthermore, the lack of understanding of the interaction of Hsp90 with client proteins in various cell signalling processes bears potential risks of inhibiting intracellular Hsp90 with toxic inhibitors.

The determination of the physiological role of a protein is a prerequisite for deciding whether interference with this protein function might be a possible avenue for the treatment of disease or not. It must be kept in mind that in a physiological setting, i.e. in a naturally occurring tumor cell of a patient, Hsp90 acts together with other proteins, which can modulate and interfere with each other. It is the functional interplay between Hsp90 and interacting proteins that determines its physiological role.

Hsp90 has also been reported to act as a molecular chaperone for transmembrane protein transport in the nucleus (Schlatter et al. (2002) Biochem. J. 362, 675-84), and has been implicated in drug efflux in leukemia, lung and ovarian carcinoma cells (Rappa et al (2002) Oncol. Res. 12, 113-9 and Rappa, et al (2000) Anticancer Drug Des 15, 127-34).

The present invention demonstrates for the first time that the inhibition of extracellular Hsp90 leads to a reduction of the invasiveness of the tumor cells. The present invention shows a novel avenue to inhibit extracellular Hsp90 whereby side effects associated with attacking the intracellular Hsp90 can be prevented.

The present invention also shows an interrelationship between Hsp90 inhibition and the secretion of matrix metalloproteases (MMPs). MMPs act in invasion by digesting surrounding extracellular matrix to allow cells to migrate through dense tissues. Our results showed that Hsp90 is critical for invasion of cancer cells by increasing secretion or activity of MMPs, when overexpressed in fibrosarcoma cells. We further showed that Hsp90-dependent invasion can be inhibited by using the molecules of the invention.

The present invention relates to the use of molecules interfering with the function of extracellular Hsp90 on tumor cells for the treatment of specific cancers. Compounds, compositions and methods are provided that are useful for reducing or inhibiting the invasiveness and/or the metastatic potential of specific tumor cells. Furthermore, a method is provided that allows to determine whether a tumor cell depends on functional extracellular Hsp90 for its invasiveness and/or metastatic potential.

SUMMARY OF THE INVENTION

The present invention relates to molecules, which can specifically bind to the extracellular Hsp90. Furthermore, the molecules of the invention can be labeled with detectable groups, if desired, or can be part of a bioconjugate.

The invention further relates to pharmaceutical compositions comprising an inhibitor of extracellular Hsp90.

In a further embodiment the invention relates to nucleic acid molecules encoding inhibitors of extracellular Hsp90, if the inhibitors are selected from a group comprising polypeptides, antibodies or antibody fragments as well as to vectors comprising such a nucleic acid and to host cells comprising such a vector.

In a further embodiment the invention relates to the use of molecules inhibiting extracellular Hsp90 function for the manufacture of a medicament for the treatment or prevention of invasion and/or metastatic potential of cancer cells.

In a further embodiment the invention relates to a method of treating or preventing invasion and/or metastatic potential of cells in a patient, wherein the method comprises administering to a person in need thereof a therapeutically effective amount of the molecules, and/or the pharmaceutical composition according to the invention.

In a further embodiment the invention relates to a method to determine the dependency of the invasiveness of cancer cell on the functionality of extracellular Hsp90.

In a further embodiment the invention relates to a method for the identification of molecules useful for inhibiting the invasiveness of a cancer cell, particularly the identification of such ligands that bind to Hsp90.

In a further embodiment the invention relates to the use of classes of molecules for reducing the activity of matrix metalloprotease (MMP).

DEFINITIONS

As used herein, the following definitions shall apply unless otherwise indicated.

A "polypeptide" as used herein is a molecule comprising more than 10, preferably more than 20, most preferably more than 30, and less than 10000, more preferably less than 2500, most preferably less than 1000 aminoacids. Also polypeptides containing modified or non-natural amino acids are encompassed.

The terms "antibody" and "immunoglobulin", as used herein refer to any immunological binding agent, including polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like.

Antibodies may be also selected from modified immunoglobulins, for example chemically or recombinantly produced antibodies, CDR grafted antibodies or humanized antibodies, site directed mutagenized antibodies that exhibit substantial amino acid sequence identity in their CDR regions, particularly in their CDR3 region, to the corresponding antibody fragments of the invention and retain substantially the same affinity for Hsp90 binding as the corresponding antibody fragments.

The CDRs (complementary determining region) of an antibody are the parts of these molecules that determine their specificity and make contact with specific ligands. The CDRs are the most variable parts of the molecule and contribute to the diversity of these molecules.

Substantial amino acid sequence identity as used herein means that at least 70%, preferably at least 75%, 80%, 85%, 90%, more preferably all but 5, still more preferably all but 3 and even more preferably all but 1 of the amino acids of two aligned amino acid sequences, particularly of aligned CDRs, are identical.

The term "antibody fragment" is used to refer to any fragment of an antibody-like molecule that has an antigen binding region, and this term includes antibody fragments such as scFv, dsFv, Fab', Fab, F(ab')$_2$, Fv, single domain antibodies (DABs), diabodies, and the like. The techniques for preparing and using various antibody-based constructs and fragments are well known in the art (see Kabat et al. (1991) J. Immunol. 147, 1709-19), specifically incorporated herein by reference.

"scFv" antibody fragments comprise the VH and VL domains of an antibody, wherein these domains are present in a single polypeptide chain. Generally, the scFv polypeptide further comprises a polypeptide linker between the VH and VL domains that enables the scFv to form the desired structure for antigen binding.

A "Fv" fragment is the smallest antibody fragment that retains an intact antigen binding site.

A "dsFv" is a disulfide stabilized Fv.

A "Fab" fragment, is an antigen binding fragment, containing complete light chains paired with the VH and CH1 domains of the heavy chain.

A "Fab" fragment, is a reduced F(ab')$_2$ fragment.

A "F(ab')$_2$" fragment, is a bivalent fragment comprising two Fab fragments linked by a disulfide bridge at the hinge region.

A "single domain antibody (DAB)" is an antibody with only one (instead of two) protein chain derived from only one of the domains of the antibody structure. Dabs exploit the finding that, for some antibodies, half of the antibody molecule binds to its target antigen almost as well as the whole molecule (Davies et al. (1996) Protein Eng. 9: 531-537.

"Diabodies" are bivalent or bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (Holliger et al. (1993) Proc. Natl. Acad. Sci. USA, 90, 6444-6448).

The term "biogonjugate" as used herein means that an inhibitor of extracellular Hsp90 is covalently or non-covalently linked and/or coupled to or with, respectively, another protein, a solid matrix (e.g. like a bead), with itself to form multimers, a cytotoxic agent further enhancing the toxicity to targeted cells, a cytostatic agent, a prodrug, or an effector molecule, which is able to modify the cell expressing Hsp90 or to recruit immune cells.

The terms "label" or "labeled" refers to a detectable marker or the incorporation of such, respectively, e.g., by incorporation of a fluorophore-, chromophore- or radiolabeled amino acid or the attachment of a fluorophore-, chromophore- or radiolabel to a ligand or the attachment of moieties that can be detected by a labeled second molecule containing a fluorescent marker or enzymatic activity that can be detected by an optical or a colorimetric method. An example for such a two-step detection system is the well known biotin-avidin system. Various methods of labeling polypeptides and glycoproteins are known in the art (for example, see Lobl et al. (1988) Anal. Biochem., 170, 502-511) and may be applied for different classes of molecules.

An "epitope" includes any protein determinant capable of specific binding to an immunoglobulin or an antibody fragment. Epitopic determinants usually consist of chemically active surface groupings of molecules such as exposed amino acids, aminosugars, or other carbohydrate side chains and usually have specific three-dimensional structural characteristics, as well as specific charge characteristics.

"Treating metastatic tumors" or "treating micro-metastases", as used herein means that the metastasis of the tumor is stabilized, prevented, delayed, or inhibited by the molecule of the invention, either as a single medicament or in combination with other medicaments. Stable disease or "No Change" (NC) is a description for the course of the disease with either no change of the metastases or a reduction of less than 50% or an increase of less than 25% over at least 4 weeks. Prevention can be, for example, that no new metastases are detected after the treatment is initiated. This can lead to a two- to three-fold median and/or a %-year survival rate of treated patients compared with untreated patients. A delay can signify a period of at least 8 weeks, 3 months, 6 months or even one year in which no new metastases are detected after the treatment is initiated. Inhibition can mean that the average size or the total number of new metastases is at least 30%, 40%, 50%, 60%, 70%, 80% or even 90% lower in a group treated with the molecule of the invention in comparison with an untreated group. Number, size and prevalence of metastases can be detected by a skilled practitioner in the field of oncology following generally accepted practice and diagnostic procedures for the detection of metastases, for example as outlined in Harrisons Principles of Internal Medicine 15th ed 2001 Mc Graw Hill.

"Metastatic tumors" as used herein include both tumors at the primary site capable of metastasizing and metastasized tumors at a secondary site.

"A micro-metastase" is an accumulation of tumor cells with a size smaller than 2 mm, which can usually only be detected by histological methods.

"Invasiveness" as used herein is the ability of a cell to migrate through a layer of other cells or to migrate through the extracellular matrix. Invasiveness can be assessed by the Matrigel assay described in the Examples. Invasion is measured as the percentage of cells that reach the lower surface of the filter during a certain incubation period.

"Metastatic potential" as used herein is the ability of a tumor cell to form a new tumor at a site distant from the primary tumor of which the tumor cell was derived (a metastase). "Therapeutically effective amounts" are amounts which eliminate or reduce the patient's tumor burden, or which prevent, delay or inhibit metastasis. The dosage will depend on many parameters, including the nature of the tumor, patient history, patient condition, the possible co-use of cytotoxic agents, and methods of administration. Methods of administration include injection (e.g., parenteral, subcutaneous, intravenous, intraperitoreal, etc), for which the molecule inhibiting extracellular Hsp90 function is provided in a nontoxic pharmaceutically acceptable carrier. In general, suitable carriers and diluents are selected so as not to significantly impair biological activity of the binding agent (e.g., binding specificity, affinity or stability), such as water, saline, Ringer's solution, dextrose solution, 5% human serum albumin, fixed oils, ethyloleate, or liposomes). Acceptable carriers can include biocompatible, inert or bio-absorbable salts, buffering agents, oligo- or polysaccharides, polymers, viscoelastic compound such as hyaluronic acid, viscosity-improving agents, preservatives, and the like. In addition, the pharmaceutical composition or formulation may also include other carriers, adjuvants, or nontoxic, non-therapeutic, non-immunogenic stabilizers and the like. Typical dosages may range from about 0.01 to about 20 mg/kg, or more particularly from about 1 to about 10 mg/kg.

Therapeutic methods employing molecules inhibiting Hsp90 function may be combined with chemotherapy, surgery, and radiation therapy, depending on type of the tumor, patient condition, other health issues, and a variety of factors. The molecules inhibiting Hsp90 function may also be used as the single effective medicament of a therapeutic composition.

A "molecule inhibiting extracellular Hsp90", is a molecule resulting in inhibition of the biological activity of extracellular Hsp90. This inhibition of the biological activity of extracellular Hsp90 can be assessed by measuring one or more indicators of extracellular Hsp90's biological activity, such as Hsp90 dependent invasiveness. These indicators of Hsp90's biological activity can be assessed by one or more of several in vitro or in vivo assays (see Examples). Preferably, the ability of a molecule to inhibit Hsp90 activity is assessed by inhibition of Hsp90-induced invasiveness of invasive human cells, particularly the cells used in the Examples.

A "molecule inhibiting extracellular Hsp90 function" of the invention is not a molecule which is a general inhibitor of protein function, like a protease, like a denaturing agent, e.g. urea or guanidinium hydrochloride, like heavy metal atoms or like small molecules (e.g. aldehydes or isocyanates) reacting covalently and non-specifically with biomolecules (lipids, proteins, sugars). Inhibition is understood as a decrease in function, when compared to a negative control with the same experimental conditions, but without the molecule of the invention.

Additionally, in the case of a polypeptide of the invention, particularly an antibody or antibody fragment of the invention, the polypeptide of the invention is considered to inhibit the biological function of extracellular Hsp90 if it reduces the invasiveness of cancer cells in an experiment as described in the Examples by more than 30%, preferably more than 60%, when said antibody fragment is present at a concentration of 1 nM to 50 µM, preferably around 20 µM.

Additionally, with regard to the inhibitors of extracellular Hsp90, such inhibitor is encompasses by the present invention if it reduces the invasiveness of invasive cancer cells in an experiment as described in the Examples by more than 30%, preferably by more than 60%, when present at a concentration of 10 nM to 100 µM, preferably at around 1 µM.

"Extracellular Hsp90" as used herein is Hsp90 that is loosely associated with the cell membrane and outside of the cell and is not to be understood to encompass isolated Hsp90. This can include Hsp90 insertion in the membrane by post-translational modifications or physical integration so as to expose it to the extracellular face of the cell or secretion of Hsp90 to the extracellular space.

The term "inhibitor" of extracellular Hsp90 is any entity, which binds extracellular Hsp90 and decreases its function, especially with regard to the cells properties such as invasiveness and/or metastatic potential. Such an entity can be an ionic or a non-ionic organic or non-organic small molecule (i.e. preferably having a molecular weigh of less than 1500 Da), naturally and non-naturally occurring macromolecules, a polypeptide which can be modified, in particular with naturally and non-naturally occurring sugar moieties or otherwise chemically modified, an antibody, in particular a monoclonal antibody, antibody fragments etc.

The term "a" is not to be construed to mean "one" and can also mean "one and/or more than one", if not otherwise stated.

DETAILED DESCRIPTION OF THE INVENTION

In order that the invention described herein may be more fully understood, the following detailed description is provided.

The present invention relates to inhibitors, which can specifically bind extracellular Hsp90 and more particularly can inhibit Hsp90 function related to the invasiveness and/or metastatic potential of cancer cells. The inhibitor of extracellular Hsp90 is preferably either essentially unable to enter into the cell or is modified in such a manner that the modification essentially prohibits its cellular uptake. The modification of the inhibitors of the present invention can be achieved by conjugating the inhibitors to naturally occurring macromolecules such as polypeptides, sugars or to an artificially made, biologically compatible polymers.

Preferably, the inhibitor of the present invention is a bioconjugate with, respectively, another protein, a solid matrix (e.g. like a bead), with itself to form multimers, a cytotoxic agent further enhancing the toxicity to targeted cells, a cytostatic agent, a prodrug, or an effector molecule, which is able to modify the cell expressing Hsp90 or to recruit immune cells.

The inhibitors of the present invention for inhibiting extracellular Hsp90 can be, thus, already known inhibitors of (intracellular Hsp90) such as geldanamycin and its analogues such as 17AAG, radicicol, coumarin antibiotics such as novobiocin or purine based Hsp90 inhibitors such as PU3, when there are used to inhibit extracellular Hsp90. However, it is preferred that the known inhibitors are modified such that the cellular uptake is essentially prohibited so that any side effects associated with the possible toxicity of the inhibitors of (intracellular) Hsp90 are eliminated.

A list of cytotoxic agents include, but is not limited to, daunorubicin, taxol, adriamycin, methotrexate, 5 FU, vinblastin, actinomycin D, etoposide, cisplatin, doxorubicin, genistein, andribosome inhibitors (e.g., trichosantin), or various bacterialtoxins (e.g., *Pseudomonas* exotoxin; *Staphylococcus aureus* protein A).

The inhibitor of the present invention is preferably selected from a group comprising polypeptides, antibodies, antibody fragments, coumarin and/or purine based Hsp90 inhibitors and their analogs.

Bioconjugates comprising the polypeptides of the invention, particularly the antibody fragment or antibody of the invention, together with a cytotoxic moieties are made using a variety of bifunctional protein coupling agents. Some examples of such reagents are N-succinimidyl 3-(2-pyridyldithio)-propionate (SPDP), bifunctional derivatives of imidoesters such a dimethyl adipimidate HCl, active esters such as disuccinimidyl suberate, aldehydes such as glutaraldehyde, bisazido compounds such as his (R-azidobenzoyl) hexanediamine, bisdiazonium derivatives such as bis-(R-diazoniumbenzoyl)ethylenediamine, diisocyanates such as tolylene 2,6-diisocyanate, and bis-activated fluorine compounds such as 1,5-difluoro-2,4-dinitrobenzene. Methods useful for the production of bioconjugates are described in detail in March's Advanced Organic Chemistry: Reactions, Mechanisms and Structure, 5th Edition, Wiley-Interscience; or Bioconjugate Techniques, Ed. Greg Hermanson, Academic Press.

In another preferred embodiment the polypeptide of the invention is an antibody, in one preferred embodiment an antibody derived from a scFv antibody fragment, in another preferred embodiment a polyclonal or a monoclonal antibody, particularly a human monoclonal antibody.

Anti-human Hsp90 antibodies binding to extracellular Hsp90 may be selected from modified immunoglobulins, for example chemically or recombinantly produced antibodies or humanized antibodies, site directed mutagenized antibodies, that exhibit substantial amino acid sequence identity in their CDR regions, particularly in their CDR3 region, to the corresponding antibody fragments of the invention and retain substantially the same affinity for Hsp90 binding as the corresponding antibody fragments.

In another preferred embodiment the anti-human Hsp90 antibody is selected from the group consisting of IgA, IgD, IgE, IgG, and IgM, in particular IgG and IgM, more particularly IgG1, IgG2a, IgG2b, IgG3, IgG4.

In another preferred embodiment of the invention the inhibitor of the invention is particularly an antibody fragment.

Preferably the inhibitor of the invention is an antibody fragment, in particular a scFv, dsFv, Fab', Fab, F(ab')$_2$, Fv, single domain antibody or diabody, more particularly a scFv, dsFv, Fv, single domain antibody or diabody, still more particularly a scFv, single domain antibody or diabody and even more preferably a scFv.

In another embodiment, the antibody fragment of the invention specifically recognizes one or more epitopes of Hsp90, or epitopes of conserved variants of Hsp90, or peptide fragments of the Hsp90.

As an example, one way to increase the biological activity of the molecules of the invention is to use the molecules (or ligands) in combination with CALI (Chromophore-assisted Laser/Light Inactivation).

The principle of CALI (Chromophore-assisted Laser/Light Inactivation) is based on the local initiation of a photochemical reaction that leads to the generation of short-lived reactive species, which in turn selectively modify the target molecule and cause its functional inactivation. Highly specific but non-inhibitory ligands (e.g. antibodies, antibody fragments, small molecules) are labeled with a suitable fluorophore (e.g. fluorescein isothiocyante). After complex formation between the target molecule (e.g. proteins) and the ligand, the complex is irradiated with laser light or white light to excite the chromophore or fluorophore, respectively. The excitation triggers a photochemical reaction that initiates the generation of short-lived reactive species (e.g. hydroxyl radicals or highly reactive oxygen species). These reactive species modify the protein within a small radius around their site of generation. The distance that a reactive species can travel is very short due to its short lifetime. Therefore, the modifications of amino acid residues within the protein occur in close proximity to the binding site of the ligand. The damaging effect is restricted to a radius of 15-40 .ANG., which is well below the average distance of two proteins within a cell, which is at about 80 .ANG., (assuming an average cytosolic protein concentration of 300 mg/ml and an average protein size of 50 kDa) ensuring a high spatial resolution of the process. This principle is shown in FIG. 12. In cases where the binding site of the ligand is close or within an important functional domain of the protein, these induced modifications lead to permanent inactivation of the protein. The functional inactivation of the protein is measured in an appropriate readout assay and evaluated in the context of disease relevant physiological functions like cell invasion, cell adhesion, cell signaling or apoptosis.

Inactivation of proteins with CALI was shown to be very specific to the respective protein. Linden et al showed that β3-galactosidase could be efficiently inactivated with a malachite-green labeled anti-β-galactosidase antibody even in the presence of alkaline phosphatase in the same solution. β-galactosidase was inactivated by 95% after 10 min of laser irradiation whereas alkaline was not effected at all (Linden et al. (1992) Biophys. J. 61, 956-962). Jay also demonstrated that a dye-labeled antibody bound to a single epitope of a protein was sufficient to inactivate acetylcholinesterase (Jay (1988) Proc. Natl. Acad. Sci. USA, 85, 5454-58).

Henning et al. described that CALI was successfully used against a diverse array of proteins (Henning et al. Drug Discovery 62-71). These proteins include membrane proteins (eg. α-, β-, .epsilon.-chains of T cell receptor, β1 integrins, ephrin AS or FAS receptor), signal transduction molecules (eg. Calicineurin, cyclophillin A or PKC), cytoskeletal proteins (eg. Actin, ezrin or kinesin) or transcription factors. Henning et al. further described that CALI can be used for identification of novel proteins as drug targets and at the same time the elucidation of their function in the biological context of interest (Henning et al. (2002) Current Drug Discovery May, 17-19).

Several application examples of CALI show that this technique is able to convert specific but non-inhibitory ligands into blocking reagents. Therefore, these ligands can be used to modulate the action of inhibitory ligands. CALI can also be used to further enhance the inhibitory effect of a ligand that has already an inhibitory effect by itself. The experimental part shows Examples where CALI is integrated in an invasion or an adhesion assay.

The chemical modification of the molecule can be the addition of chromophores or fluorophores. A chromophore is that part of a molecule that possesses high optical activity due to mobile electrons that interact with light. Chromophores are called fluorophores, if they absorb light in the visible range of the spectrum. Some examples of chromophores are, e.g., fluorescein derivatives, rhodamine derivatives, coumarin derivatives, porphyrin derivatives, phthalocyanine derivatives, naphthalocyanines derivatives eosin derivatives, triphenylmethane derivatives or acridine derivatives. A list of chromophores and useful derivatives for chemically modifying biomolecules is disclosed in The Sigma Aldrich Handbooks of Stains and Dyes, Ed., F. J. Green (1990) ISBN No. 0-941633-22-5.

In another aspect of the present invention the inhibitor is labeled with a detectable label. Particularly, examples for detectable labels are radioisotopes, chromophores, fluorophores or enzymes.

The expression of a cancer-associated Hsp90 antigen can be detected by using a bioconjugate or a polypeptide of the invention, particularly an antibody or an antibody fragment of the invention. A sample is taken from the subject, e.g., a biopsy specimen taken from tissue suspected of having a tumor. Generally, the sample is treated before an assay is performed. Assays, which can be employed include ELISA, RIA, EIA, Western Blot analysis, immunohistological staining and the like. Depending upon the assay used, the antigens or the antibodies can be labeled by an enzyme, a fluorophore or a radioisotope. (See, e.g., Coligan et al. (1994) Current Protocols in Immunology, John Wiley & Sons Inc., New York, N.Y.; and Frye et al. (1987) Oncogene 4, 1153-1157.)

In another embodiment the modified polypeptide or the bioconjugate of the invention, binds to human, extracellular Hsp90 and reduces the invasiveness and/or metastatic potential of cancer cells. One method to measure a degree of the invasiveness of human cancer cells is given in the Examples.

The present invention also relates to a pharmaceutical composition comprising effective amounts of an inhibitor of extracellular Hsp90 particularly for reducing the invasiveness and/or metastatic potential of cancer cells. Preferably, the inhibitor is either essentially unable to enter into a cell or is modified in such a way that the cellular uptake of the inhibitor is essentially prohibited. The pharmaceutical composition of the present invention can be used for the preparation of a medicament for the prevention and/or the treatment of the proliferative disorders such as cancer or metastasis.

The present invention also relates to a pharmaceutical composition comprising effective amounts of at least one inhibitor, particularly one antibody or an antibody fragment and the use of the antibody or an antibody fragment for the preparation of a medicament for the prevention and/or treatment of proliferative disorders, cancer or metastasis. The inventors demonstrate herein that an antibody to extracellular human Hsp90 binds to MD-MDA231 breast adenocarcinoma cells, HT-1080 fibrosarcoma cells and melanoma cells. Accordingly, in some embodiments, the cancer or metastasis to be treated with an inhibitor of extracellular Hsp90 can be selected from any or a combination of cancers, such as breast, adenocarcinoma, melanoma, adrenocarcinoma, and fibrosarcoma.

In another embodiment, the present invention encompasses a diagnostic kit. In some embodiments, a diagnostic kit as disclosed herein can be used to identify the presence of extracellular human Hsp90 on a cancer biopsy sample from a subject. Such a kit comprises at least one bioconjugate and/or at least one inhibitor or a labeled version of these, and consists additionally of the reagents and materials necessary to carry out a standard competition or sandwich assay. Said diagnostic kit may be used for the determination of the invasive potential of biological samples, in particular of certain cancer cell types. A kit will further typically comprise a container.

In another aspect, the present invention encompasses a method for screening or testing the invasion and/or the metastatic behavior of the cells ex vivo, comprising the steps of:

a) contacting the cell with one or more Hsp90 inhibitors under the conditions which essentially prohibit a cellular uptake of said Hsp90 inhibitor;

b) analyzing the migration of cells treated according to step a);

c) comparing the migration of the cells treated according to step a) with untreated the cells and optionally d) determining the percentage of migration of the cells treated according to step a) with untreated cells.

In a preferred embodiment of this aspect of the present invention the screening is performed such that the cells are contacted with a gel-like matrix under the conditions suitable for the growth of the cells and step b) comprises, thus, analyzing the migration of the cells through the matrix.

The term "gel-like matrix" as used herein is understood to be a semi-solid substance with a water content of at least 90%, which allows cultivation of cancer cells in contact with the matrix and allows migration of invasive cancer cells through a slab of said "gel-like matrix" of 0, 1 mm to 1 mm, preferably 0.3 mm thickness, but not migration of non-invasive cells. Examples for such a "gel-like matrix" are substances resembling the extracellular matrix in protein and carbohydrate composition, particularly the commercially available "Matrigel". Particularly the "gel-like matrix" comprises one of the proteins selected from the group consisting of the proteins collagen type IV, fibronectin and laminin. More particularly the gel-like matrix comprises the proteins collagen type IV, fibronectin and laminin. More preferable the gel-like matrix comprises the proteins collagen type IV, laminin, entactin, nidogen and heparan sulfate proteoglycans or collagen type IV, fibronectin, laminin, nidogen, entactin, and vitronectin.

The present invention further provides a method of identifying an inhibitor binding specifically to Hsp90, by screening a library of ALDUs, wherein these inhibitors are capable of inhibiting Hsp90 related invasiveness, adhesiveness and/or metastatic potential of cancer cells. Said method comprises the steps of:

a) contacting a library of amplifiable ligand-displaying units (ALDU) with a cancer cell, e.g. a sarcoma cell;

b) separating said cancer cell and the ALDUs bound thereto from ALDUs not bound to said cancer cell;

c) amplifying the ALDUs bound to said cancer cell;

d) identifying an ALDU or a ligand derived from an ALDU after step c), which affects said biological activity of Hsp90 by a functional screening assay;

e) identifying an ALDU or a ligand derived from an ALDU after step d) capable of binding to Hsp90 f) determining the chemical identity of the ligand.

The preferred—but not the only possible—order of the steps is a, b, c, d, e and optionally f.

As used herein "amplifiable ligand-displaying units" (ALDUs) are molecules or collections of molecules with dual function: they can bind to a target cell via a ligand; and they carry physically associated with the ligand an information about its identity, which allows individual units to be identified, and amplified. Examples of ALDUs are oligonucleotides, particularly RNAs, useful for the process of selection-amplification (SELEX), phages of phage displa libraries, viruses of viral display libraries, ribosomes of ribosome-display techniques, but also individualized beads carrying an identifiable molecule or ligand, particularly chemical entities, e.g. small molecules bound to beads, which are recognizable by inert chemical tags. Preferred are such ALDUs, which comprise a nucleic acid as the identifiable component. Such ALDUs can be either amplified in vitro, e.g., by nucleic-acid amplification methods like RT-PCR, PCR, LCR and the like, or they can be amplified in vivo, for example an individual phage can infect a bacterium and yield, after several cycles of infection, millions of virtually identical progeny. A library of ALDUs is a collection of similar, but in general non-identical ALDUs, for example phages of a phage library that display different scFvs in the context of an otherwise identical phage surface.

A ligand "derived from an ALDU" as mentioned herein is a ligand, which had been displayed by such an ALDU, which had been selected by binding to the surface of a target cell. As an example, if the ALDU is a phage of a phage library displaying scFvs the "ligand derived from an ALDU" in this case is a polypeptide, here a scFv. As another example, in the case of ribosomal display the ligand "derived from an ALDU" is the polypeptide, which was presented by the complex comprising the ribosome, the RNA and the polypeptide.

The method advantageously combines a screening step based on binding to the surface of a cancer cell with a screening step based on a functional assay. Therefore a library of ALDUs is brought in contact with a cancer cell in such a way that those ALDUs of the library with specificity for a surface antigen of the cancer cell can bind to structures associated with the surface of e.g. the cancer cell. For example phages of a phage library displaying antibodies or antibody fragments can be allowed to bind to cultured cancer cells or, as another example, RNA of an RNA-oligonucleotides library can be allowed to bind to such cancer cells.

The identity of ALDUs representing the antibody or the antibody fragment obtained with step d) can be determined by, e.g., sequencing the DNA encoding the antibody or the antibody fragment, or, in the case of a commercial library with gridded or numbered phages, by determining the grid position or the number of the phage. The grid position or the number then can reveal the identity of the antibody or the antibody fragment represented by the ALDU.

A "ligand" as used herein is a molecule displayable by an amplifiable ligand-displaying unit (ALDU). A ligand can be any entity that binds extracellular Hsp90 and inhibits its function. A ligand is that part of an ALDU through which the ALDU can bind to a target.

A ligand "binding specifically to extracellular Hsp90" as mentioned herein can be a ligand, which binds to Hsp90 under the buffer conditions given in the Examples. The dissociation constant between the ligand and Hsp90 can be measured, e.g. by use of the so-called BIACORE System (see, for example, Fivash et al. Curr Opin Biotechnol. (1998) 9, 97-101) and "binding specifically" can then be understood to mean that the dissociation constant between the ligand and Hsp90 is lower than 10 µM, preferably lower than 1 µM, more preferably lower than 500, 400, 300, 200, 100, 50, 20 nM, most preferably from 0.1 nM to 20 nM if measured under standard conditions, for example at 20° C., ambient pressure and in a suitable buffer, e.g. 20 mM Tris, 100 mM NaCl, 0.1 mM EDTA at an overall pH of 7.0.

As used herein "contacting" of two components means allowing the two components to physically associate with one another and bind to one another.

"Separating" as used herein means the physical separation of two or more components, for example a cell with an ALDU bound thereto can be separated from a free ALDU by centrifugation, wherein the cell with the ALDU bound thereto is pelleted and the free ALDU is still in the supernatant.

"Amplifying" as used herein is any process that increases the number of ALDUs or ligands derived from ALDUs by at least a factor of two, preferably by a factor of 10, 100, 1.000, 10.000, 100.000, 1.000.000, 10.000.000 or even a billion. For example a single phage can be amplified by infecting a bacterium and the infected bacterium then produces several mostly identical copies of the infecting phage, or a DNA-molecule can be amplified by the process of PCR to yield 104 or more mostly identical daughter DNA-molecules.

"Identifying" as used herein means locating or recognizing an individual component, for example an ALDU, with special properties and isolating said individual component.

"Determining the chemical identity of a ligand" as used herein means determining the structural composition of a ligand. For example, if the ALDU library is a phage library displaying scFvs, then "determining the chemical identity of a ligand" would mean to determine the sequence of the scFv polypeptide, for example by sequencing the region encoding the scFv of the phage from which it was derived.

"A screening assay" as used herein is aimed at detecting an individual, e.g. an ALDU, with special properties among other similar individuals with slightly different properties. In order to qualify for a screening assay at least 3, 4, 5, 6, 7, 8, 9, 10, 20, 30, 40, 50 or even 100 individuals must be tested in a certain functional assay to find an individual/individuals with the desired function detected among them.

In the separating step (b.) according to the present invention, the cancer cell and the ALDUs bound thereto are separated from unbound ALDUs, in order to select for those ALDUs with specificity for the cancer cell. The separation can be achieved, e.g., by removing the solution, in which the contacting step has been performed from cultured cancer cells grown adhesively in a culture flask and together with the solution the unbound ALDUs; or, as another example, cancer cells with RNAs of a SELEX library bound thereto can be pelleted by centrifugation, while the unbound RNAs remain in the supernatant as part of the solution, in which the contacting step had been performed. Alternatively, separation can be achieved by centrifugation, density centrifugation, filtration, FACS sorting, immunoprecipitation or immobilization onto a solid support. For example an ALDU bound to a cancer cell can be separated from unbound ALDUs making use of the fact that the complex of an ALDU bound to a target has different biochemical properties compared to an unbound ALDU. Those changed biochemical properties can be size, specific binding, charge density, density or the like.

Filtration can separate the bound ALDUs from the unbound ALDUs, e.g. if the size of the filter is such that ALDUs bound to the cancer cell are retained by the pores of the filter, while the unbound ALDUs can pass through the pores of the filter. Filtration by size is therefore useful if the target is large, like the cancer cell, and the ALDU is small, e.g. a phage, a virus, a nucleic acid or a ribosome displaying a ligand.

Density centrifugation separates biomolecules according to their density. Density centrifugation can be applied if the density of an ALDU bound to a target is different from that of an unbound ALDU. For example, the density centrifugation can be applied if an ALDU is dense, e.g. a ribosome displaying a ligand, and the target is not as dense, like a sarcoma cell or vehicles derived from the membrane of a cancer cell.

FACS can separate the complex of ALDU bound to a cancer cell from unbound ALDUs based on fluorescence of the target. FACS can be performed by labeling the cancer cell with a fluorescent dye and then passing the labeled cancer cell in suspending medium through a narrow dropping nozzle so that each cancer cell is in a small, separate droplet. A laser-based detector system is often used to excite the fluorescent dye and droplets with e.g. fluorescence-positive cancer cells are given an electric charge. Charged and uncharged droplets can then be separated as they pass charge plates and can be collected in two different tubes. In this way small droplets containing ALDUs that are bound to a cancer cell are separated from bulk solution containing unbound ALDUs.

Immobilization of the cancer cell onto solid support can be performed in order to separate ALDUs bound to the immobilized cancer cell from unbound ALDUs. Immobilization of the cancer cell onto solid support is often performed by using a surface activated solid support or specific binding of the solid support surface with the cancer cell using e.g. biomolecules with specific binding properties towards the cancer cell. In order to separate ALDUs that are bound to the immobilized cancer cell from unbound ALDUs, the immobilized cancer cell is separated from the bulk solution containing unbound ALDUs.

Separation of ALDUs bound to the immobilized cancer cells from the bulk solution containing unbound ALDUs can be performed by removing the bulk solution containing the unbound ALDUs from the immobilized cancer cells. For example, if the cancer cell is immobilized onto e.g. the well of a plastic micro titer plate via covalent interactions then the bulk solution containing the unbound ALDUs can be separated by removing the solution and washing the wells with washing solution.

In the amplification step (c.) according to the method of the present invention the ALDUs bound to the target are amplified, in order to obtain high enough concentrations of the ALDUs so that they are useful for being applied in a functional screen. This amplifying step makes use of the ALDUs' intrinsic property to be amplifiable. For example phages displaying, e.g., an antibody or antibody fragment, which have been separated from the non-bound phages in step b), but are still bound to the cancer cell, can be amplified by first recovering the bound phages, for example by eluting the phages from the cancer cells and then using the recovered phage eluate to infect bacteria, e.g. *Escherichia coli*. The amplification of the phages in *Escherichia coli* then leads to a significant increase in total phage number, but in such a way, that the concentration of those individual phages, which were capable of binding to the cancer cells, is dramatically increased. According to a preferred embodiment the step of amplification is realized by either eluting the ALDU bound to a cancer cell, or by lysing a cancer cell under conditions where the ALDU remains amplifiable, and subsequent amplification. ALDUs bound to a cancer cells can be eluted from the cancer cells first, e.g. by use of solutions with low pH and/or high salt, as demonstrated in the Examples, and subsequently amplified, e.g. such that the eluted phages are used to infect *Escherichia coli* in order to produce large numbers of progeny phages. However, the elution step from the target, while it may be convenient, is not necessary, as, e.g., in the case of phage libraries even the phages still bound to a cancer cell, are capable of infecting *Escherichia coli* and thus capable of producing large numbers of identical progeny, and thus are amplifiable even when still bound to the cancer cell. Accordingly, the phages need not necessarily be removed from the target cell, as a phage still bound to a target cell can infect added bacteria and thus be amplified.

As another example, the mRNA of a ribosomal-display library, which is associated with the surface of a cancer cell by its attachment to a ribosome displaying the polypeptide corresponding to the mRNA can be directly used for RT-PCR, without the need of removing the intact ALDU from the target before amplifying the target.

Thus, a step in which the ALDU bound to a target is recovered from the target before amplifying the ALDU is an optional step.

Amplifying the ALDU can also consist in determining the chemical identity of the ligand of such ALDUs, which are bound to the cancer cell and then amplifying the ligands. That is to say, e.g., that in the case of a phage library, displaying an antibody or an antibody fragment, DNA encoding those ligands can be cloned from phages, which are bound to the cancer cell, e.g., by PCR, and the ligand, e.g., the antibody or antibody fragment, can then be produced recombinantly to yield sufficient amounts of the ligand to be useful for a functional screening assay. In such a way, not the ALDU itself is amplified, but the ligand displayed by the ALDU. This, however, is within the scope of the invention, as the aim of the amplification step is the generation of a ligand concentration high enough to be useful for a functional screening assay and this can be achieved by either amplifying the ligand or the ALDU displaying it.

In the identifying step (d.) according to the method of the present invention, an ALDU or a ligand derived from an ALDU, which had bound to a cancer cell is identified based on its effects on a biological function of Hsp90 to be tested in a functional screening assay. For such a functional screening assay, the ALDUs or ligands derived from them are advantageously individualized, such that a signal or a pattern from the functional screening assay is relatable to an individual ALDU or an individual type of ligand. This can be done, e.g. by filling separate wells of a multi-well plate with individual ligands each and then performing an assay for a desired biological function of Hsp90 in those individual wells.

In another example phages, which had bound to a cancer cell, and had been separated from unbound phages, can be individualized by infecting bacteria and plating the infected bacteria in, e.g. soft agar, so that individual plaques form, which represent clones of individual phages. Those individual plaques can then be tested for their effects in a biological screening assay for Hsp90 function. In such an assay, an individual plaque with an effect in the functional screening assay for Hsp90 function is identifiable. The ligand displayed by the phages of the plaque can then be identified, e.g. by sequencing the phage DNA of an isolated plaque, which represent a clone of a single phage, initially selected by its ability to bind to the cancer cell. Thus, in those cases where an ALDU itself is used in the functional screening assay, the identity of the ligand displayed by the ALDU can be determined, if desired.

In a preferred embodiment the ligand is capable to inhibit a biological function of Hsp90. For example, the biological function of Hsp90 can be invasion, or adhesion.

In another embodiment the ALDU or the ligand derived from an ALDU and used for the functional screening assay as in step d) of the method according the invention identifying an unmodified ligand according to the invention.

In still another embodiment of the invention the ALDUs or the ligands derived from an ALDU which are used for the functional screening assay according to step d) of the method of identifying a ligand according to the invention are chemically modified to increase their biological activity or endow the ALDU or the ligand with biological activity. As an example, one way to increase the biological activity of an ALDU or a ligand or to endow the ALDU or the ligand with biological activity is to use the ALDU or the ligand in combination with Chromophore-Assisted Laser Inactivation (CALI) as described earlier. CALI can also be used to further enhance the inhibitory effect of a ligand that has already a neutralizing and inhibitory effect by itself.

This makes also clear that the nature of the ligand displayed on the ALDU is not critical to identify suitable molecules, it is more the ability of the ALDU to be identifiable and amplifiable, which has influence on a successful screening for Hsp90 inhibiting molecules according to the invention.

However, as explained before, amplification of the ALDU can be achieved by increasing the number of an individual ALDU, but also by increasing the number of a ligand displayed by an individual ALDU. Since this can in principle also be achieved by an individual bead displaying a small chemical in combinatorial chemical libraries (see Ohlmeyer et al. (1993) Proc. Natl. Acad. Sci. USA 90, 10922-26; Liu et al. J. Am. Chem. Soc. (2002) 124, 7678-80; Liang et al Science (1996) 274, 1520-2) such bead-format libraries are also libraries of ALDUs. Small molecules can be synthesized on microsphere beads, which can be indexed with inert chemical tags. During each step of the synthetic scheme a tag molecule that encodes the step number and the chemical reagent used in that step is attached to the bead. This array of tags can then be used as a binary code to record the reaction history of each bead. The identified compound can then easily be synthesized in a bigger scale.

An ALDU used according to the invention is a biological ALDU whereby the information about its identity is stored as a nucleic acid, e.g. RNA or DNA. In a preferred embodiment the ALDU is selected from the group consisting of viruses useful for viral display, phages useful for phage display, bacteria useful for bacterial display, ribosomes useful for ribosome display, yeasts useful for yeast display and oligonucleotides useful for selection and amplification.

Phages useful for phage display can be all phages that can be obtained from culture and that are amenable to genetic engineering techniques and are capable of displaying a foreign ligand on their surface. Phage display has been disclosed in Smith et al. (1985) Science, 228, 1315-17, phage display of an antibody has been disclosed in WO 91/17271.

Bacteria useful for bacterial display are bacteria, which can be kept in culture, which are amenable to genetic engineering techniques and which are able to display a ligand on their surface. Examples for bacteria useful for bacterial display are disclosed in Dougherty et al., (1999) Protein Eng. 12, 613-21; and Westerlund-Wickstrom B. (2000) Int. J. Meth. Microbiol. 290, 223-30.

Ribosomes useful for ribosomal display have been disclosed in Shaffizel et al., (1999) J. Immunol. Methods 231, 119-35; and Willson et al., (2001). Proc. Natl. Acad. Sci. USA 98, 3750-5.

Oligonucleotides useful for selection/amplification (Selex) have been disclosed in Tuerk and Gold (1990) Science 249, 505-10, and Tuerk et al., (1992) Proc. Natl. Acad. Sci. USA 89, 6988-92.

However, also lower eukaryotes which can be cultured and are amenable for genetic engineering techniques and, thus, able to display a foreign ligand on their surface are useful as ALDUs, e.g. genetically modified yeast, as disclosed in Boder and Wittrup (2000) Methods Enzymol. 328, 430-44.

The method of the invention, the method of identifying a ligand of the invention comprises as the identification step d) a spatial separation of the different ALDUs of a pool of ALDUs and then the screening of the spatially separated ALDUs for their effect on a biological function of Hsp90 in such a way that the result obtained can be assigned to an individual ALDU. Spacial separation of the different ALDUs of a pool of ALDUs can be done, e.g., by filing separate wells of a multi-well plate with individual ligands each and then use those multi-well plates in a functional screening assay. If, e.g., in one well the biological function of Hsp90 is inhibited, then a ligand inhibiting said biological function of Hsp90 is identified, as the experimentator knows the identity of each ligand he put into each individual well.

In another preferred embodiment the method of identifying a ligand according to the invention can comprise the step of determining the identity of the ligand, wherein this determination step is achieved by sequencing the DNA of an identified ALDU, taking a PCR fingerprint of the nucleic acid of an identified ALDU or also, in the case of a ligand derived from an ALDU, by mass spectrometry of such a ligand. PCR fingerprinting of, e.g., phages is disclosed in Marks et al. (J. Mol. Biol. (1991) 222, 581-97). Mass spectrometrical analysis of a ligand, e.g. a polypeptide, is disclosed in Shevchenko et al. ((1996) Anal. Chem. 68, 850-58) or Spengler et al ((1992) Rapid. Commun. Mass. Spectrom. 6, 105-8.)

The method of identifying a ligand according to the invention may further comprise at least one additional step of screening ALDUs, e.g. wherein the screening is based on biochemical properties of the ALDUs. Such an additional screening step may comprise a method selected from the group consisting of flow cytometry, ELISA, immunoprecipitation, binding assays, immunohistochemical experiments, affinity studies, immunoblots and protein arrays. Biochemical properties can be determined by the size, the shape, the density, the charge density, the hydrophobicity, or the binding specificity of an ALDU or the ligand derived from an ALDU. The biochemical properties of the ALDU or the ligand derived from an ALDU form the basis of the applicability of the above-mentioned methods for screening the ALDUs. Flow cytometry is usually performed by labeling cells with a fluorescent dye and then passing those labeled cells in suspending medium through a narrow dropping nozzle so that each cell is in a small, separate droplet. A laser-based detector system is often used to excite the fluorescent dye and droplets with e.g. fluorescence-positive cells are registered.

In another preferred embodiment of the invention, the method of identifying a ligand of the invention can further comprise a substractive selection step. A substractive selection step is a step, which removes ALDUs with an undesired property. For example a substractive selection step can be affected by removing the ALDUs capable of binding to a control cell, if the property of binding to a control cell is undesired. By way of example, if one wants to select for ALDUs specific for cancer cells one could first select those ALDUs which bind to cancer cells, elute the bound ALDUs, e.g. phages, and then remove those ALDUs, which are capable of binding to non-cancer-cells, by for example contacting the pool of eluted ALDUs with non-cancer-cells and removing those ALDUs bound to the non-cancer-cells. The ALDUs remaining in the supernatant are then ALDUs specific for cancer cells and can then be used in functional screening assays according to the method of identifying a ligand of the invention.

In step e) the pool of ALDUs, e.g. phages, is enriched in ALDUs binding to Hsp90. Those ALDUs binding to Hsp90 can finally be identified in step f) by numerous methods known in the art.

In a preferred embodiment of the invention, the above method comprises instead of steps e) and f) the further steps of:

e) contacting ALDUs, e.g. isolated phages with recombinant Hsp90;

f) washing said Hsp90 with a buffered detergent and/or high salt solution; and g) eluting ALDUs, e.g. phages bound to Hsp90; and h) determining the identity of the ligand, e.g. an antibody or antibody fragment represented by said eluted ALDU, e.g. a phage.

The "detergent" used can be a detergent solution, preferably buffered, and can be Tween in a concentration of 0.001-0.5%, particularly 0.01-0.1%. "High salt" as used herein means a high salt solution, preferably buffered, and has an ionic strength of 10 mM-1M, particularly 20-500 mM, more particularly 50-350 mM, even more preferably 80-250 mM. Typical useful anions are, for example, chloride, citrate, phosphate, hydrogen phosphate or borate. Typical useful cations are, for example, sodium, potassium, lithium, calcium or magnesium.

Buffered solution in the above paragraph typically has a pH of 7-8. For example, DMEM or PBS, particularly with 1-20%, more particularly 5-15%, even more preferably about 10% FCS, can be used as buffers.

Isolation of cells with phages bound to them is effected by gentle centrifugation at g values from 200 to 300 for 3 to 20 minutes, particularly 5 to 10 minutes. Elution of bound phages, both to cells and to immobilized Hsp90, is effected by a wash with 2-100 mM, particularly 4-50 mM, more particularly 5-20 mM, even more preferably around 10 mM Glycine at a pH of from 0 to 2.5, particularly from 1 to 2.5, more particularly from 1.5 to 2.5.

Furthermore all the inhibitors of extracellular Hsp90 can be used according to the present invention to modulate and especially to reduce the activity and/or reduce the secretion of matrix metalloprotease (MMP).

The following examples, including experiments conducted and results achieved, are provided for illustrative purposes only and are not to be construed as limiting upon the present invention.

DESCRIPTION OF THE DRAWINGS

FIG. 6A, left first panel, shows localization of Hsp90α/β (Affinity Bioreagents #PA3012 & PA3-013) near the leading edge of HT-1080 cells. The middle panel in FIG. 6A shows the same localization near the leading edge using mAb 1.5.1. FIG. 6A, right panel, shows complete protein co-localization can be seen when the images are overlapped. This demonstrates that mAb 1.5.1 and Hsp90 recognize the same protein. Images were collected (Zeiss Axiovert 10 using a Neofluar 40-x/0.75 numerical aperture lens) using excitation filter sets at 546 and 480 and emission filter sets at 590 and 535 for rhodamine (red, Hsp90α/β) and FITC (green, mAb 1.5.1). Scale bars in images represent 10 μm.

FIG. 6B shows surface immunocytochemistry on HT-1080 cells using antibodies against β1-integrin (c), and Hsp90α (e) show distinct surface staining Negative controls [mouse secondary alone (a) and rabbit secondary alone (b)], α-actinin-4 (d), and Hsp90β (f) show no detectable surface staining Images were visualized using an Olympus BH-3, and collected using a SPOT digital camera (Digital Instruments).

FIG. 6C shows surface immunocytochemistry on MD-MDA231 adenocarcinoma cells using antibodies against β1-integrin (c), and Hsp90α (e) show distinct surface staining Negative controls [mouse secondary alone (a) and rabbit secondary alone (b)], α-actinin-4 (d), and Hsp90β (f) show no detectable surface staining Images were visualized using an Olympus BH-3, and collected using a SPOT digital camera (Digital Instruments).

FIG. 6D shows immunoblotting of HT-1080 conditioned media with Hsp90α and Hsp90β specific antibodies shows the extracellular location of Hsp90α, but not Hsp90β. Hsp90α is present in serum-free conditioned media from HT-1080 cells, but Hsp90 is absent.

FIG. 9 shows peptide matches from mass spectrometry analysis. Trypsinized peptide fragments from the mAb 1.5.1 immunoprecipitation were run on a Surveyor HPLC and LCO Deca Ion Trap mass spectrometer (ThermoFinnigan) with a 75 μM nanospray C18 column (New Objectives). The obtained PMF (peptide mass fragments) were used to search all entries for the species *Homo sapiens* in the NCBI and Swiss-Prot databases. The matched peptides cover 24% (172/732 residues) of Hsp90α and 33% (241/724 residues) of Hsp90β.

FIGS. 13A-13D show the vector map of the scFv display vector pXP10 and corresponding sequence. FIG. 13A shows the vector map of scFv display vector pXP10. FIG. 13B-13D shows the corresponding sequence, where the end of the sequence in FIG. 13B is continued at the beginning of the sequence in FIG. 13C, and the end of the sequence in FIG. 13C is continued at the beginning of the sequence in FIG. 13D.

FIGS. 14A-14D show the vector map of the scFv expression vector pXP14 and corresponding sequence. FIG. 14A shows the vector map of scFv display vector pXP14. FIG. 14B-14D shows the corresponding sequence, where the end of the sequence in FIG. 14B is continued at the beginning of the sequence in FIG. 14C, and the end of the sequence in FIG. 14C is continued at the beginning of the sequence in FIG. 14D.

FIGS. 15A-15B show the sequences for the construction primers for a mouse library. FIG. 15A shows tables for the cDNA primer sequences, VH forward and backward primers without restriction sites, and VL forward and backward primers without restriction sites. FIG. 15B shows tables for VH forward and backward primers (with restriction sites), and VL forward and backward primers (with restriction sites).

FIG. 16 shows the amino acid sequences (SEQ ID NO.: 1) (CDR3 region is underlined) and nucleotide sequence (SEQ ID NO.: 2) of scFv1

EXAMPLES

Example 1

Generation of Monoclonal Antibodies (e.g. mAb1.5.1)

Figure 1:
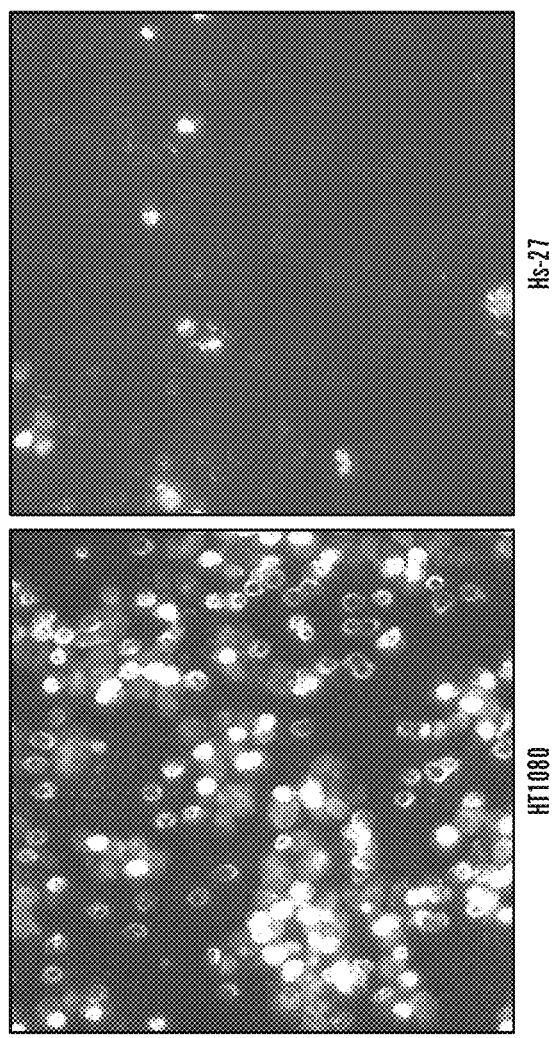
FIG. 1 shows the invasion of stained HT-1080 cells through a Matrigel coated 8 µm filter (left picture). The right picture shows invasion of stained HS-27 cells as a control. Fluorescence was quantified after six hours incubation at 37° C. Data presented are the mean of n=3 wells+/−SD.

Mice were immunized with either fixed or lysed HT-1080 cells twice over three months. For fixation, confluent ($1 \times 10^7$/

75 cm² flask) HT-1080 cells were washed once with PBS, then removed with PBS and scraping. Cells were resuspended by pipeting, centrifuged for 5 minutes at 220×g, and fixed with 10 mL of 2% paraformaldehyde for 10 minutes at 4° C. Cells were washed with PBS, then resuspended in 1 ML of PBS. Lysed cells were generated by trypsinizing confluent HT-1080 cells, washing once with PBS, then pelleting for 1 minute at 12000×g. Cells were then lysed in lysis buffer (0.67 Triton-X-100 in 0.33M Tris-HCl, pH 7.5) at room temperature for 5 minutes. Lysate was then centrifuged for 5 minutes at 12000×g. Triton-X-100 was removed by adding the lysate to PD-10 columns and eluting protein with 3.5 mL PBS. Protein was quantitated using Micro-BCA kit (Pierce), and 150 µg/mL/mouse was used for immunization.

Generation of hybridomas was performed as described previously (Harlow and Lane, 1988).

Hybridoma supernatants were first screened by fixing a confluent monolayer of HT-1080 cells (40,000 per well of a 96-well clear thin bottom plate) in 4% paraformaldehyde/PBS for 30 minutes at room temperature and then permeabilizing in 0.2% Triton-X-100 for 5 minutes. Following incubation with undiluted hybridoma supernatant, three 5 min 0.1% bovine serum albumin (BSA) in phosphate buffered saline (PBS) washes done. A FITC-labelled rabbit-anti-mouse secondary antibody was added for 1 hour at room temperature. The same 0.1% BSA/PBS washes were repeated and a tertiary FITC-labelled, goat-anti-rabbit antibody was added for 1 hour at room temperature. After a final round of washes, the cells were stored in PBS at 4° C. until imaging. Images were collected (Zeiss Axiovert 10 using a Neofluar 40X/0.75 numerical aperture lens) using excitation filter set at 480 and emission filter set at 535 for FITC. Cells were scored for staining compared to positive controls (anti-β1 integrin, Chemicon #MAB1963 and anti-gelsolin, Sigma #G4896) and negative controls (no primary antibody). The hybridomas that tested positive for HT-1080 binding were then tested for surface expression by surface immunocytochemistry. For surface protein immunocytochemistry, a confluent monolayer of HT-1080 cells (40,000 per well of a 96-well clear thin bottom plate) were incubated with hybridoma supernatant for 1 hour at 37° C./5% $CO_2$. After three 5 min 0.1% bovine serum albumin (BSA) in phosphate buffered saline (PBS) washes, the cells were fixed in 2% paraformaldehyde for 2 min. Another round of 0.1% BSA/PBS washes was performed, and a FITC-labelled rabbit-anti-mouse secondary antibody was added for 1 hour at room temperature. The same washes were repeated and a tertiary FITC-labelled goat-anti-rabbit antibody was added for 1 hour at room temperature. After a final round of washes, the cells were stored in PBS at 4° C. until imaging. Surface staining was visualized by microscopy on a Zeiss Axiovert 10 using a Neofluar 40X/0.75 numerical aperture lens. Images were collected using excitation filter set at 480 and emission filter set at 535 for FITC. Cells were scored for surface staining compared to a positive control (anti-β1 integrin, Chemicon #MAB1963 and anti-gelsolin, Sigma #G4896) and negative controls (no primary antibody).

Example 2

Construction of an Immune Library

Two BALB/c mice were each immunized intradermally with $2 \times 10^7$ paraformaldehyde fixed HT-1080 cells (human fibrosarcoma cell line; ATCC, CCL-121). Following the first immunization, the injections were repeated twice in a period of 39 days, the mice sacrificed and the spleens isolated and frozen in liquid nitrogen.

Total RNA was isolated using the RNeasy Midi Kit (QIAGEN #75142) as described by the manufacturer using half of each spleen preparation. The RNA concentration and purity was determined by a denaturing formaldehyde gel and photometric measurement.

cDNA was synthesized using 8.9 µg of freshly prepared RNA and 10 pmol of a primer mix IgG1-c, IgG2a-c, IgG2b-c, IgG3-c, VLL-c, VLK-c) using the Superscript™ II Kit (GibcoBRL Life Technologies #18064-014). These primers anneal to the RNA encoding the IgG heavy-chain (VH) genes and the light chain (VL) genes of the kappa and lambda family. VH genes were PCR amplified from 1 µl of cDNA using 36 individual combinations of 9 forward primers (M-VH1, M-VH2, M-VH3, M-VH4, M-VH5, M-VH6, M-VH7, M-VH8, M-VH9) and 4 back-ward primers (M-JH1, M-JH2, M-JH3, M-JH4) without restriction sites. VL genes were PCR amplified with one primer mix (M-VK1, M-VK2, M-VK3, M-VK4, M-VL1, M-JK1, M-JK2, M-JK3, M-JL1) without restriction sites. PCR products were gel-purified (QIAquick Gel Extraction Kit, #28706) and reamplified using individual combinations of 9 forward primers (MVH1 SfiI MVH2 SfiI MVH3 SfiI, MVH4 SfiI, MVH5 SfiI, MVH6 SfiI, MVH7 SfiI, MVH8 SfiI, MVH9 SfiI) and 4 backward primers (M-JH1 SalI, M-JH2 SalI, M-JH3 SalI, M-JH4 SalI) with restriction sites for VH and one primer mix (M-VK1 ApaLI, M-VK2 ApaLI, M-VK3 ApaLI, M-VK4 ApaLI, M-VL1 ApaLI, M-JK1 NotI, M-JK2 NotI, M-JK3 NotI, M-JL1 NotI) with restriction sites for VL. PCR products were gel-purified (QIAquick Gel Extraction Kit, #28706) and cloned into the phage display vector pXP10 using the restriction sites SfiI/SalI for VH and ApaLI/NotI for VL. The ligation mix was transfected into E. coli TG-1 by electroporation resulting in a library size of $10^7$ independent clones (phages) expressing different single chain antibody fragments (scFv).

Example 3

Selection and Screening of scFv (Selection on Fixed Cells)

Single chain Fv were selected from a phage display library generated from mice immunized with fixed HT-1080 cells. The library was generated using the phage display vector pXP10.

Phages expressing scFv with high affinity to tumor cells were selected as follows: HT-1080 cells were harvested with 0.05% EDTA, fixed with paraformaldehyde, diluted to $1 \times 10^7$ cells/ml in PBS and immobilized onto wells of a 96 well UV cross-link plate (Corning Costar). The wells of the UV cross-link plate were blocked with 5% Skim Milk Powder (#70166, Fluka) in PBS (MPBS). $10^{12}$ cfu (colony forming units) of phage library/$10^6$ cells were pre-blocked for 1 hour at 25° C. with MPBS and subsequently incubated for 1.5 hour at room temperature (RT) with the cells. The wells of the UV cross-link plate were washed six times with PBS+0.05% Tween-20 followed by six washes with PBS. Bound phage were eluted by the addition of 10 mM Glycine pH 2.2, and neutralized with 1 M Tris/HCl pH 7.4. Typically, between $10^3$ and $10^6$ cfu were eluted in the 1ˢᵗ round of selection, thus the diversity of the enriched repertoire is decreased compared to the original repertoire. The eluate containing the enriched repertoire was amplified by infecting exponentially growing E. coli TG1. Phagemid containing E. coli were selected and propagated by overnight (o/n) growth at 30° C. on LB agar plates supplemented with 100 µg/ml ampicillin and 1% glucose. Following this step, the enriched repertoire can either be amplified as a polyclonal pool and used for further rounds of selection in an iterative manner until convergence to desired properties is achieved or be spatially separated and screened on a single clone level. Phage particles for the next round of selection were produced by super-infecting exponentially growing cultures of the previous round of selection with helper phage VCS-M13 (Stratagene, La Jolla, Calif.) and growing the cultures overnight at 20° C. in 2×TY supplemented with 100 µg/ml ampicillin (amp) and 50 µg/ml kanamycin (kan). Selection ready phage were precipitated with 0.5 M NaCl/4% PEG-6000 from the cleared bacterial supernatant and re-suspended in PBS. One round of selection was performed, followed by screening on a single clone level as described in Example 4.

Example 4

Selection and Screening of scFv (Screening on Fixed Cells)

For screening, the genes encoding the selected scFv, contained in the phage display vector, were re-cloned to the expression vector pXP14. This vector directs the expression of scFv in fusion with a Strep-tag and E-tag and does not contain a filamentous phage gene-3. Expression vector containing E. coli TG1 from single colonies were grown in individual wells of a micro titer plate so that each well contains only one scFv clone. The bacteria were grown at 30° C. in 2×TY supplemented with 100 µg/ml ampicillin and 0.1% glucose in 96-well micro titer plates (#9297, TPP) until an $OD_{600}$ of 0.7. Expression was induced with IPTG at a final concentration of 0.5 mM and continued at 25° C. overnight. Single chain Fv containing cleared lysates were prepared by addition of hen-egg lysozyme (#L-6876, Sigma) to a final concentration of 50 µg/ml for 1 hour at 25° C. and centrifugation for 15 minutes at 3000×g. Prior to the screening ELISA, the cleared lysates were blocked by the addition of an equal volume of DMEM+10% FCS for 1 hour. For the screening ELISA, HT-1080 cells were harvested with 0.05% EDTA, fixed with paraformaldehyde, diluted to $1\times10^7$ cells/ml in PBS and immobilized onto wells of a 96 well UV cross-link plate (Corning Costar). The wells of the UV cross-link plate were blocked with MPBS and the scFv containing blocked cleared lysates added for 1.5 hours at 25° C. The plates were washed 2× with PBS+0.1% Tween-20 and 1× with PBS, incubated with HRP conjugated α-E-tag (#27-9413-01, Pharmacia Biotech; diluted 1:5000 in MPBS with 0.1% Tween-20) for 1 hour, washed 3× with PBS+0.1% Tween-20 and 3× with PBS, developed with POD (#1 484 281, Roche) and signals read at 370 nm.

Positive clones were retested against HT-1080 cells and control human fibroblasts Hs-27 (ATCC CRL-1634) using the ELISA screening procedure described above and preserved in glycerol stocks. In a typical screen, 2760 (30×92) clones were screened for binding to HT-1080 cells with 5% positives defined as clones giving a background subtracted signal>0.1. 155 positive clones were retested for specific binding to HT-1080 cells compared to the Hs-27 control cells with 28% positives defined as clones giving a background subtracted signal on HT-1080 of at least twice the value of the signal on Hs-27 control cells.

Example 5

Sequencing and Large Scale Expression

Sequencing of scFv1 and its genes was performed by Sequiserve GmbH, Vaterstetten, Germany using the primer pXP2 Seq2 (5'-CCCCACGCGGTTCCAGC-3' (SEQ ID NO: 55) and pXP2 Seq1 (5'TACCTATTGCCTACGGC-3' (SEQ ID NO: 56). The amino acid sequence and nucleotide sequence are shown in the Figures.

Unique clones identified by sequencing were streaked out from glycerol stocks onto LB/Amp (100 µg/ml)/1% Glucose Agar plates and incubated o/n at 30° C. 10 ml LB/Amp/Glu (1%) media were inoculated with a single colony and grown o/n at 30° C. and 200 rpm shaking. The next morning the overnight cultures were placed on ice until inoculation of 1 L 2×TY media supplemented with 100 µg/ml Ampicillin and 0.1% Glucose in 2 L Erlenmeyer-flasks. The cultures were grown at 25° C. shaking until an $OD_{600}$ 0.5-0.6 was reached and then induced with IPTG 0.1 mM final concentration. Fresh ampicillin was added to 50 µg/ml and incubation was proceeded at 22° C. o/n shaking. In the morning the cultures were centrifuged at 5000×g for 15 minutes at 4° C., supernatants discarded and the pellets re-suspended carefully on ice with a pipette in 10 ml pre-cooled PBS-0.5 M Na buffer containing protease inhibitors complete (#1697498, Roche). After resuspension was completed, bacterial suspensions were transferred to 20 ml oak-ridge centrifuge tubes and hen-egg lysozyme (#L-6876, Sigma) added to a final concentration of 50 µg/ml for 1 hour on ice. The lysed bacteria were centrifuged at 20000×g for 15 minutes at 4° C. and the supernatants (lysate) transferred to a 15 ml plastic tube. For affinity purification the lysates were loaded with 1 ml/min onto 1 ml StrepTactin (#2-1505-010, IBA) columns equilibrated with 10 column volumes (CV) PBS-0.5 M Na buffer via a parallel protein purification system. After a 10 CV wash with PBS the elution was done with 5 CV PBS/5 mM Desthiobiotin (#D-1411, Sigma) and 1 ml fractions collected. The fractions were measured at $UV_{280}$, protein containing fractions were pooled and concentrated with Amicon Ultra Centrifugal Filter Devices 10.000 MWCO (#UFC801024, Millipore) at 4700× g. The concentrated scFv were checked on 12% Bis-Tris SDS-PAGE gels stained with Coomassie Blue for purity and frozen in aliquots with 20% glycerol at −80° C.

Example 6

FACS Analysis for Tumor Cell Specific Binding

Figure 8:
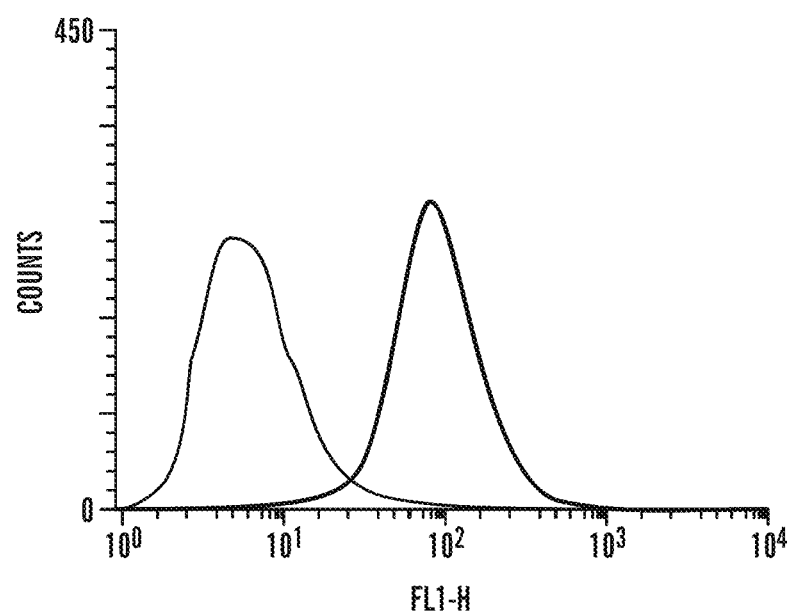
FIG. 8 shows a result of FACS analysis. The binding activity of scFv1 to HT-1080 cells (bold line) and to HS-27 cells (thin line) as control is illustrated.

To test the ability of purified anti HT-1080 scFv to bind specifically to target cells, we performed a fluorescence-activated cell sorter (FACS) analysis using HT-1080 cells (ATCC CCL-121) and Hs-27 cells ($10^6$ cells/ml) as control cell line (see Figures). Cells were incubated with 10 µg/ml of pure scFv in CellWash (BD (Becton, Dickinson and Company) #349524) for 20 min at 4° C., washed, and bound scFv's were detected with a secondary FITC labeled anti E-tag mab (Amersham #27-9412-01). Samples were washed and analyzed on a Becton Dickinson FACSscan. FIG. 8 shows the log fluorescence intensity (FL1-H; x-axis) versus the relative cell numbers (counts; y-axis) for cells reacting with scFv1. The thin line represents the control cell line (HS-27) and the bold line the HT-1080 cells. scFv1 specifically stains the tumor cell lines with up to 10 fold higher signal compared to the control cell line.

Example 7

Labeling of scFv with FITC scFv were labeled with fluorescein isothiocyante (FITC) (Molecular Probes, Eugene, USA #F1906) by the following method: Aliquots of a 10 mg/ml solution of FITC in dry dimethyl sulfoxide were added to 100 μg of scFv1 dissolved in PBS/0.5M $NaHCO_3$, pH 9.5 in a ratio of 30:1 (FITC: scFv1). The sample was incubated for two hours at room temperature with agitation, free FITC was separated using desalting columns (2 Micro Spin G-25, Pharmacia 27-5325-01). The ratio of labeling was determined via mass spectrometry and via UV/VIS spectroscopy, whereby the protein concentration was calculated at 280 nm and the FITC concentration at 494 nm.

Example 7.1

Labeling of mAb1.5.1 with FITC

A solution of freshly made 10 mg/mL FITC (Molecular Probes, Eugene, USA #F1906) in dry dimethyl sulfoxide was added in a 1:5 ration with purified mAb 1.5.1 antibody (T-gel Absorbant, Pierce Biotechnology #20500). An equal volume of 0.5M $NaHCO_3$, pH 9.5 was added to the reaction, and the reaction was incubated with rocking for two hours at room temperature. Free FITC was separated using a desalting column (PD-10, Amersham #17-0851-01). The ratio was determined by calculating the FITC concentration by VIS spectroscopy at 494 nm and assuming complete protein recovery from the labeling.

Example 8

Invasion Assay for Identification of Inhibitory Antibody Fragments

The ChemoTx® system (Neuro Probe Inc. #106-8, Gaithersburg) is used as a disposable chemotaxis/cell migration chamber in a 96 well format with an 8 μm filter Track etched Polycarbonate pore size, 5.7 mm diameter/site.

13.3 μl of 0.3 mg/ml Matrigel (Matrigel is a solubilized basement membrane preparation extracted from the Engelbreth-Holm-Swarm (EHS) mouse sarcoma, a tumor rich in extracellular matrix proteins. Its major component is laminin, followed by collagen IV, heparan sulfate proteoglycan, entactin and nidogen. It also contains TGF-β fibroblast growth factor, tissue plasminogen activator, and other growth factors which occur naturally in the EHS tumor) (Becton Dickenson, BD #356234) diluted in Dulbeccos PBS (Gibco #14040-091) is applied on the membrane filter of the 96-well plate on row B-H and on row A 1.2 μg/site of collagen S type I (Roche #10982929) is diluted in 0.05 M HCl (Sigma #945-50) and is incubated over night at 20° C. in a desiccator for gelation. HT-1080 cells are grown to 70-80% confluence in DMEM supplemented with GlutamaxI (862 mg/l (Gibco #31966-021) with 10% FCS (Gibco #10270106). The cells are washed 2× with DMEM/GlutamaxI/0.1% BSA (Sigma #A-7030) then labeled in situ with Bisbenzimide H 33342 (Sigma #B-2261) are diluted 1:100 in DMEM/GlutamaxI/0.1% BSA for 15 min at 37° C., 7.5% $CO_2$. Cells are washed 2× with DMEM/GlutamaxI/0.1% BSA and are loaded with DMEM/GlutamaxI/0.1% BSA for 15 min at 37° C., 7.5% $CO_2$ for recovering. After washing 2× with PBS w/o $Ca^{2+}$, $Mg^{2+}$ (Gibco, 10010-015), the cells are detached with 0.5 mM EDTA (Sigma #E8008), are collected with Dulbeccos PBS/0.1% BSA/10 mM Hepes (Gibco #15630-056), are washed 2× with Dulbeccos PBS/0.1% BSA/10 mM Hepes, are suspended in Dulbeccos PBS/0.1% BSA/10 mM Hepes and are diluted to $6.7 \times 10^6$ cells/ml with Dulbeccos PBS/0.1% BSA/10 mM Hepes. $6.7 \times 10^6$ cells/ml are incubated 1:1 with 40 μg/ml of a control scFv as a negative control for inhibition of invasion and with HT-1080 specific scFv for 1 h on ice.

After dilution to $6.7 \times 10^5$ cells/ml with DMEM/GlutamaxI/0.1% BSA, HT-1080 cells and HT-1080 cell/scFv dilutions are pipetted in triplicate onto the chemotaxis chamber (row B-H) at a density of $3.4 \times 10^4$ cells/well and are incubated for 6 h at 37° C., 7.5% $CO_2$. DMEM/GlutamaxI with 5% FCS is used as a chemo attractant in the lower chamber. A standard curve from $1 \times 10^4$ to $4 \times 10^4$ cells/site is performed on collagen S type I coated row A of the chemotaxis chamber. DMEM/GlutamaxI/0.1% BSA is used in the lower chamber (cells are not migrating). After scraping the non-migrating cells from the top of the membrane (except the Standard curve on row A) fluorescence of cells, which migrated through the membrane (not migrated in case of the Standard curve), is measured on the Fluostar Galaxy (bMG) microplate reader using excitation/emission wavelengths of 370/460 nm.

Example 9

Invasion Assay for Target Identification with CALI

This Example is in general identical to Example 8, except for the use of FITC-labeled scFv (see, Example 7 for labeling) and the integration of the CALI process within the invasion assay.

The ChemoTx® system (Neuro Probe Inc. #106-8, Gaithersburg) was used as a disposable chemotaxis/cell migration chamber in a 96 well format with an 8 μm filter Track etched Polycarbonate pore size, 5.7 mm diameter/site.

13.3 μl of 0.3 mg/ml Matrigel (see Example 8) diluted in Dulbeccos PBS (Gibco #14040-091) was applied on the membrane filter of the 96-well plate on row B-H and on row A 1.2 μg/site of collagen S type I (Roche #10982929) was diluted in 0.05 M HCl (Sigma #945-50) and was incubated over night at 20° C. in a desiccator for gelation. HT-1080 cells were grown to 70-80% confluence in DMEM supplemented with GlutamaxI (862 mg/l (Gibco #31966-021) with 10% FCS (Gibco #10270106). The cells were washed 2× with DMEM/GlutamaxI/0.1% BSA (Sigma #A-7030) then labeled in situ with Bisbenzimide H 33342 (Sigma #B-2261) and were diluted 1:100 in DMEM/GlutamaxI/0.1% BSA for 15 min at 37° C., 7.5% $CO_2$. Cells were washed 2× with DMEM/GlutamaxI/0.1% BSA and loaded with DMEM/GlutamaxI/0.1% BSA for 15 min at 37° C., 7.5% $CO_2$ for recovering. After washing 2× with PBS w/o $Ca^{2+}$, $Mg^{2+}$ (Gibco, 10010-015), the cells were detached with 0.5 mM EDTA (Sigma #E8008), collected with Dulbeccos PBS/0.1% BSA/10 mM Hepes (Gibco #15630-056), washed 2× with Dulbeccos PBS/0.1% BSA/10 mM Hepes, suspended in Dulbeccos PBS/0.1% BSA/10 mM Hepes and diluted to $6.7 \times 10^6$ cells/ml with Dulbeccos PBS/0.1% BSA/10 mM Hepes. $6.7 \times 10^6$ cells/ml were incubated 1:1 with 40 μg/ml of FITC-labelled anti-beta1 integrin monoclonal antibody (JB1, Chemicon #MAB1963) as a control for inhibition of invasion after CALI and with HT-1080 specific FITC labelled scFv for 1 h on ice. $1.3 \times 10^5$ HT-1080 cells/well or HT-1080 cell/scFv or Ab dilution were pipetted in triplicate in two 96-well plate, black, ultra thin clear flat bottom special optics (Costar #3615). One plate was kept on ice in the dark while the other plate was irradiated on an ice block with continuous wave laser at 488 nm (0.5 W, 30 sec). After dilution to $6.7 \times 10^5$ cells/ml with DMEM/GlutamaxI/0.1% BSA, HT-1080 cells and HT-1080 cell/scFv dilutions were pipetted in triplicate (non irradiated triplicate beside irradiated triplicate) onto the chemotaxis chamber (row B-H) at a density of $3.4 \times 10^4$ cells/well and incubated for 6 h at 37° C., 7.5% $CO_2$. DMEM/GlutamaxI with 5% FCS was used as chemo attractant in the lower chamber. A standard curve from $1 \times 10^4$ to $4 \times 10^4$ cells/ site was performed on collagen S type I coated row A of the chemotaxis chamber. DMEM/GlutamaxI/0.1% BSA was used in the lower chamber (cells were not migrating). After scraping the non-migrating cells from the top of the membrane (except the Standard curve on row A) fluorescence of cells, which had migrated through the membrane (not migrated in case of the Standard curve), was measured on the Fluostar Galaxy (bMG) microplate reader using excitation/emission wavelengths of 370/460 nm. In a general experiment, a value of 45000 corresponded to 100% migrated cells.

Figure 3:
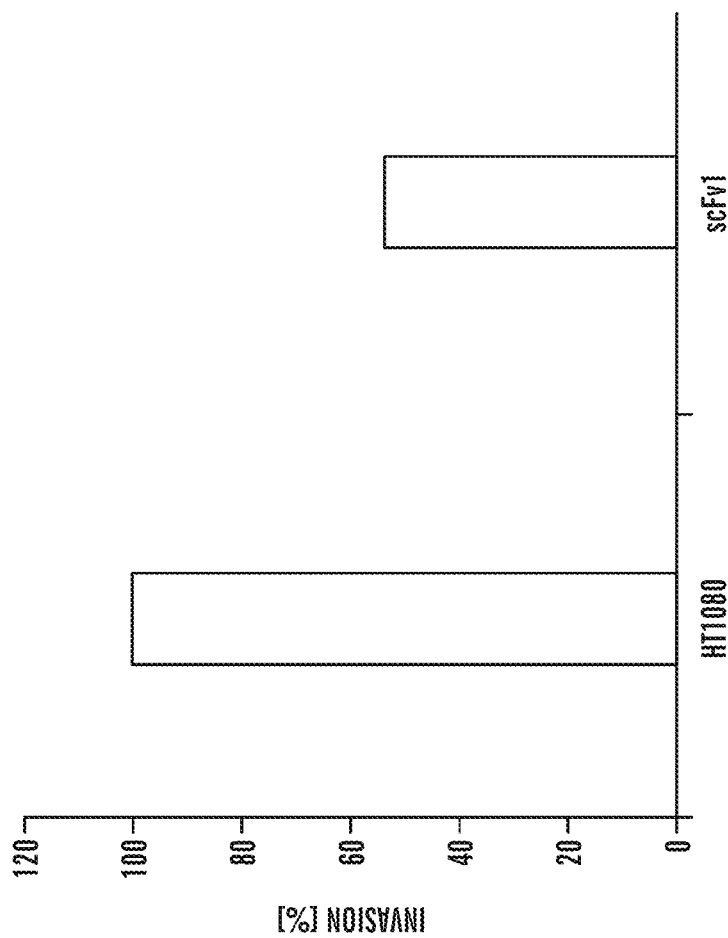
FIG. 3 shows the inhibitory effect of scFv1 on the invasion of HT-1080 cells. Invasion was determined in a chemotaxis assay with a Matrigel coated cell migration chamber after light irradiation (with CALI). The invasion of HT-1080 cells in the absence of any inhibitory molecule was used as a control (left bars). scFv1 inhibited the invasion of HT-1080 cells by about 46% (p-value<0.05).
Figure 4:
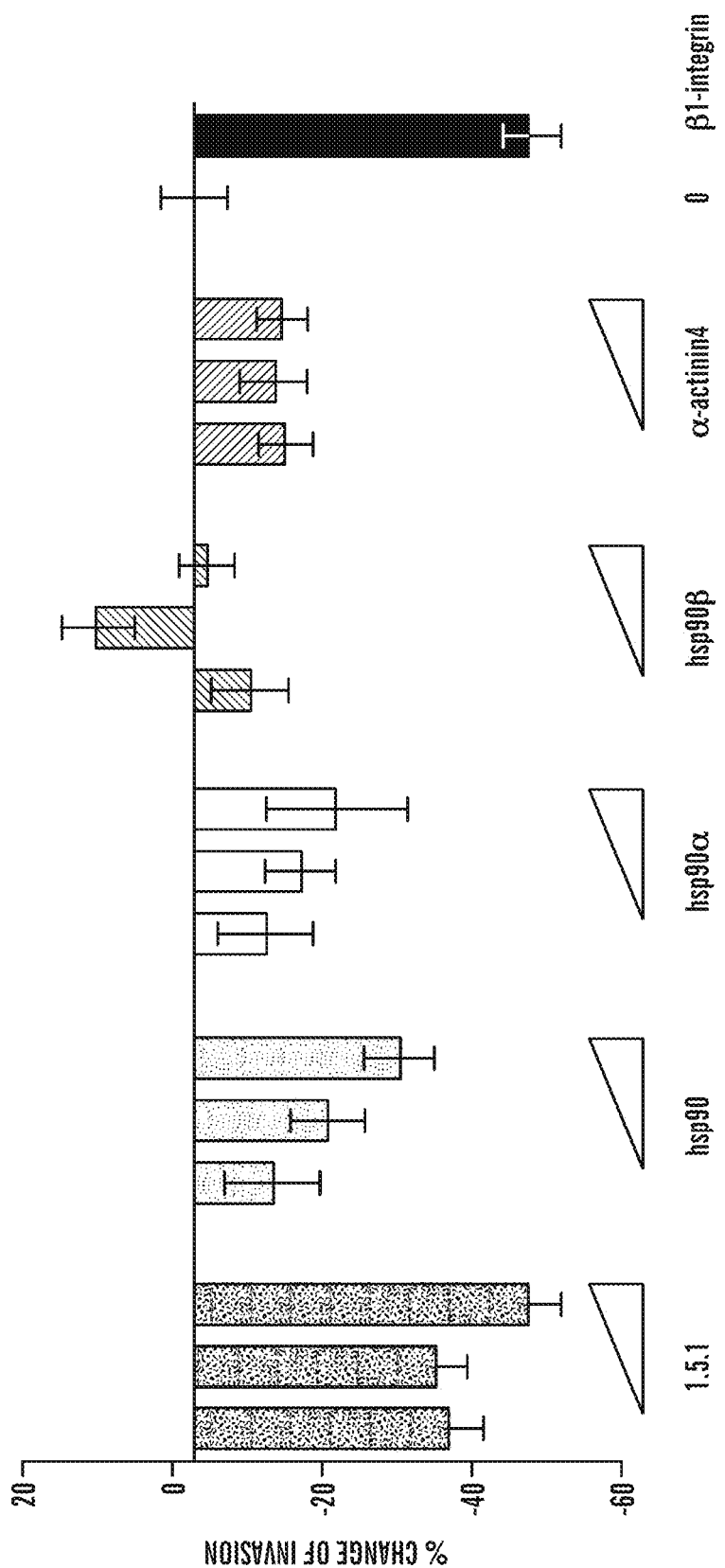
FIG. 4 shows a correlation of the inhibition of invasion with the antibody concentration. Antibodies specific for Hsp90, Hsp90α, Hsp90β, (all Stressgen), alpha-actinin-4 (Martin R. Pollak, Children's Hospital, Boston, Mass.) and mAb 1.5.1 were FITC-labelled and tested in the invasion assay after light irradiation at 3 concentrations (10 µg/mL, 20 µg/mL, and 40 µg/mL). Positive control β1-integrin (Chemicon, 20 µg/mL) and negative control (0, no antibody) are also shown. mAb 1.5.1, Hsp90, and Hsp90α antibodies all demonstrated concentration-dependent inhibition of invasion, while Hsp90 and alpha-actinin-4 did not. Each bar is normalized to dark control and represents the mean.+−.s.e.m of at least 2 experiments in triplicate.
Figure 5:
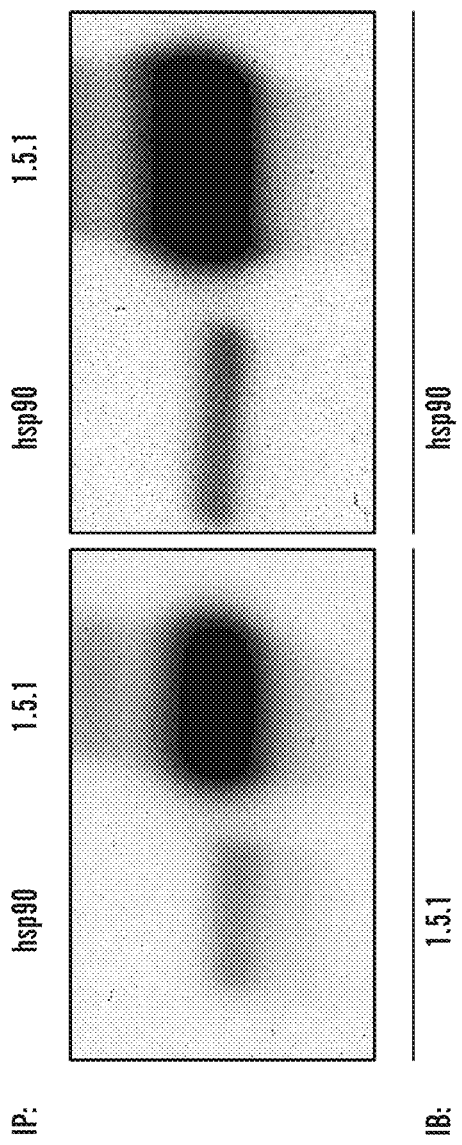
FIG. 5 shows the result of immunoprecipitation experiments. mAb 1.5.1 or an anti-Hsp90 antibody (Stressgen #SPA-830) was incubated with lysates of HT-1080 cells. The immuno-complexes were separated by SDS-PAGE and immunoblotted with mAb1.5.1 or the anti-Hsp90 antibody. The same specific band is recognized by both antibodies, indicating that both antibodies bind the same protein.
Figure 6A:
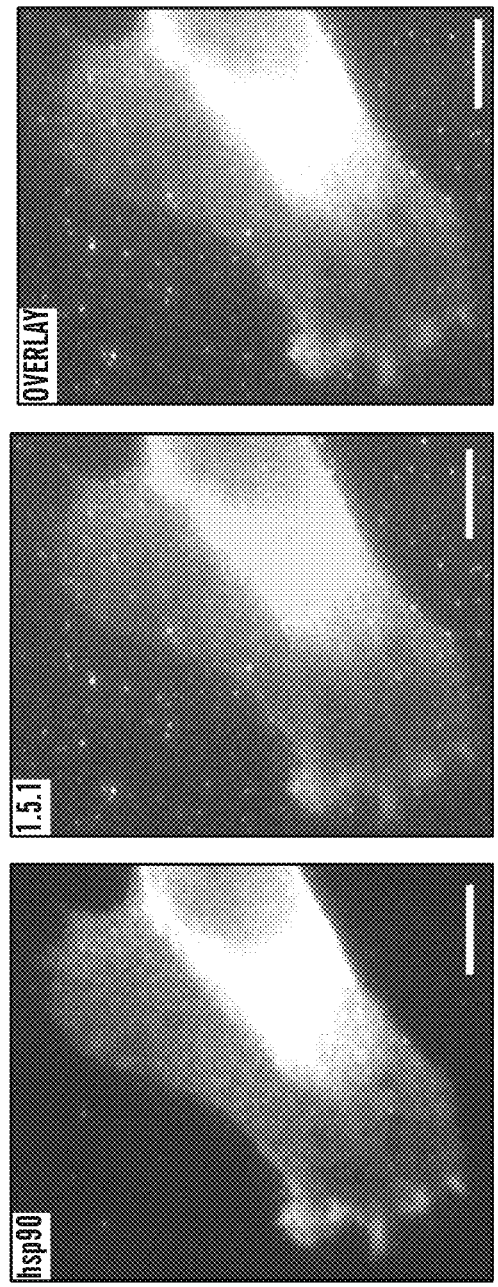
FIGS. 6A-6D show co-immunocytochemistry of Hsp90 and mAb 1.5.1.
Figure 6B:
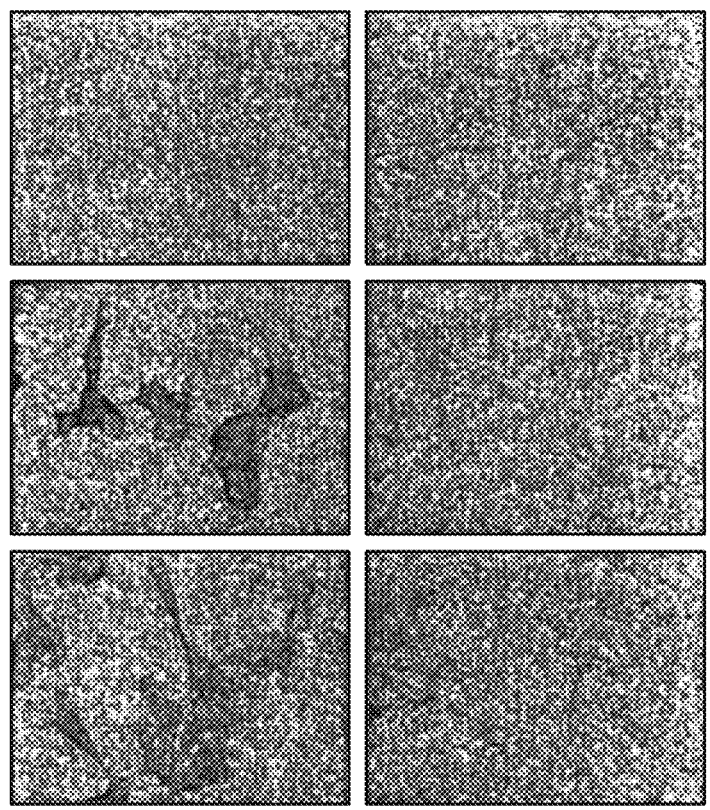
Figure 6C:
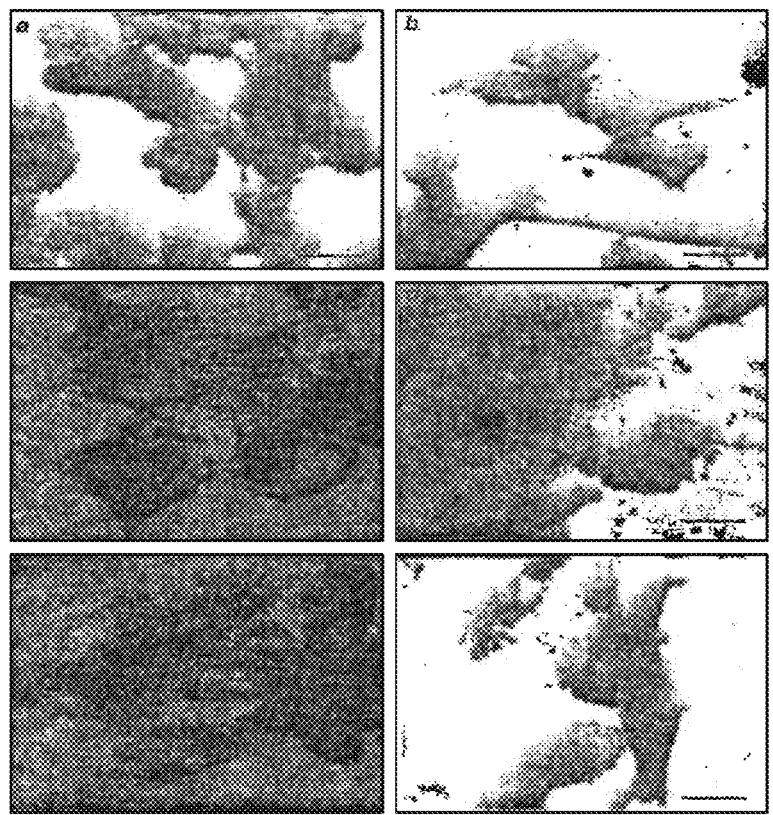
Figure 6D:
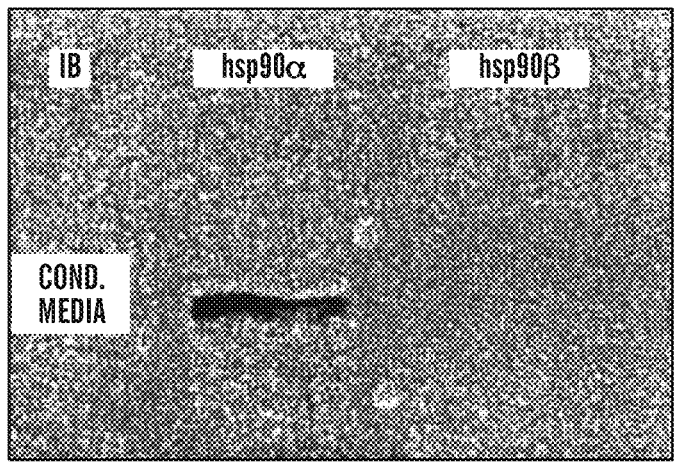

The invasion phenotype of HT-1080 cells was assessed by comparing their relative ability to invade tumor extracellular matrix (Matrigel) using the Transwell culture system described above. scFv1 showed after CALI an inhibitory effect of 46% on the invasion of the HT-1080 cells. The result of the invasion assay with CALI is shown in FIG. 3. FIG. 3 shows that CALI converts scFv1 in an inhibitory antibody fragment.

Example 9.1

Invasion Assay with Antibodies (e.g. mab 1.5.1) for Target Identification with CALI The ChemoTx® system (Neuro Probe Inc. #106-8, Gaithersburg) was used as a disposable chemotaxis/cell migration chamber in a 96 well format with an 8 µm filter Track etched Polycarbonate pore size, 5.7 mm diameter/site.

Figure 2:
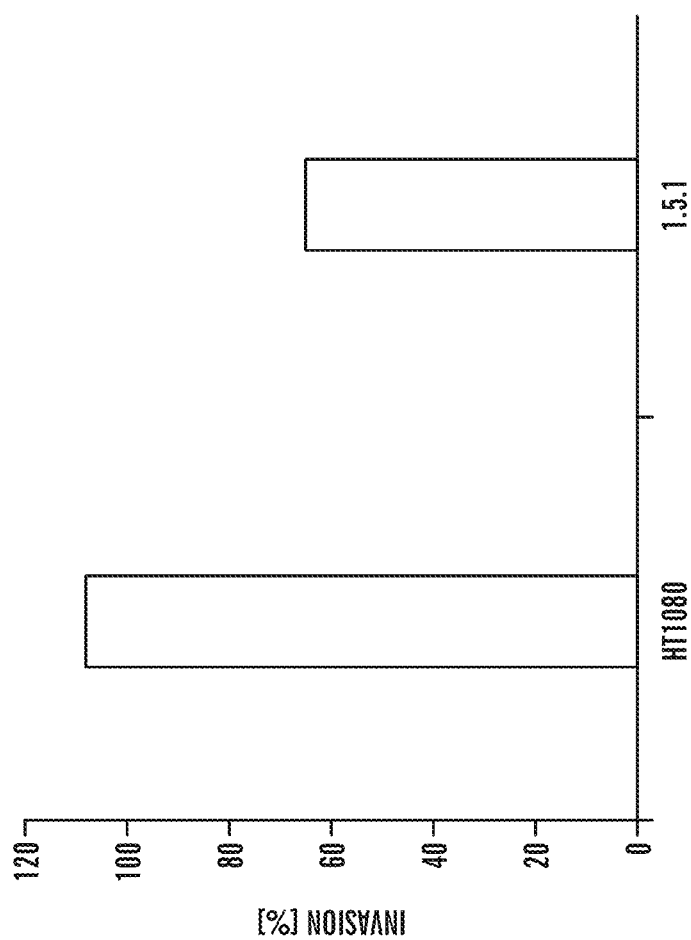
FIG. 2 shows the inhibitory effect of mAb1.5.1 on the invasion of HT-1080 cells. Invasion was determined in a chemotaxis assay with a Matrigel coated cell migration chamber after light irradiation (with CALI). The invasion of HT-1080 cells in the absence of any inhibitory molecule was used as a control (left bar). mAb 1.5.1 inhibited the invasion of HT-1080 cells by about 35% (p-value<0.001).

13.3 µl of 0.3 mg/ml Matrigel (see Example 8) diluted in cold Dulbeccos PBS (Gibco #14040-091) was applied on the membrane filter of the 96-well plate on row B-H and on row A 0.3 µg/site of mouse collagen, type IV (Becton-Dickenson #354233) was diluted in 0.05 M HCL (Sigma #945-50) and was incubated over night at 20° C. in a desiccator for gelation, HT-1080 cells were grown to 70-80% confluence in DMEM supplemented with MEM non-essential amino acids (IX, Gibco #11140050) and Penicillin/Streptomycin (1×, Gibco #15140122) with 10% FBS (Hyclone #SH30070.03). The cells were washed 1× with DMEM/MEM non-essential amino acids/0.1% BSA/MEM amino acids/Penicillin-Streptomycin (BSA, Sigma #A-7030) then labeled in situ with 3 µM Cell Tracker Orange (Molecular Probes #C-2927) in DMEM/MEM non-essential amino acids/0.1% BSA/MEM amino acids/Penicillin-Streptomycin for 15 min at 37° C., 7.5% CO2. Cells were washed 1× with DMEM/MEM non-essential amino acids/0.1% BSA/MEM amino acids/0.1% BSA/MEM amino acids/Penicillin-Streptomycin for 15 min at 37° C., 7.5% CO2 for recovering. After washing 1× with Hanks Bal-anced Salt Solution (HBSS) w/o Ca2+, Mg2+ (Gibco #14170112), the cells were detached with Versene (Gibco #15040066), collected with HBSS/MEM non-essential amino-acids/0.1% BSA/MEM amino acids/Penicillin-Streptomycin (HBSS, Gibco+14025092), washed 2× with HBSS/MEM non-essential amino acids/0.1% BSA/MEM amino acids/Penicillin-Streptomycin, suspended in HBSS/MEM non-essential amino acids/0.1% BSA/MEM amino acids/Penicillin-Streptomycin and diluted to 8×106 cells/ml with HBSS/MEM non-essential amino acids/0.1% BSA/MEM amino acids/Penicillin-Streptomycin. 8×106 cells/ml were incubated 1:1 with 40 µg/ml of FITC-labeled anti-beta 1 integrin monoclonal antibody (JB1, Chemicon #MAB1963) as a control for inhibition of invasion after CALI and with mAbs for 1 h on ice. 3×105 HT-1080 cells/well or HT-1080 cell/mAbs were pipetted in triplicate in two clear 96-well plates (Costar #3370). One plate was kept on ice in the dark while the other plate was irradiated on ice block with 300 W blue-filtered light (Roscolux, #69, Brilliant Blue) for one hour. After dilution to 8×105 cells/ml with DMEM/MEM non-essential amino acids/0.1% BSA/MEM amino acids/Penicillin-Streptomycin, HT-1080 cells and HT-1080 cells/mAbs dilutions were pipetted in triplicate (non-irradiated triplicate beside irradiated triplicate) onto the chemotaxis chamber (row B-H) at a density of 4×104 cells/well and incubated for 6 h at 37° C., 7.5% CO2, DMEM with 5% FCS was used as a chemoattractant in the lower chamber. A standard curve from 1×104 to 4×104 cells/site was performed on mouse collagen IV coated row A of the chemotaxis chamber. DMEM/MEM non-essential amino acids/0.1% BSA/MEM amino acids/Penicillin-Streptomycin was used in the lower chamber (cells were not migrating). After scraping the non-migrating cells from the top of the membrane (except the Standard curve on row A) fluorescence of cells, which had migrated through the membrane (not migrated in case of the Standard curve), was measured on the Tecan Spectrafluor Plus fluorescence plate reader (excitation: 544, emission: 590 nm). A positive control which recognizes β1 integrin (data not shown) and mAb 1.5.1 both showed a significant ($p<0.01$, unpaired t-test) reduction of invasion after exposure to light (data shown in FIG. 2). The negative control (no antibody) showed no reduction. Each bar is normalized to the negative control and represents the mean±s.e.m. of two experiments in triplicate.

Example 10

Cell-Matrix Adhesion Assay 96-well plates (TPP #9296) (cell culture treated) were coated in Row B-H with collagen S type I 1 µg/well (Roche #10982929) in Dulbeccos PBS (Gibco #14040-091) and in Row A well 10-12 were coated with 2% BSA (Sigma #A-7030)/Dulbeccos PBS at 4° C. over night. The plate was washed with Dulbeccos PBS, blocked Row B-H and Row A well 10-12 with 2% BSA/Dulbeccos PBS for 1 h at 37° C. and washed again with Dulbeccos PBS. HT-1080 cells were grown to 70-80% confluence in DMEM supplemented with GlutamaxI (862 mg/l (Gibco #31966-021) with 10% FCS (Gibco #10270106). The cells were washed 2× with DMEM/GlutamaxI/0.1% BSA (Sigma #A-7030) then labeled in situ with Bisbenzimide H 33342 (Sigma #B-2261) were diluted 1:100 in DMEM/GlutamaxI/0.1% BSA for 15 min at 37° C., 7.5% $CO_2$. Cells were washed 2× with DMEM/GlutamaxI/0.1% BSA and loaded with DMEM/GlutamaxI/0.1% BSA for 15 min at 37° C., 7.5% $CO_2$ for recovering. After washing 2× with PBS w/o $Ca^{2+}$, $Mg^{2+}$ (Gibco, 10010-015), the cells were detached with 0.5 mM EDTA (Sigma #E8008), collected with Dulbeccos PBS/0.1% BSA/10 mM Hepes (Gibco #15630-056), washed 2× with Dulbeccos PBS/0.1% BSA/10 mM Hepes, suspended in Dulbeccos PBS/0.1% BSA/10 mM Hepes and diluted to $6.7×10^6$ cells/ml with Dulbeccos PBS/0.1% BSA/10 mM Hepes. $6.7×10^6$ cells/ml were incubated 1:1 with 40 µg/ml of FITC-labeled anti-beta1 integrin monoclonal antibody (JB1, Chemicon #MAB1963) as a control for inhibition of adhesion after CALI and with HT-1080 specific FITC labeled scFv for 1 h on ice. $1.3×10^5$ HT-1080 cells/well or HT-1080 cell/scFv or Ab dilution were pipetted in triplicate in two 96-well plate, black, ultra thin clear flat bottom special optics (Costar #3615). One plate was kept on ice in the dark while the other plate was irradiated on an ice block with continuous wave laser at 488 nm (0.5 W, 30 sec). After dilution to $6.7×10^5$ cells/ml with DMEM/GlutamaxI/0.1% BSA, HT-1080 cells and HT-1080 cell/scFv dilutions were pipetted in triplicate (non irradiated triplicate beside irradiated triplicate) onto the coated and blocked plate. In Row A well 10-12

$6.7×10^5$ cells/ml with DMEM/GlutamaxI/0.1% BSA were pipetted as a background control. Plate was incubated for 1 h at 37° C., 7.5% $CO_2$ and washed 2× with Dulbeccos PBS, where non-adherent cells were washed away. In Row A well 1-9 a standard curve from $1×10^4$ to $4×10^4$ cells/well was performed, in all other wells 50 µl Dulbeccos PBS was pipetted. Fluorescence of cells, which had adhered to the Collagen S type 1 (not adhered in case of the Standard curve), was measured on the Fluostar Galaxy (bMG) microplate reader using excitation/emission wavelengths of 370/460 nm. scFv1 inhibited the adhesion of HT-1080 cells to Collagen S type 1 by 50%. (Data not shown).

Example 11

Immunoprecipitation

For immunoprecipitation of mAbs, confluent monolayers of HT-1080 cells were lysed using 1 mM Tris-Cl, pH 8.0 containing protease inhibitor cocktail (Bohrenger Mannheim) for 15 minutes at 4° C. Cells were further lysed using a dounce homogenizer for 5 minutes. Lysates were pre-adsorbed for 1 hour at 4° C. with anti-mouse IgG-agarose (Sigma) Ascities fluid from the target hybridoma clone (10 µL/1 mg cell extract) was incubated overnight at 4° C. Antibody-protein complexes were isolated using anti-mouse IgG-agarose beads for 1 hour at 4° C. Immunoprecipitated proteins were analyzed by SDS-PAGE and Coomassie staining, and mAb immunoprecipitates were further analyzed by immunoblots with the target ascities.

For scFv immunoprecipitations, HT-1080 specific scFvs were coupled to StrepTactin Sepharose (50 µm/50l resin) and the washed scFv-beads added to the cleared lysates (1 mg total protein) for 2-3 h at 4° C. The scFv-target complexes were eluted with 50 µl 10 mM D-desthiobiotin in PBS 0.1% Tween 20. Immunoprecipitated proteins were analyzed by SDS-PAGE and silver staining.

Example 12

Protein Identification Via Mass Spectroscopy

For mAb target identification, coomassie-stained bands from the immunoprecipitates separated by SDS-PAGE were next subjected to in-gel digestion. The trypsinized peptide fragments were run on a Surveyor HPLC and LCQ Deca Ion Trap mass spectrometer (ThermoFinnigan) with a 75 µM nanospray C18 column (New Objectives). The obtained PMF (peptide mass fragments) were used to search all entries for the species *Homo sapiens* in the NCBI and SwissProt databases.

For scFv target identification, stained bands were cut out and subjected to in-gel digestion with trypsin. The peptide fragments were extracted from the gel pieces, desalted on ZipTip µC18 and the eluted peptides spotted on a Teflon-coated MALDI target (Applied Biosystems). The samples were analyzed on a STR-DE Voyager MALDI mass spectrometer (Applied Biosystems) and the obtained peptide masses were used for protein identification via PMF (peptide mass fingerprint), searching all entries for the species *Homo sapiens* in the NCBI and Swiss-Prot databases.

Example 13

Immunocytochemistry

For surface protein immunocytochemistry, a confluent monolayer of HT-1080 cells (40,000 per well of a 96-well clear thin bottom plate) were incubated with hybridoma supernatant for 1 hour at 37° C./7% $CO_2$. After three 5 minute 0.1% bovine serum albumin (BSA) in phosphate buffered saline (PBS) washes, the cells were fixed in 2% paraformaldehyde for 2 minutes. Another round of 0.1% BSA/PBS washes was performed and a FITC-rabbit-anti-mouse secondary antibody was added for 1 hour at room temperature. The same washes were repeated and a tertiary FITC-goat-anti-rabbit antibody was added for 1 hour at room temperature. After a final round of washes, the cells were stored in PBS at 4° C. until imaging. Surface staining was visualized by microscopy on a Zeiss Axiovert 10 using a Neofluar 40X/0.75 numerical aperture lens. Images were collected using excitation filter set at 480 and emission filter set at 535 for FITC. Results are shown in FIGS. 6, 6.1 and 6.2.

Example 14

Biotinylation of Cell Surfaces

Figure 7:
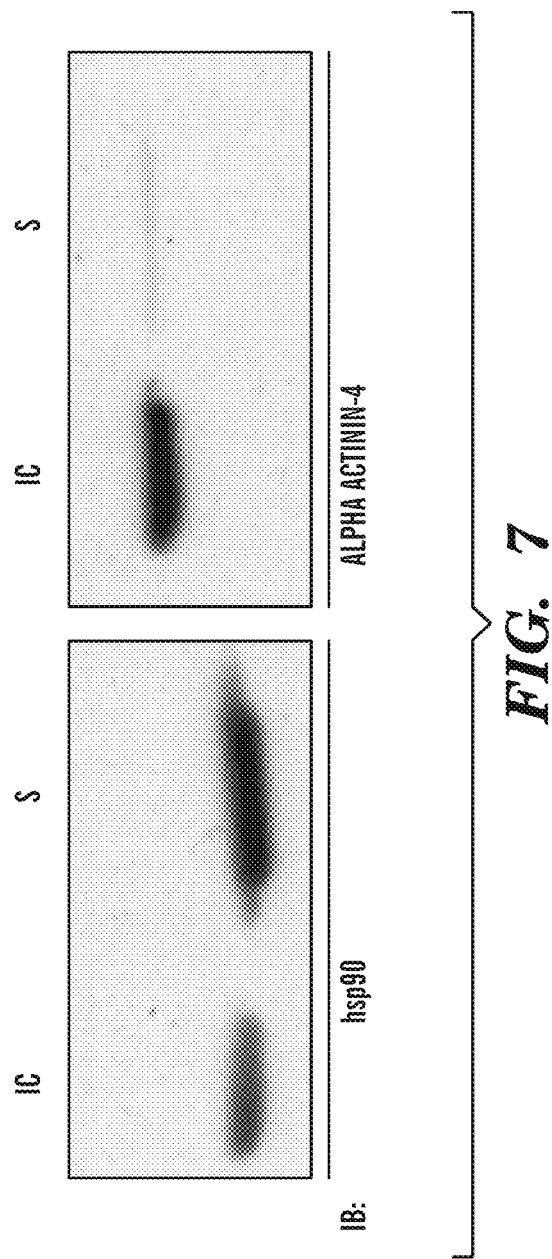
FIG. 7 shows a surface protein biotinylation experiment that was performed with live HT-1080 cells as previously described. Both, the surface biotinylated proteins and the unbiotinylated intracellular proteins were separated by SDS-PAGE. Hsp90 and alpha-actinin-4 antibodies were used for immunoblot analysis. Hsp90 shows both surface (S) and intracellular (IC) localization, but alpha-actinin is found only in the intracellular pool.

Biotinylation of cell surface proteins was performed as described in Hanwell at al (J Biol Chem 277:9772). The surface biotinylated pool and the unbiotinylated intracellular pool were separated on a SDS-PAGE gel, and transferred for immunoblotting with anti-Hsp90 (Stressgen #SPA-830) or alpha-actinin-4 (Martin A. Pollak, Childrens Hospital, Boston, Mass.). Results are shown in FIG. 7. Hsp90 shows both surface (S) and intracelluar (IC) localization, but alpha-actinin is found only in the intracellular pool. mAb 1.5.1 also shows surface and intracellular localization (data not shown).

Example 15

Figure 10:
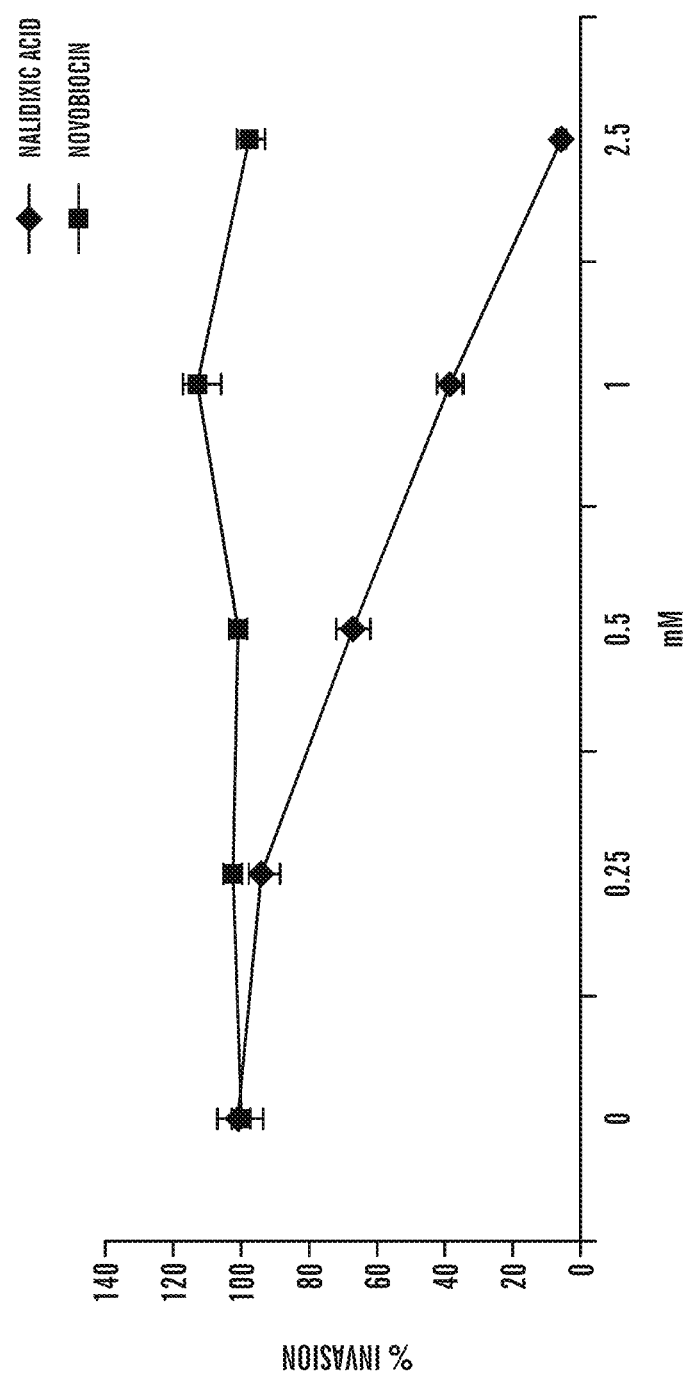
FIG. 10 shows the concentration-dependent effect of novobiocin on invasion of HT-1080 cells. HT-1080 cells were pre-treated for 1 hour with novobiocin or nalidixic acid and an invasion assay was performed. Novobiocin shows a dose-dependent inhibition of invasion (p.ltoreq.0.01 at >0.05 mM by ANOVA). Nalidixic acid has no effect on invasion. Viability of cells in this assay was not affected (data not shown). Each data point is normalized to the no drug control and represents the mean.+-.s.e.m. of 2 experiments in triplicate.

Concentration Dependency of Novobiocin or Nalidixic Acid on the Invasion of HT-1080 Cells $8×10^6$ HT-1080 cells/mL were pretreated for 1 hour with novobiocin or nalidixic acid at the concentrations shown and an invasion assay was performed as described in Example 9.1. Novobiocin shows a dose-dependent inhibition of invasion (p<0.01 at >0.5 mM). Nalidixic acid has no effect on invasion. Viability of novobiocin-treated cells in this assay was not affected (data not shown). Each data point is normalized to the no drug control and represents the mean.+−.s.e.m. of 2 experiments in triplicate. Results are shown in FIG. 10.

Example 16

Figure 11:
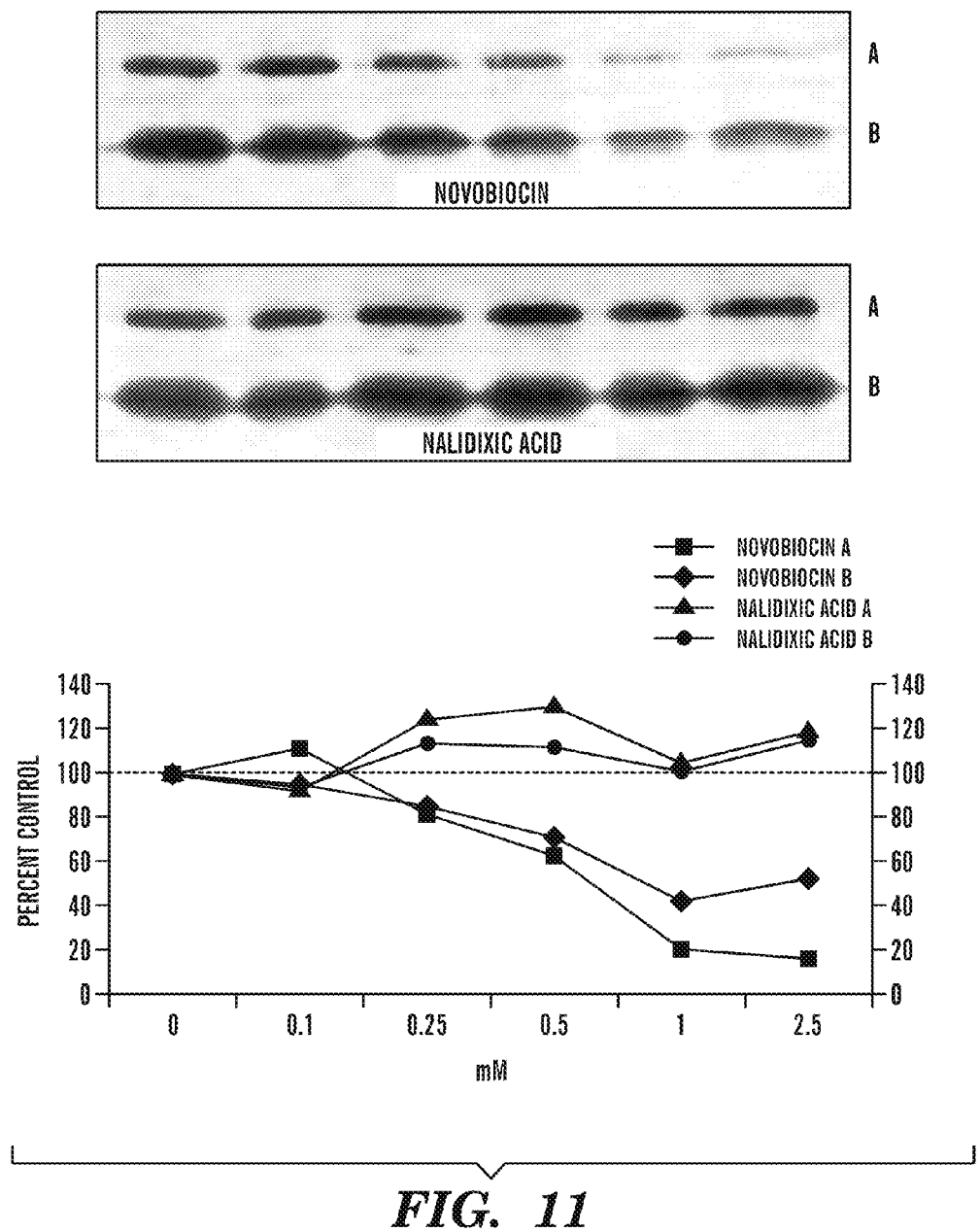
FIG. 11 shows that MMP secretion is decreased after addition of novobiocin. 40,000 HT-1080 cells were treated for 6 hours with novobiocin or nalidixic acid (as a control) at the given concentrations. MMP activity was decreased by >75% at the highest concentration of novobiocin tested and no reduction of enzyme activity was seen with nalidixic acid. Two bands (A and B) correspond to unidentified MMPs. (Image inverted for clarity.)
Figure 12:
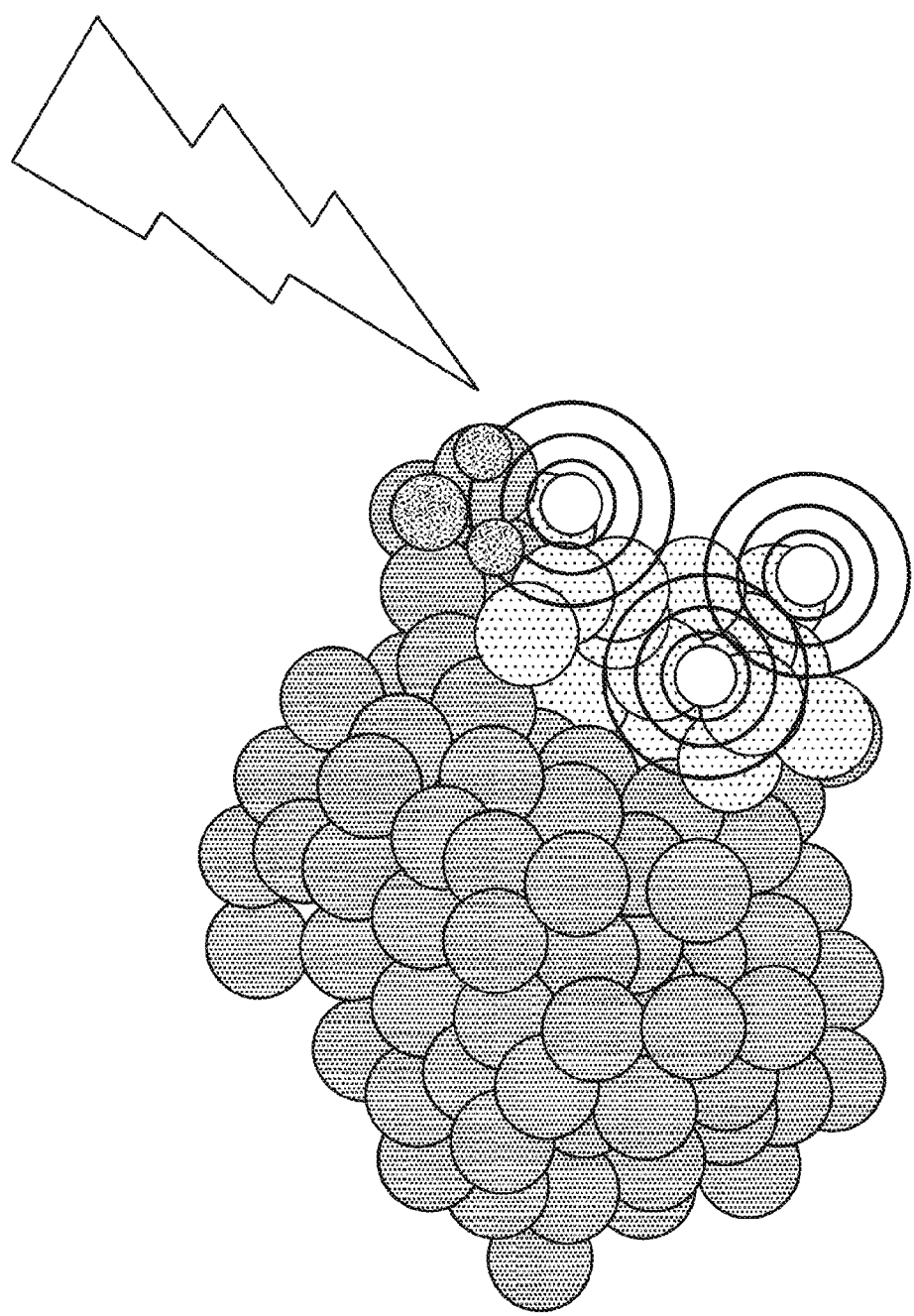
FIG. 12 shows the principle of Chromophore Assisted Laser/Light Inactivation (CALI)
Figure 13A:
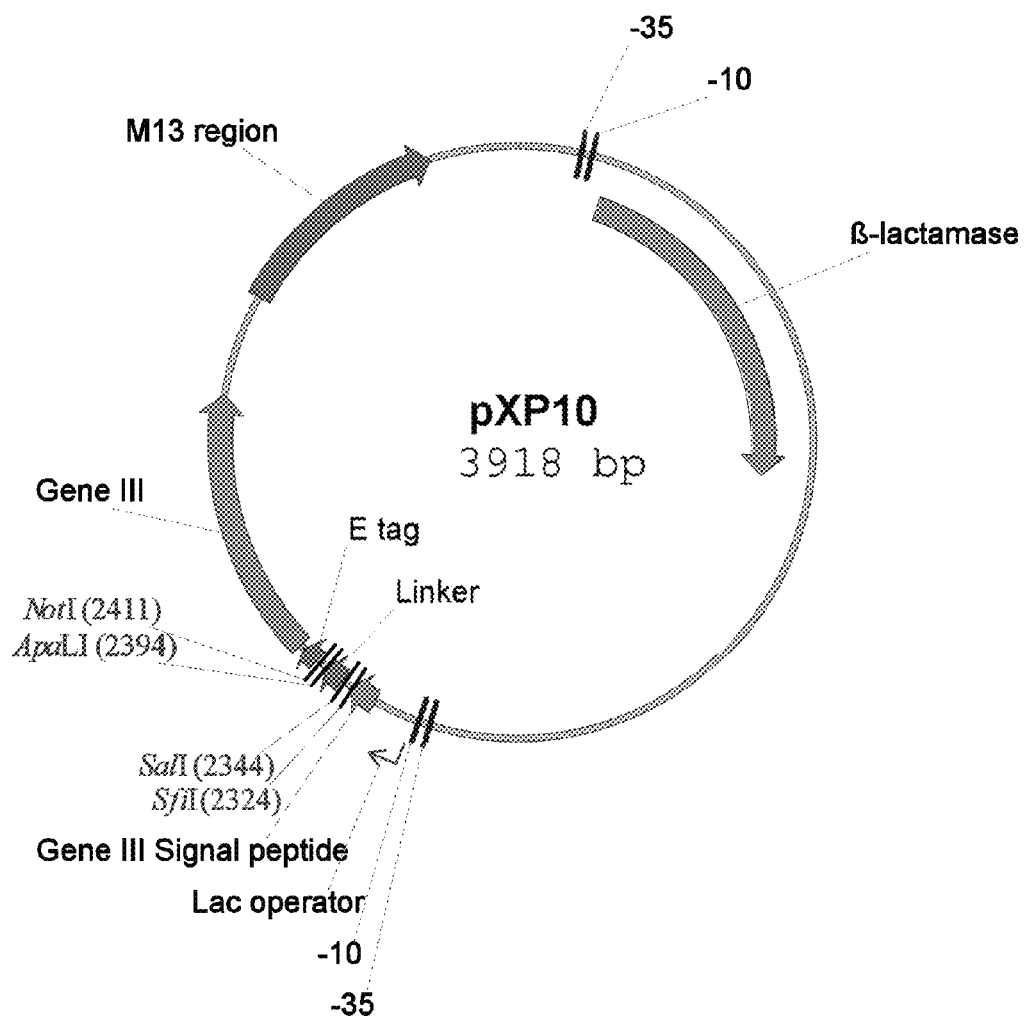
Figure 14A:
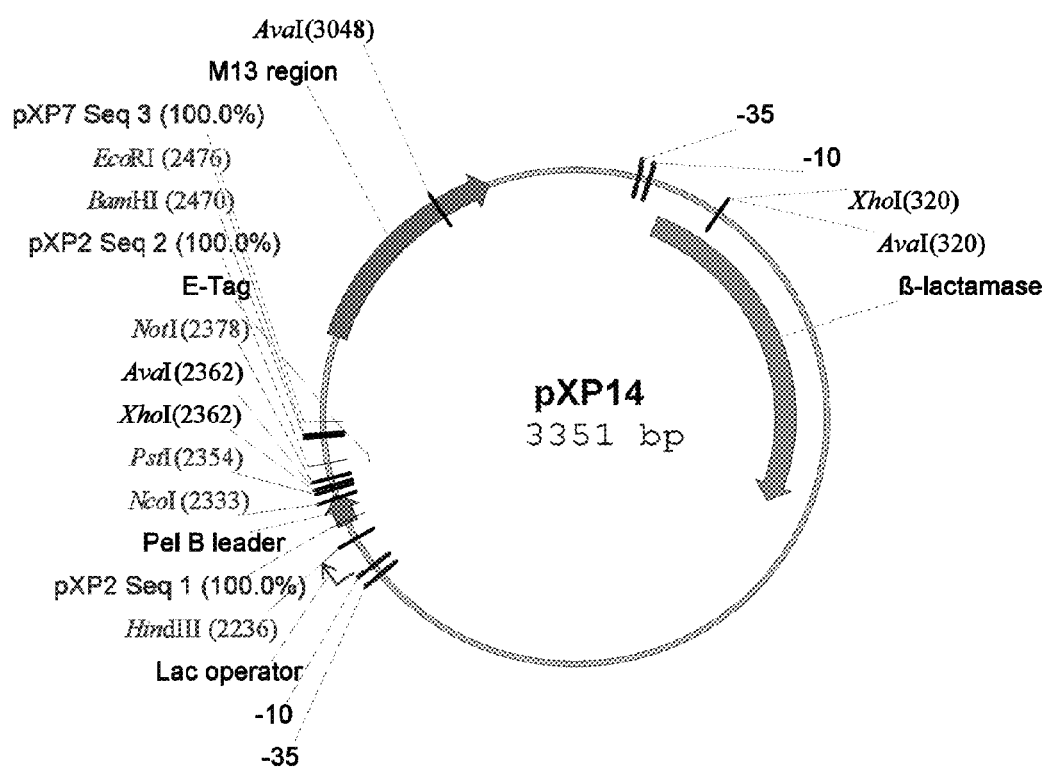

Inhibition of MMP Secretion 40,000 HT-1080 cells were treated for 6 hours with novobiocin or nalidixic acid at the given concentrations. The conditioned media from treated cells was separated using a SDS-PAGE gel containing 10 mg/mL gelantin. SDS was removed from the gel using 2.5% Triton-X-100 for 30 minutes at room temperature. Proteins were allowed to digest the gelatine in digestion buffer (0.1M Tris-$Cl_2$, pH 8.0, 5 mM $CaCl_2$, 0.04% $NaN_3$) for 48 hours at 37° C. Gels were coomassie-stained and dried for densitometry. Parallel gels were silver stained to show equal loading of protein (data not shown). MMP activity was decreased by >75% at the highest concentration of novobiocin tested and no reduction of enzyme activity was seen with nalidixic acid. Results are shown in FIG. 11.

Example 17

Covalent Coupling of Novobiocin to Sepharose and Inhibition of MMP Activity

This example demonstrates inhibition of Hsp90 function on the surface of HT-1080 cells. It has been shown that treatment of HT-1080 fibrosarcoma cells with novobiocin, a coumarin antibiotic, reduces the cell's ability to invade a basement membrane barrier and also significantly reduces matrix metalloprotease (MMP) activity/secretion. Since the experiment is performed on a short timescale (6 hours), significant depletion of intracellular Hsp90 targets can not take place.

The covalent coupling of novobiocin to a macromolecular carrier like sepharose prohibits cellular uptake of novobiocin and consequently any intracellular inhibition of Hsp90. Marcu et al described a protocol for novobiocin conjugation to sepharose (Marcu et al. (2000) J Natl Cancer Inst 92, 242-8; Staudenbauer and On (1981) Nucleic Acids Res. 9, 3589-603). In this procedure epoxy-activated Sepharose 6B (Sigma Chemical Co) is first washed and swollen with distilled water. The swollen beads are washed further with a coupling buffer (0.3M sodium carbonate, pH 9.5). Novobiocin is formally conjugated to the beads by incubation with the swollen beads in coupling buffer for 20 hours at 37° C. Unconjugated novobiocin is washed away using coupling buffer, and the remaining unbound epoxy-active groups are blocked with 1M ethanolamine for 12 hours at 30° C. Extensive washing of the beads using 0.5M NaCl in coupling buffer, distilled water, 0.5M NaCl in 0.1M sodium acetate (pH4.0) is done to remove any excess novobiocin and ethanolamine. The novobiocin-sepharose beads are then equilibrated in 25 mM HEPES (pH 8.0) with 1 mM EDTA, 10% ethylene glycol, and 200 mM KCl at 4° C. in the dark.

Before proceeding to the gelatinase experiment, efficient binding of the novobiocin-sepharose conjugate to Hsp90 is demonstrated by an in vitro binding assay. HT-1080 cells are lysed in TNESV (1% Nonidet P-40, 2 mM EDTA, and 100 mM NaCl, and 1 mM sodium orthovanadate) with protease inhibitors (tablet. Boehringer Mannheim). 300 μg of this lysate are incubated with 100 μL of the novobiocin-sepharose conjugate for 1 hour at 4° C. After extensive washing with TNESV, proteins bound to the beads are eluted with 2×SDS-PAGE loading buffer (125 mM Tris-HCl pH6.8, 10% 2-mercaptoethanol, 10 SDS, 10% glycerol, and trace bromophenol blue) and boiling for 5 minutes. The proteins are run on 10% SDS-PAGE gels. These gels are either silver stained or transferred to nitrocellulose for immunoblotting with an anti-Hsp90 antibody (AC88, Stressgen, Inc.)

For the gelatinase assay, adherent HT-1080 cells are first gently removed from tissue culture dishes with Versene. $5 \times 10^4$ cells in serum-free DMEM are combined with 0.1 μL, 1 μL, or 10 μL of the novobiocin-sepharose conjugate and incubated at room temperature for one hour in siliconized eppendorf tubes with gentle rocking Control samples containing sepharose beads not conjugated to novobiocin are done in parallel. After this incubation, the cells are transferred to a tissue culture treated 96-well plate and incubated further for 6 hours at 37° C./5% $CO_2$. Conditioned media from these samples are then combined with 2×SDS-PAGE loading buffer (without 2-mercaptoethanol). These samples are run on a 10% SDS-PAGE gel containing 10 mg/mL gelatine. SDS is then removed from the gel by incubating with 2.5% Triton-X-100 for 30 minutes at room temperature. Proteins are allowed to digest the gelatine in digestion buffer (0.1M Tris-HCl, pH 8.0, 5 mM $CaCl_2$, 0.04% $NaN_3$) for 48 hours at 38° C. Gels will be coomassie-stained and dried for densitometry. Parallel gels are silver stained to show equal loading of protein. MMP activity decreases with increasing amounts of novobiocin-sepharose.

Example 18

Inhibition of MMP Activity by Geldanamycin and Immobilized Geldanamycin (GA-Beads)

Figure 17:
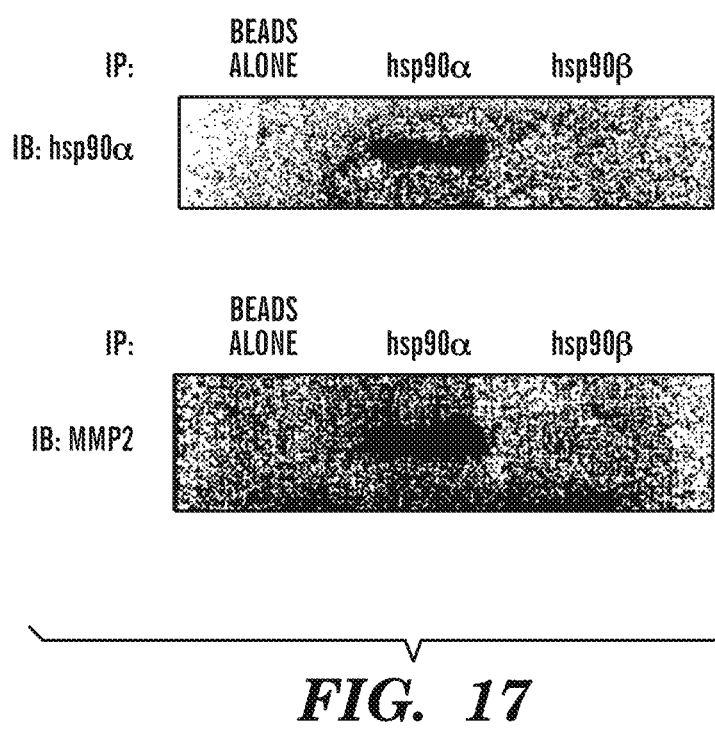
FIG. 17 shows that an anti-Hsp90α antibody co-immunoprecipitates MMP2 from HT-1080 conditioned media. Immunoprecipitated proteins were immunoblotted with anti-MMP2 or Hsp90α. Inhibition of Hsp90 inhibits MMP2 secretion.
Figure 18:
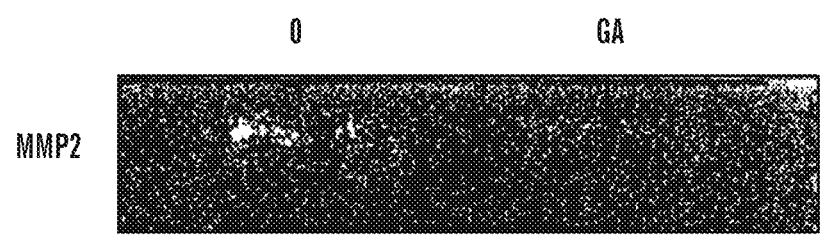
FIG. 18 shows the MMP2 content in conditioned media after geldanamycin (GA) treatment. HT-1080 cells were treated with 20 μM geldanamycin (GA) in serum-free media and assayed by zymography. MMP2 (72 kDa gelatinase) activity was decreased by ~35% after GA treatment. Total protein content was visualized by silver staining to ensure equal loading.

It could be shown that the matrix metalloproteinase MMP2 co-immunoprecipitated with Hsp90α from HT-1080 conditioned media (FIG. 17). We then applied a known Hsp90 inhibitor, geldanamycin, to HT-1080 cells to test whether inhibition of Hsp90 reduced MMP2 activity. HT-1080 cells were treated with 20 μM geldanamycin (GA) in serum-free media and secreted MMP2 was assayed by zymography. MMP2 (72 kDa gelatinase) activity was decreased by ~35%; $p<0.01$ after GA treatment. Total protein content in conditioned media was visualized by silver staining to ensure equal loading. (See, FIG. 18).

Figure 19:
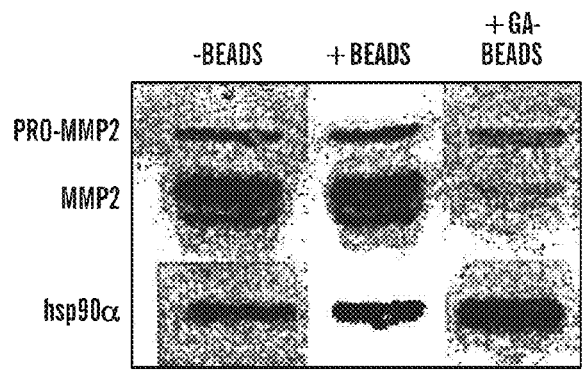
FIG. 19 shows a correlation between the MMP2 content and the hsp90α content. HT-1080 cells were treated with geldanamycin-conjugated agarose beads (GA-beads) or control beads (beads) or left untreated (O). Conditioned media was immunoblotted for MMP2 or Hsp90α. Active MMP2 levels were decreased by 80%, and pro-MMP2 levels were decreased by 15% after GA-bead treatment.
Figure 20:
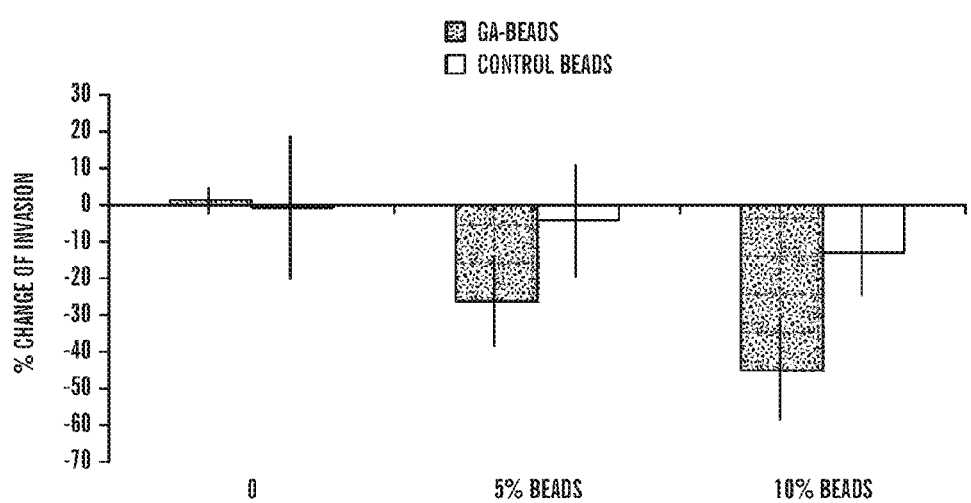
FIG. 20 shows the decrease of invasiveness of tumor cells after treatment with different amounts of geldanamycin-conjugated agarose beads (GA-beads). HT-1080 cells were treated either with no beads, 5% or 10% (v/v) of GA-beads or control beads and assayed for invasiveness. GA-bead treated cells show a 45% reduction, whereas control bead treated cells only show a 15% reduction in invasiveness (p<0.01, t-test). Each data point is normalized to the no treatment control and represents the mean.+-.standard error of two triplicate assays.

Geldanamycin is a well-known cell-permeant inhibitor of Hsp90. Treatment with 10 μM geldanamycin (GA) for 1 hour caused a significant ~35% decrease ($p<0.05$, t-test) of invasion of HT-1080 cells that was eliminated when activated MMP2 (100 ng) was added. (Data not shown). Due to its cell-permeability, geldanamycin cannot segregate the intracellular and extracellular localization of Hsp90. In order to show Hsp90's extracellular role in tumor cell invasion, geldanamycin was immobilized on agarose beads (GA-beads) to prevent crossing of the plasma membrane. (See, Whitesell et al, Proc Natl Acad Sci USA 91, 8324-8 (1994)) for experimental details). After treatment of HT-1080 cells with the GA-beads, an 80% reduction of active MMP2 was seen in conditioned media, but only a 15% reduction of pro-MMP2 (FIG. 19). HT-1080 cells treated with GA-beads showed a significant 45% reduction of invasiveness ($p<0.01$, t-test) using an in vitro invasion assay (see, Example 8). Untreated beads also inhibited invasion to a limited extent (<15%), likely due to physical blocking of pores by the beads. (See, FIG. 20). All of these results together suggest a mechanism where extracellular Hsp90α binding to pro-MMP2 assists in activation of the protease, leading to an invasive phenotype Inhibition of Hsp90α leads to a reduction of active MMP-2 and a reduced invasiveness of tumor cells.

The invention claimed is:

1. An assay for selecting a subject with invasive or metastatic cancer to be treated with a Hsp90 inhibitor treatment, wherein the Hsp90 inhibitor treatment is an anti-Hsp90 antibody or fragment thereof which binds to human extracellular Hsp90, the assay comprising:
   a. subjecting a biopsy sample from the subject to immunohistological staining with an antibody or antibody fragment that binds to human extracellular Hsp90
   b. measuring the binding of the antibody or antibody fragment to human extracellular Hsp90 on the surface of cells in the biopsy sample; and
   c. selecting the subject with invasive or metastatic cancer to be treated with the Hsp90 inhibitor treatment where the immunohistological staining shows localization of the antibody or antibody fragment that binds to human extracellular Hsp90 on the surface of cells in the biopsy sample.

2. The assay of claim 1, wherein the antibody or antibody fragment is a monoclonal antibody.

3. The assay of claim 1, wherein the antibody or antibody fragment is unable to enter a cell.

4. The assay of claim 1, wherein the antibody or antibody fragment is labelled with a detectable label.

5. The assay of claim 1, wherein the antibody or antibody fragment is recombinantly produced antibody or antibody fragment.

6. The assay of claim 1, wherein the antibody or antibody fragment is a humanized antibody or antibody fragment.

7. The assay of claim 1, wherein the antibody or antibody fragment is a human antibody or antibody fragment.

8. The assay of claim 7, wherein the human antibody or antibody fragment is a human monoclonal antibody.

9. The assay of claim 1, wherein the cancer is selected from the group consisting of; breast adenocarcinoma, melanoma, fibrosarcoma.

10. The assay of claim 1, wherein the antibody or antibody fragment is an anti-Hsp90α antibody or antibody fragment.

11. The assay of claim 1, wherein the cancer is a solid tumor.

12. The assay of claim 1, further comprising administering an anti-Hsp90 antibody or antibody fragment which binds to human extracellular Hsp90 to the subject selected to be treated with the Hsp90 inhibitor treatment.

* * * * *